(12) United States Patent
Weaver et al.

(10) Patent No.: US 8,123,785 B2
(45) Date of Patent: Feb. 28, 2012

(54) MINIMALLY INVASIVE SPINAL STABILIZATION SYSTEM

(75) Inventors: Paul C. Weaver, Douglassville, PA (US); Brian E. Dalton, Erie, PA (US)

(73) Assignee: Aesculap Implant Systems, LLC, Center Valley, PA (US)

( * ) Notice: Subject to any disclaimer, the term of this patent is extended or adjusted under 35 U.S.C. 154(b) by 951 days.

(21) Appl. No.: 12/117,294

(22) Filed: May 8, 2008

(65) Prior Publication Data
US 2009/0281576 A1    Nov. 12, 2009

(51) Int. Cl.
*A61B 17/80* (2006.01)
(52) U.S. Cl. ......... 606/279; 606/272; 606/281; 606/282
(58) Field of Classification Search .................. 606/279, 606/280, 301, 305, 308, 264–275, 282, 286–296
See application file for complete search history.

(56) References Cited

U.S. PATENT DOCUMENTS

| | | | |
|---|---|---|---|
| 4,463,753 A | 8/1984 | Gustilo |
| 4,484,570 A | 11/1984 | Sutter et al. |
| 5,129,899 A | 7/1992 | Small et al. |
| 5,147,363 A | 9/1992 | Härle |
| 5,486,176 A | 1/1996 | Hildebrand et al. |
| 5,520,690 A | 5/1996 | Errico et al. |
| 5,531,746 A | 7/1996 | Errico et al. |
| 5,540,690 A | 7/1996 | Miller et al. |
| 5,607,426 A | 3/1997 | Ralph et al. |
| 5,620,443 A | 4/1997 | Gertzbein et al. |
| 5,669,911 A | 9/1997 | Errico et al. |
| 5,735,853 A | 4/1998 | Olerud |
| 5,749,916 A | 5/1998 | Richelsoph |
| 5,797,911 A | 8/1998 | Sherman et al. |
| 5,800,433 A | 9/1998 | Benzel et al. |
| 5,863,293 A | 1/1999 | Richelsoph |
| 5,876,402 A | 3/1999 | Errico et al. |
| 5,879,350 A | 3/1999 | Sherman et al. |
| 5,885,286 A | 3/1999 | Sherman et al. |
| 5,954,635 A | 9/1999 | Foley et al. |
| 5,954,722 A | 9/1999 | Bono |
| 5,964,760 A | 10/1999 | Richelsoph |
| 5,976,187 A | 11/1999 | Richelsoph |
| 6,022,350 A | 2/2000 | Ganem |

(Continued)

OTHER PUBLICATIONS

International Search Report for International Application No. PCT/US2009/040649, Completed Jul. 10, 2009.

*Primary Examiner* — David H Willse
*Assistant Examiner* — Tiffany Shipmon
(74) *Attorney, Agent, or Firm* — RatnerPrestia

(57) ABSTRACT

A spinal stabilization system includes an implant and instrumentation for stabilizing the spine. In one embodiment, the system includes a plate having a side rail and a channel extending adjacent the side rail. A pedicle screw assembly is positioned in the channel in releasable engagement with the side rail. The pedicle screw assembly includes a polyaxial screw seated in a lower housing having a lower locking flange. An upper housing having an upper locking flange secures the plate to the lower housing. The side rail of the plate is releasably engaged between the upper locking flange and the lower locking flange. The upper and lower housings include on-board locking mechanisms for fixing components in the screw assembly. The screw assembly and plate are inserted and oriented by remote manipulation. Minimally invasive techniques for inserting the implant are performed with the instrumentation, and cause minimal disturbance to surrounding tissue.

21 Claims, 29 Drawing Sheets

U.S. PATENT DOCUMENTS

| | | | |
|---|---|---|---|
| 6,030,389 A | 2/2000 | Wagner et al. |
| 6,033,406 A | 3/2000 | Mathews |
| 6,053,917 A | 4/2000 | Sherman et al. |
| 6,074,391 A | 6/2000 | Metz-Stavenhagen et al. |
| 6,083,225 A | 7/2000 | Winslow et al. |
| 6,096,038 A | 8/2000 | Michelson |
| 6,132,432 A | 10/2000 | Richelsoph |
| 6,146,386 A | 11/2000 | Blackman et al. |
| 6,152,871 A | 11/2000 | Foley et al. |
| 6,159,179 A | 12/2000 | Simonson |
| 6,162,170 A | 12/2000 | Foley et al. |
| 6,171,311 B1 | 1/2001 | Richelsoph |
| 6,197,033 B1 | 3/2001 | Haid, Jr. et al. |
| 6,200,322 B1 | 3/2001 | Branch et al. |
| 6,206,822 B1 | 3/2001 | Foley et al. |
| 6,217,509 B1 | 4/2001 | Foley et al. |
| 6,235,033 B1 | 5/2001 | Brace et al. |
| 6,261,291 B1 | 7/2001 | Talaber et al. |
| 6,280,442 B1 | 8/2001 | Barker et al. |
| 6,280,445 B1 | 8/2001 | Morrison et al. |
| 6,287,311 B1 | 9/2001 | Sherman et al. |
| 6,290,703 B1 | 9/2001 | Ganem |
| 6,299,616 B1 | 10/2001 | Beger |
| 6,328,738 B1 | 12/2001 | Suddaby |
| 6,328,740 B1 | 12/2001 | Richelsoph |
| 6,328,741 B1 | 12/2001 | Richelsoph |
| 6,331,179 B1 | 12/2001 | Freid et al. |
| RE37,665 E | 4/2002 | Ralph et al. |
| 6,402,752 B2 | 6/2002 | Schäffler-Wachter et al. |
| 6,402,756 B1 | 6/2002 | Ralph et al. |
| 6,428,542 B1 | 8/2002 | Michelson |
| 6,451,021 B1 | 9/2002 | Ralph et al. |
| 6,514,260 B1 | 2/2003 | Zdeblick et al. |
| 6,520,907 B1 | 2/2003 | Foley et al. |
| 6,527,776 B1 | 3/2003 | Michelson |
| 6,530,929 B1 | 3/2003 | Justis et al. |
| 6,533,786 B1 | 3/2003 | Needham et al. |
| 6,562,046 B2 | 5/2003 | Sasso |
| 6,565,565 B1 | 5/2003 | Yuan et al. |
| 6,575,899 B1 | 6/2003 | Foley et al. |
| 6,575,975 B2 | 6/2003 | Brace et al. |
| 6,599,290 B2 | 7/2003 | Bailey et al. |
| 6,602,255 B1 | 8/2003 | Campbell et al. |
| 6,623,485 B2 | 9/2003 | Doubler et al. |
| 6,645,207 B2 | 11/2003 | Dixon et al. |
| 6,663,616 B1 | 12/2003 | Roth et al. |
| 6,682,534 B2 | 1/2004 | Patel et al. |
| 6,695,772 B1 | 2/2004 | Bon et al. |
| 6,695,846 B2 | 2/2004 | Richelsoph et al. |
| 6,712,818 B1 | 3/2004 | Michelson |
| 6,712,819 B2 | 3/2004 | Zucherman et al. |
| 6,780,185 B2 | 8/2004 | Frei et al. |
| 6,780,186 B2 | 8/2004 | Errico et al. |
| 2001/0034521 A1 | 10/2001 | Bailey et al. |
| 2001/0037111 A1 | 11/2001 | Dixon et al. |
| 2002/0120273 A1* | 8/2002 | Needham et al. ............... 606/61 |
| 2002/0143328 A1 | 10/2002 | Shluzas et al. |
| 2002/0161368 A1 | 10/2002 | Foley et al. |
| 2002/0183754 A1 | 12/2002 | Michelson |
| 2003/0045875 A1* | 3/2003 | Bertranou et al. ............. 606/61 |
| 2003/0060826 A1 | 3/2003 | Foley et al. |
| 2003/0073996 A1 | 4/2003 | Doubler et al. |
| 2003/0149431 A1 | 8/2003 | Varieur |
| 2003/0208203 A1 | 11/2003 | Lim et al. |
| 2003/0216735 A1 | 11/2003 | Altarac et al. |
| 2004/0039384 A1 | 2/2004 | Boehm, Jr. et al. |
| 2004/0127897 A1 | 7/2004 | Freid et al. |
| 2004/0133207 A1 | 7/2004 | Abdou |
| 2004/0177847 A1 | 9/2004 | Foley et al. |
| 2006/0149245 A1 | 7/2006 | Sweeney |
| 2007/0010817 A1 | 1/2007 | DeConinck |
| 2007/0043359 A1* | 2/2007 | Altarac et al. .................. 606/61 |

* cited by examiner

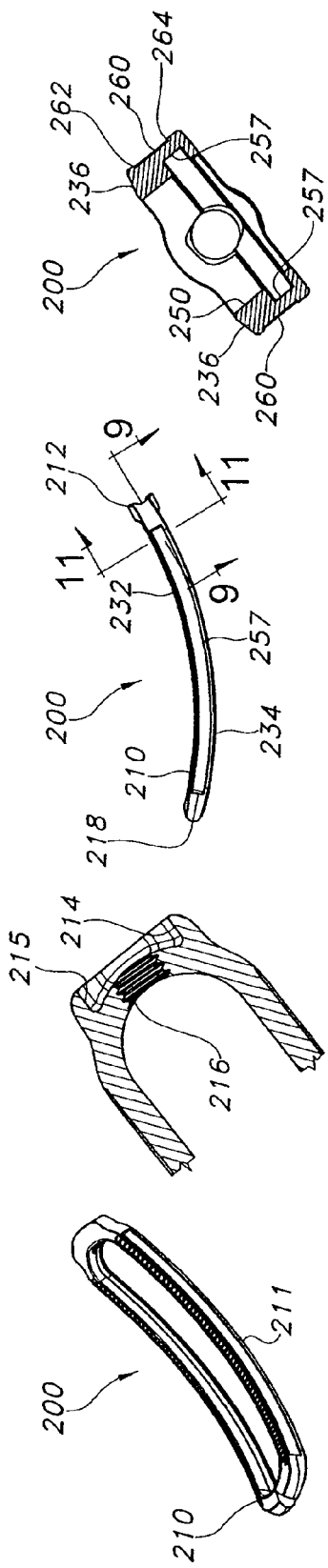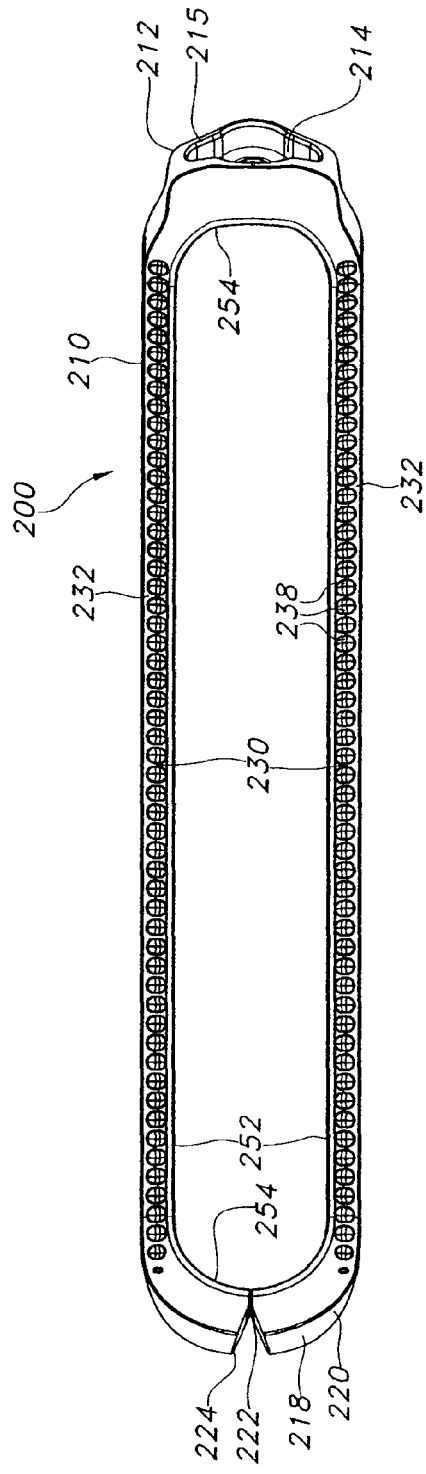

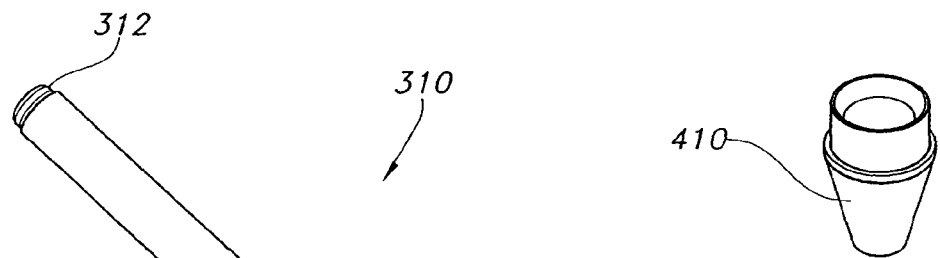
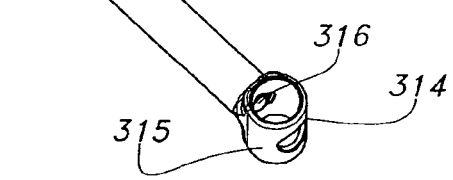
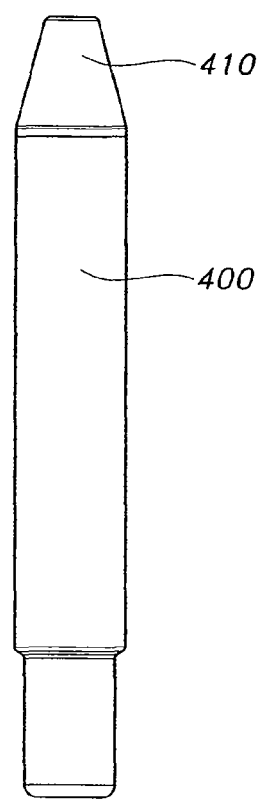
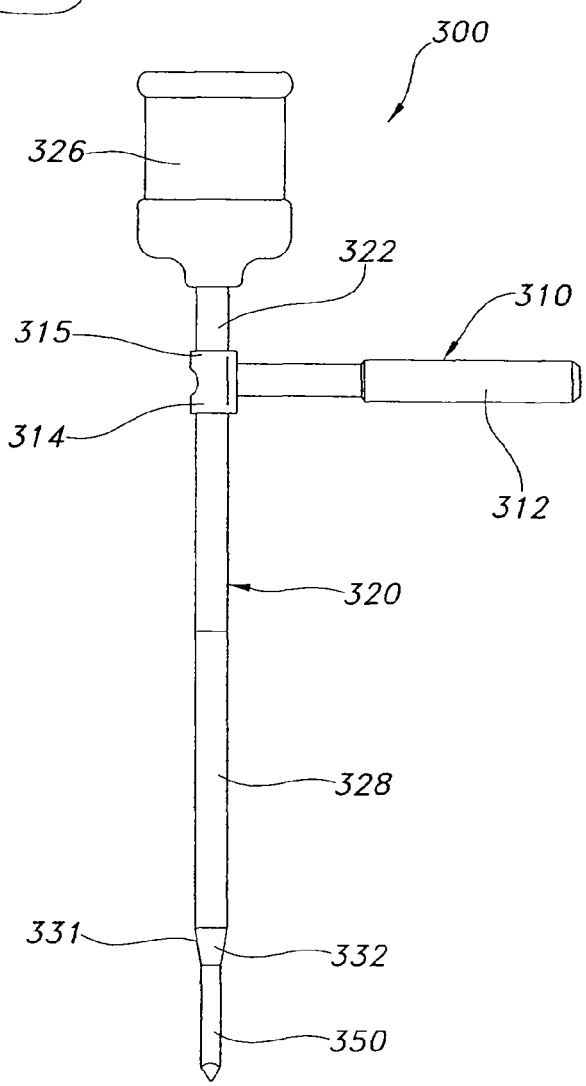
FIG. 15
FIG. 13
FIG. 14
FIG. 12

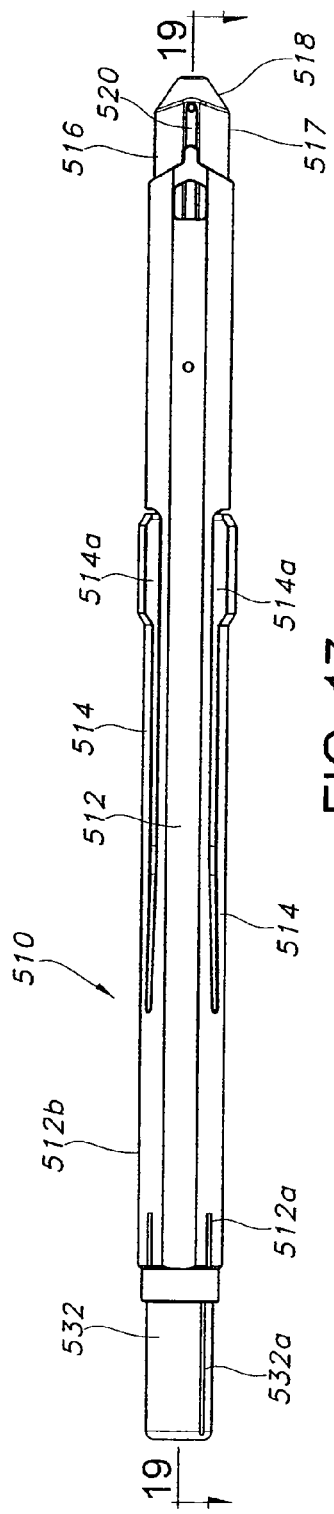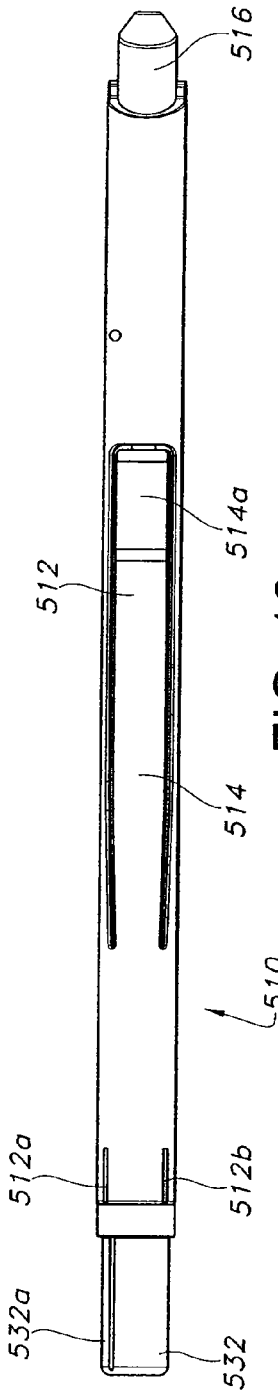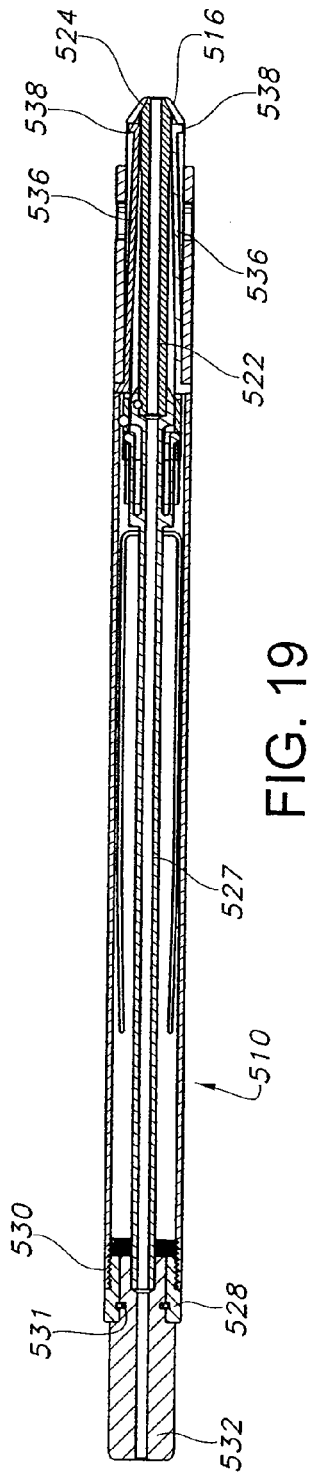

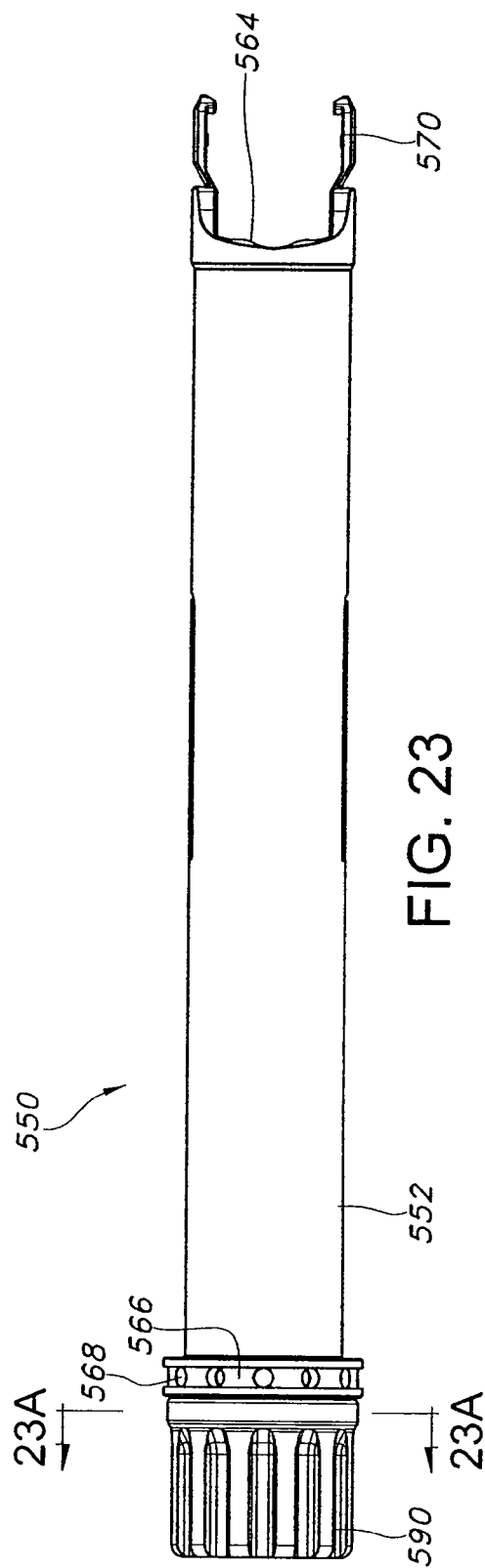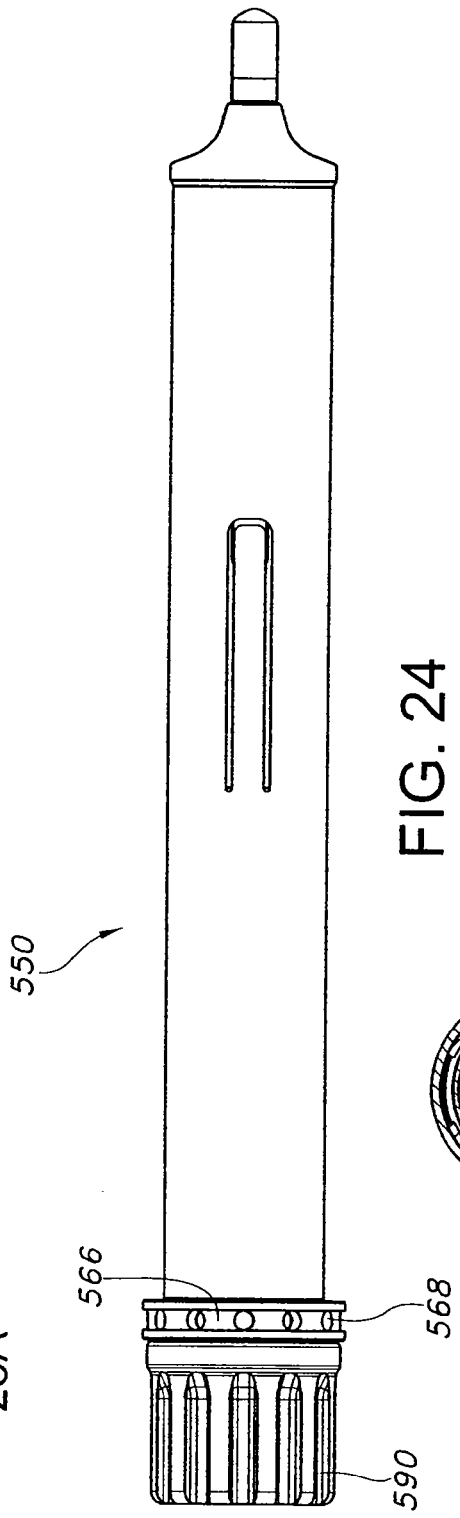
FIG. 23
FIG. 24
FIG. 23A

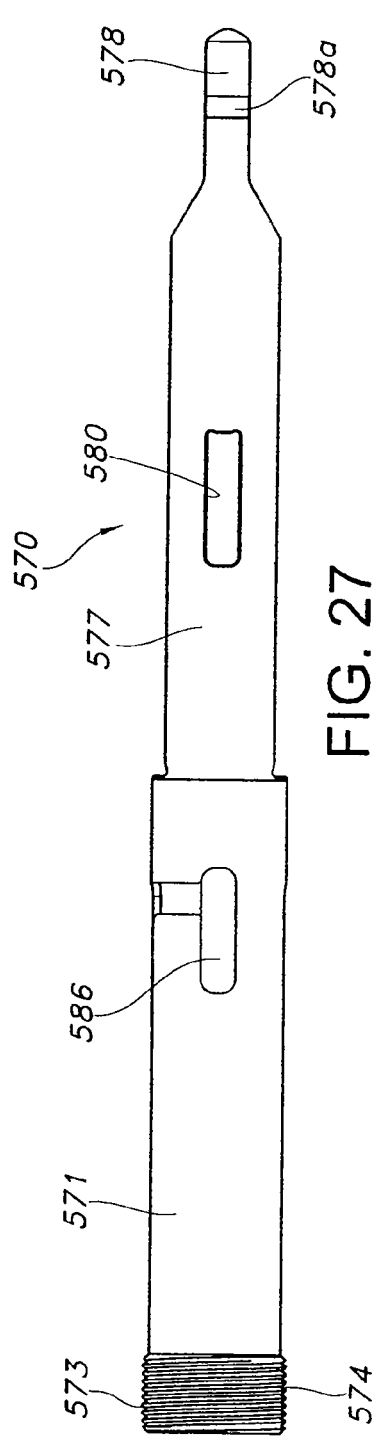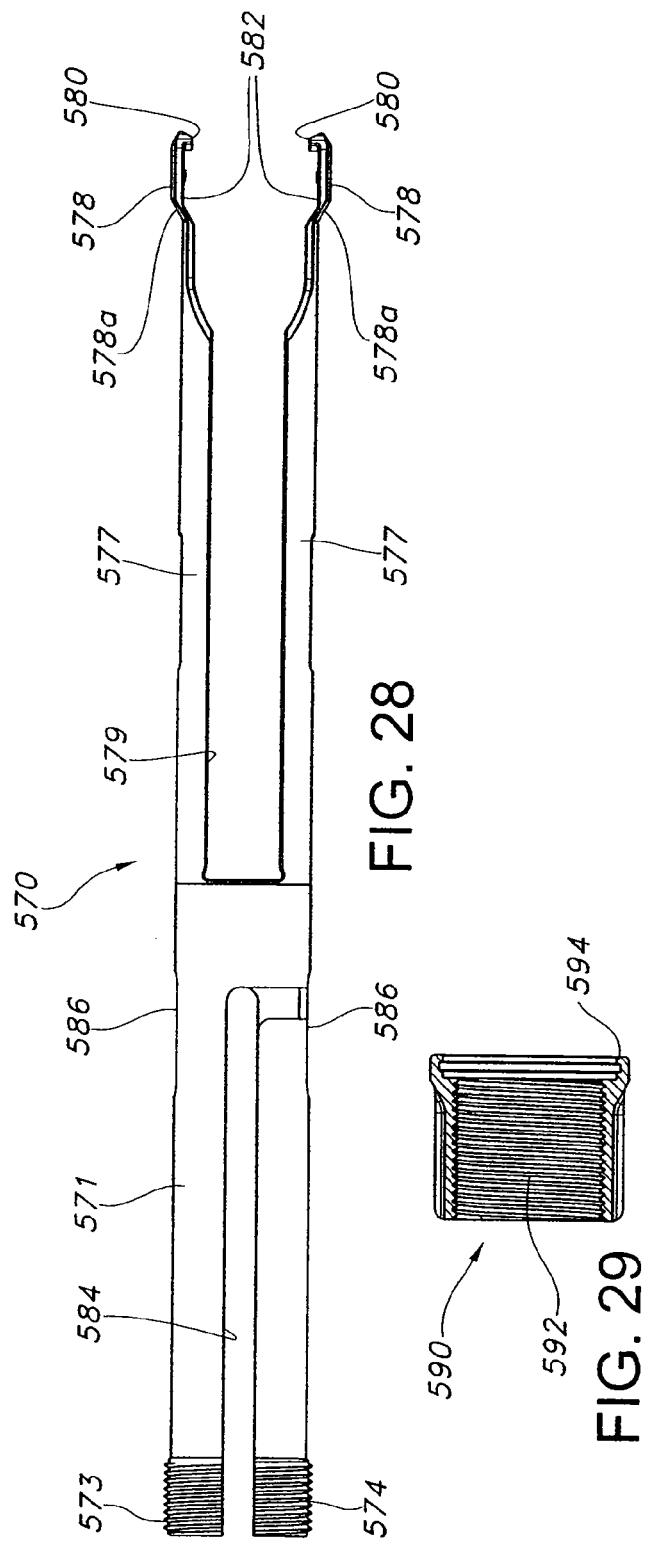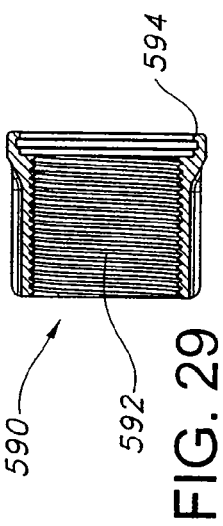

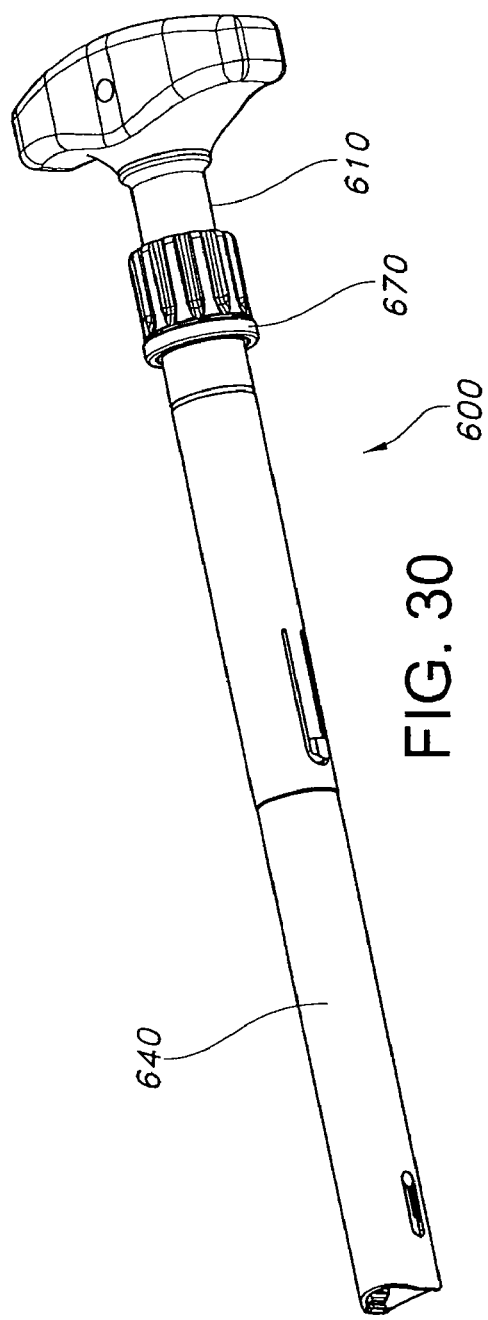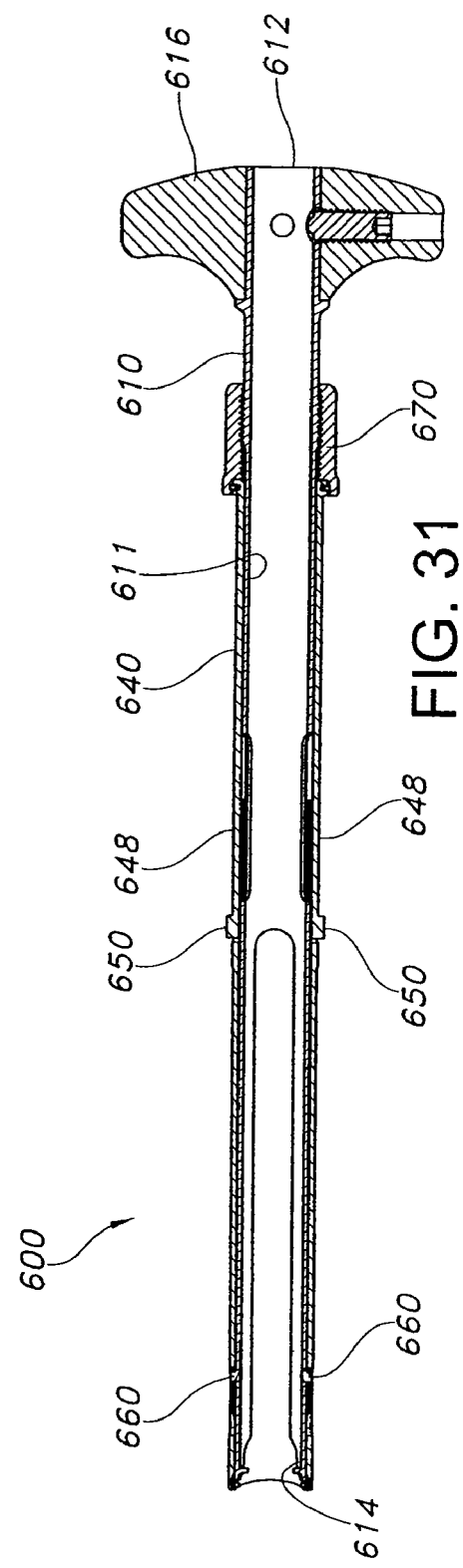

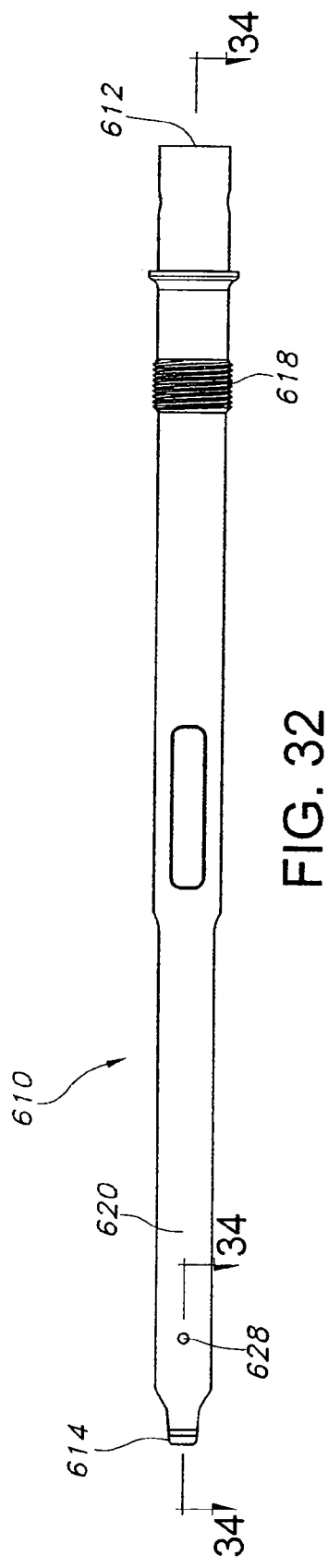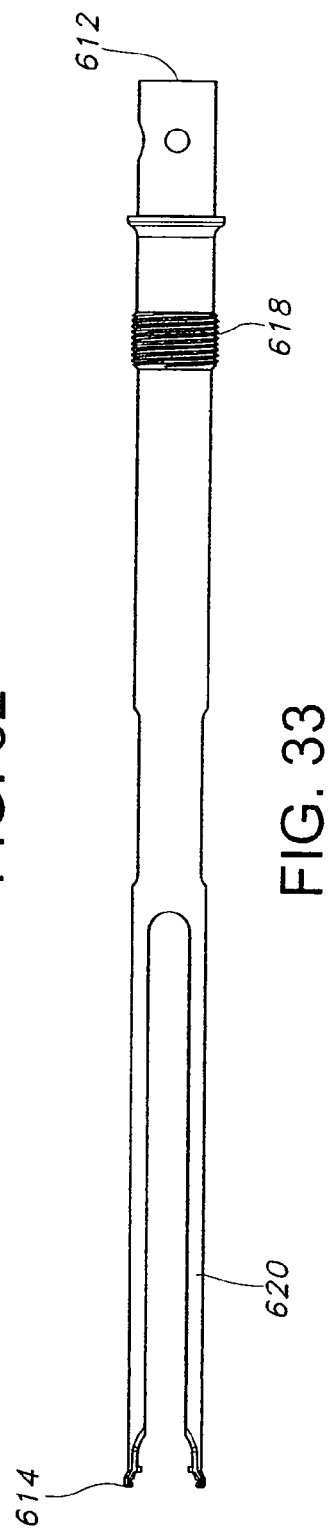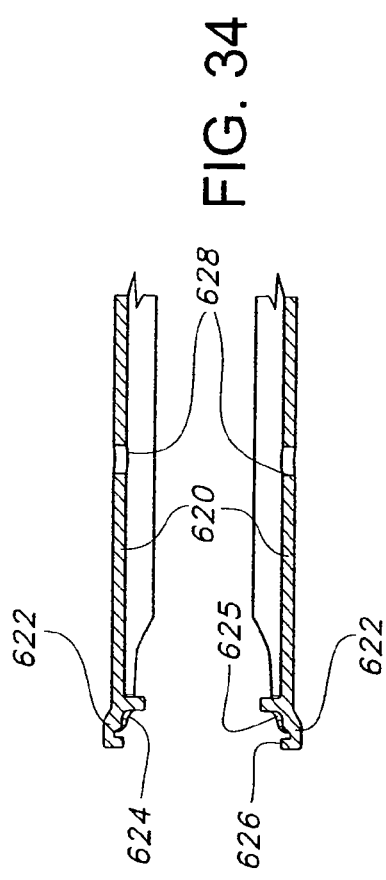
FIG. 32
FIG. 33
FIG. 34

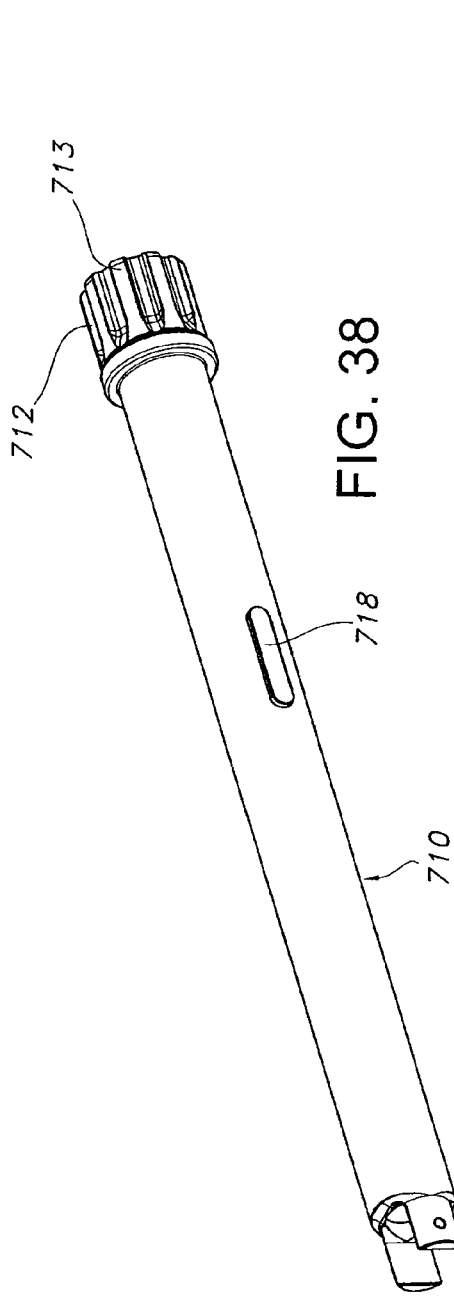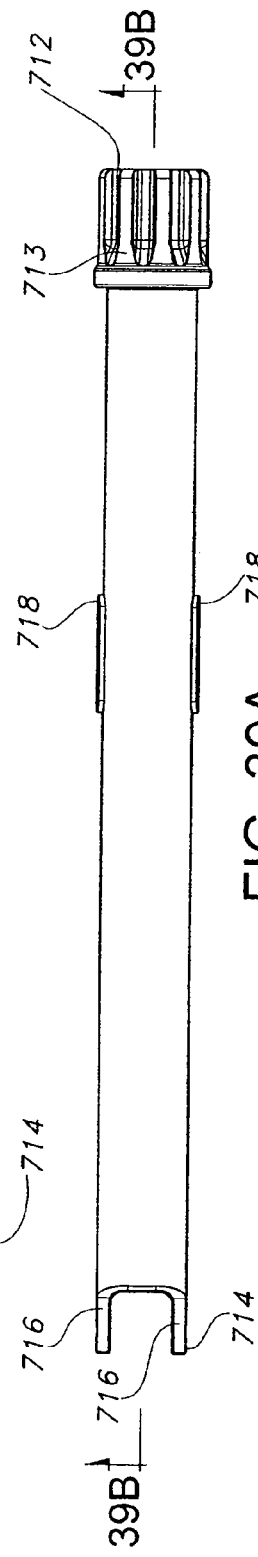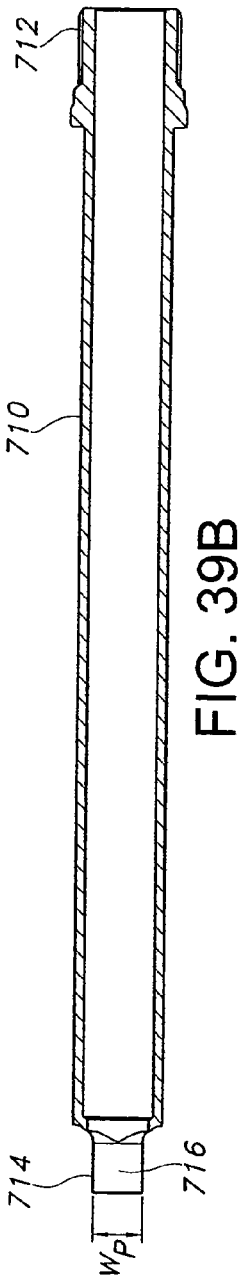

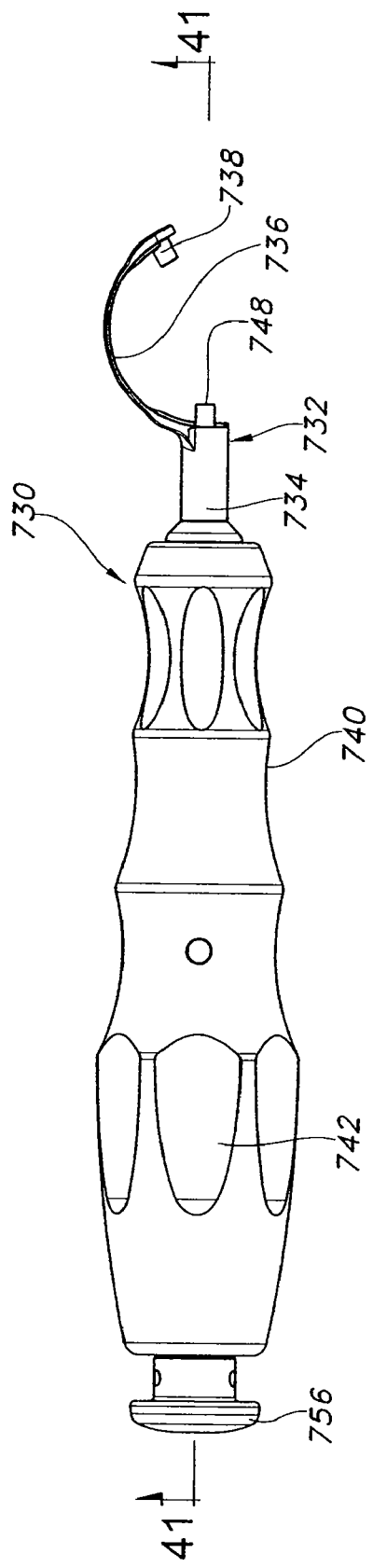
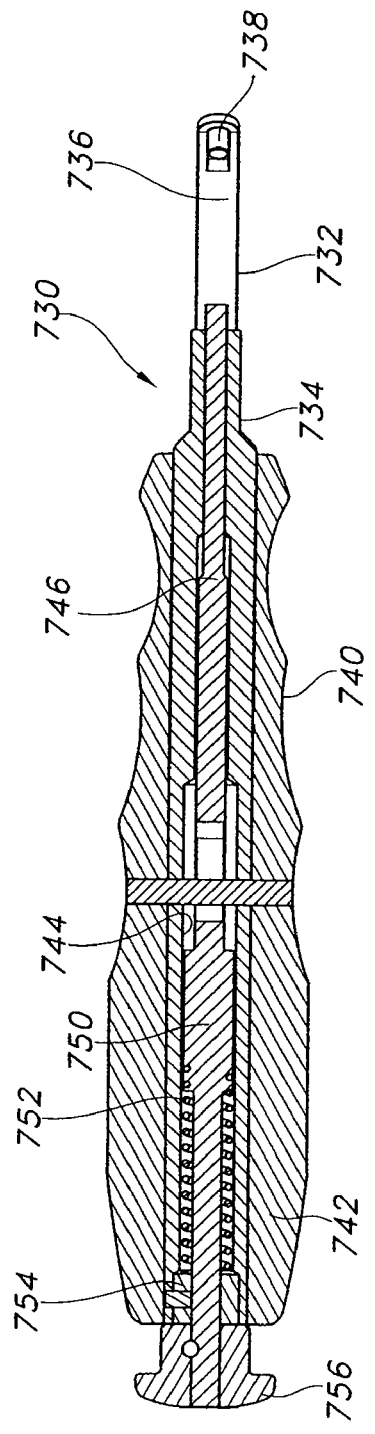
FIG. 40
FIG. 41

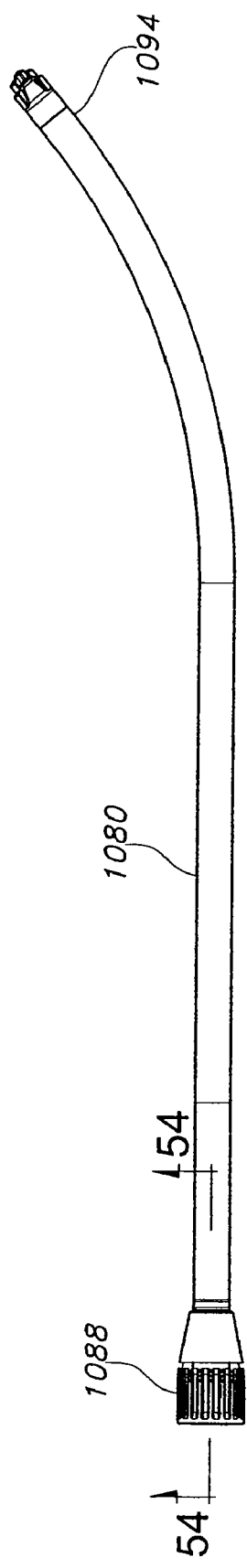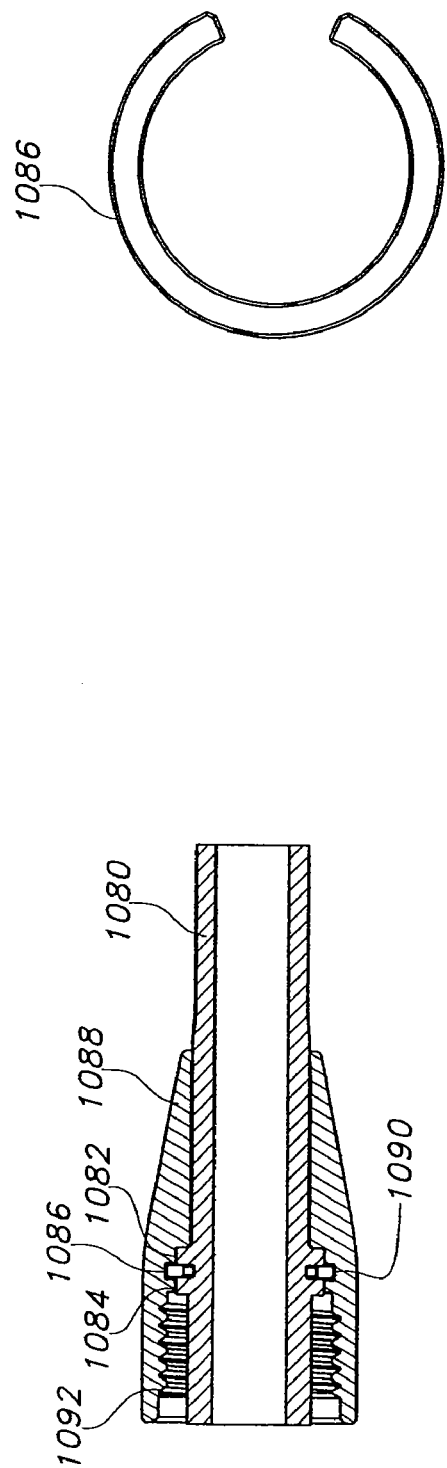
FIG. 53
FIG. 55
FIG. 54

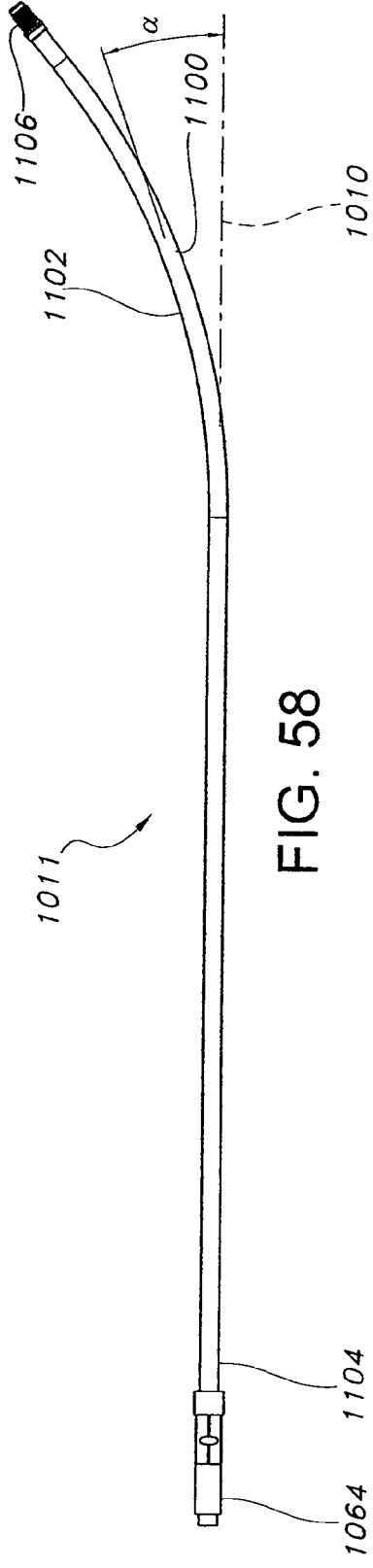
FIG. 58
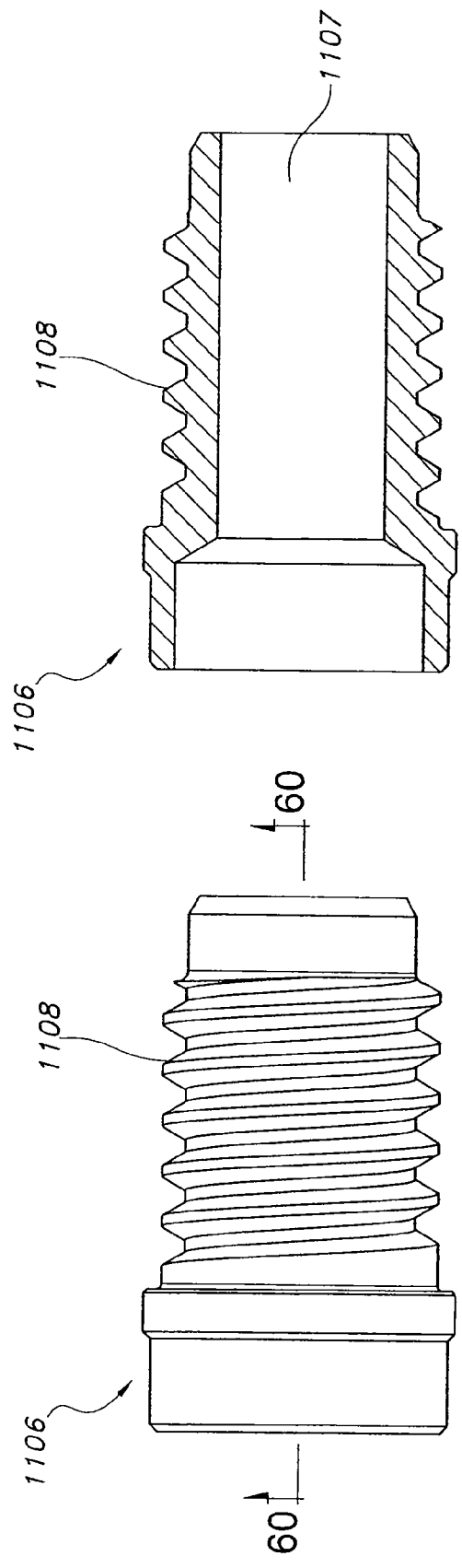
FIG. 60
FIG. 59

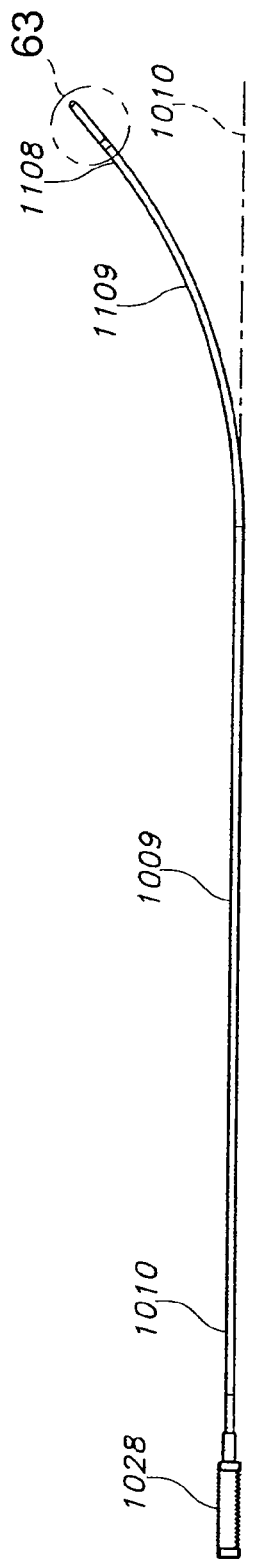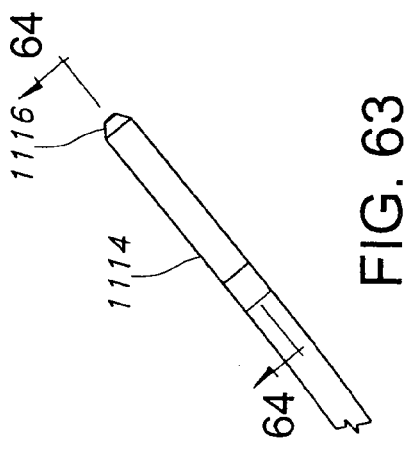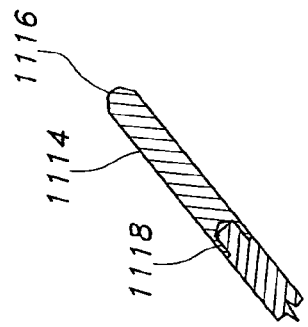
FIG. 61
FIG. 62
FIG. 63
FIG. 64

MINIMALLY INVASIVE SPINAL STABILIZATION SYSTEM

FIELD OF THE INVENTION

The present invention relates generally to surgical implants for stabilizing the spine, and more particularly to a spinal implant system, instrumentation and surgical procedures for inserting and manipulating a spinal implant system in a minimally invasive manner.

BACKGROUND OF THE INVENTION

Spinal surgery on the lumbar and thoracic spines have classically been open operations, meaning that the instrumentation used is placed through an incision that exposes all of the spine to be instrumented, as well as a portion of spine above and below the area to be instrumented due to the need for proper visualization. This extensive exposure disrupts a considerable amount of tissue, particularly the lumbar paraspinal musculature which needs to be stripped off the vertebra bones for exposure. This stripping leads to muscle damage directly caused by either electrical cautery or manual cutting or indirectly by interruption of vascular supply to the muscle due to coagulation or cutting of vessels, and caused also by embarrassment of the vascular supply during the course of surgery due to compression by retractors on the muscle which are required to maintain exposure. In addition, spinal implants can impact upon the facet joints of the spine, particularly the upper most pair of pedicle screws, which can cause pain or dysfunction of the involved joint. This is due in part to the fact that the pedicle screw systems are designed to give stability without being made to respect normal anatomy. In other words, the spine is forced to fit the metal, instead of fitting the metal to the spine.

The present day surgical approach therefore has added to patient morbidity due to the extent of the surgical exposure, tissue damage done primarily to the posterior longitudinal musculature of the spine during the exposure, blood loss and risk of infection. Large open operations also tend to be the cause of significant postoperative pain and disability. Accordingly, these issues lead to longer hospital stays, higher postoperative complications, such as phlebitis and pneumonia brought on by immobility, and greater consumption of postoperative medications with their resultant side effects. In addition, the paraspinal muscle tissue damage has been implicated in the genesis of postoperative lumbar mechanical dysfunction and stiffness leading to postoperative pain syndromes or failed back syndrome. Also, interference by metal implants of the normal function of the rostral facet joints has been implicated in the early degeneration of these joints, as well as pain and disability, all which could lead to other more involved surgeries.

SUMMARY OF THE INVENTION

The foregoing limitations of conventional spinal stabilization instrumentation, implants and procedures are resolved in several respects by minimally invasive systems and methods in accordance with the invention. In a first embodiment of the invention, a spinal stabilization system includes an elongated plate having a side rail and a channel extending adjacent the side rail. A pedicle screw assembly is positioned in the channel in releasable engagement with the side rail. The pedicle screw assembly includes a polyaxial screw having a rounded head and an elongated shank, and a lower screw housing having a lower locking flange and a seat portion. The polyaxial screw extends through the lower screw housing with the rounded head engaging the seat portion. The pedicle screw assembly also includes a lower locking element positioned in the lower screw housing to secure the polyaxial screw head in the lower screw housing, and an upper screw housing having a bore providing access to the lower locking element and the polyaxial screw, the upper screw housing having an upper locking flange. The side rail of the plate is releasably engaged between the upper locking flange and the lower locking flange. An upper locking element couples the upper screw housing to the lower screw housing and secures the rail between the upper locking flange and the lower locking flange.

In a second embodiment of the invention, a pedicle screw assembly includes a polyaxial screw having a rounded head and an elongated shank, and a lower screw housing having a lower locking flange extending radially outwardly. The polyaxial screw extends through the lower screw housing with the rounded head engaging the seat portion. A lower locking element positioned in the lower screw housing secures the polyaxial screw head in the lower screw housing. An upper screw housing includes a bore providing access to the lower locking element and the polyaxial screw, and an upper locking flange extending radially outwardly. An upper locking element couples the upper screw housing to the lower screw housing.

In a third embodiment of the invention, a spinal stabilization plate includes an elongated body having a pair of generally parallel side rails and a channel extending between the side rails. The body further includes a first end having an aperture that connects with the channel by way of a passage through the first end, and a second end opposite the first end. The side rails each include an upper surface with a plurality of clamping recesses and an inner sidewall facing along the channel with a groove extending parallel with the channel.

In a fourth embodiment of the invention, a guidewire insertion kit includes a casing having a proximal end and a distal end, and forming a bore extending from the proximal end to the distal end. The kit also includes a hammer having a bore in which the proximal end of the casing extends, the hammer being slidably displaceable along the casing. A guidewire extends through the bore of the casing.

In a fifth embodiment of the invention, an assembly for orienting a spinal stabilization plate includes an obturator having a probe end with at least one retractable locking tab. The locking tab is displaceable between a locking position, in which the locking tab extends radially outwardly from the probe end, and a release position, in which the locking tab is retracted inside the probe end. A plate reduction sleeve includes a tubular wall and a bore extending along the length of the tubular wall. The obturator extends within the bore of the plate reduction sleeve and slidably engages the tubular wall. The tubular wall includes at least one alignment member that engages the obturator to substantially prevent rotation of the obturator in the plate reduction sleeve.

In a sixth embodiment of the invention, an assembly for introducing a bone screw assembly to a spinal stabilization plate includes a sleeve having a tubular wall and a passage extending along the length of the tubular wall. The tubular wall includes a proximal end having an opening into the passage, and a distal end having a clamping member for detachably engaging a stabilization plate. A screw housing manipulator includes a tubular wall and a bore extending along the length of the tubular wall, the tubular wall having a proximal end having an opening into the bore, and a distal end having a clamping member for detachably engaging a screw assembly. The screw housing manipulator is slidably displaceable and rotatable in the passage of the sleeve. In one embodiment, the screw housing manipulator is rotatable in the passage of the sleeve within a limited range of approximately ninety degrees in one direction.

In a seventh embodiment of the invention, a method for implanting a minimally invasive spinal stabilization plate includes the steps of inserting an elongated plate into a space above a first vertebra and a second vertebra that is being fused to the first vertebra; driving a first screw assembly through a channel extending within the plate and into the first vertebra, the first screw assembly having an on-board locking mechanism; locking the first screw assembly to the plate; driving a second screw assembly through the channel within the plate and into the second vertebra, the second screw assembly having an on-board locking mechanism; locking the second screw assembly to the plate; moving the second screw assembly toward the first screw assembly to apply compression between the first and second vertebrae; and locking down the first screw assembly and the second screw assembly to fix the orientation of the plate.

In an eighth embodiment of the invention, a method for implanting a minimally invasive spinal stabilization plate includes the steps of driving a guidewire into a vertebra; inserting a plate over the vertebra, the plate having a pair of side rails and a channel between the side rails; advancing a first instrument over the guidewire to center the guidewire between the side rails; advancing a second instrument over the guidewire to draw the plate perpendicular to the guidewire; advancing a screw assembly over the guidewire and into the channel, the screw assembly having a housing and a screw that articulates with respect to the housing; driving the screw into the vertebra to fix the screw relative to the vertebra; locking the housing of the screw assembly to the plate; and locking the screw to the housing to fix the housing and plate relative to the vertebra.

In a ninth embodiment of the invention, an instrument for inserting and remotely operating a spinal stabilization system includes an outer shaft having a distal end and a coupling on the distal end for engaging a spinal stabilization plate. An inner shaft is axially displaceable inside the outer shaft. A first driving mechanism engages the outer shaft and operates to attach the outer shaft to a spinal stabilization plate. A second driving mechanism engages the inner shaft and operates to axially advance the inner shaft through the outer shaft.

BRIEF DESCRIPTION OF THE DRAWINGS

The foregoing summary and the following description will be more clearly understood in conjunction with the drawing figures, of which:

FIG. 7 is a perspective view of a plate in accordance with one exemplary embodiment of the invention;

FIG. 8 is a top view of the plate of FIG. 7;

FIG. 9 is a truncated top cross-sectional view of the plate of FIG. 7;

FIG. 10 is a side cross-sectional view of the plate of FIG. 7;

FIG. 11 is a cross-sectional view of the plate of FIG. 7 taken through line 11-11 in FIG. 10;

FIG. 12 is an elevation view of a guidewire insertion assembly in accordance with one exemplary embodiment of the invention;

FIG. 13 is a perspective view of an inserted handle of the guidewire insertion assembly of FIG. 12;

FIG. 14 is an elevation view of a dilator component in accordance with one exemplary embodiment of the invention;

FIG. 15 is a perspective view of another dilator component in accordance with one exemplary embodiment of the invention, which may be integrally formed with or attached to other components;

FIG. 17 is a first side view of an obturator assembly in accordance with one exemplary embodiment of the invention;

FIG. 18 is a second side view of the obturator assembly of FIG. 17;

FIG. 19 is a cross-sectional view of the obturator assembly of FIG. 17, taken through line 19-19 in FIG. 17;

FIG. 23 is a first side view of a plate reduction sleeve assembly in accordance with one exemplary embodiment of the invention;

FIG. 23A is a proximal end view of the plate reduction sleeve assembly of FIG. 23;

FIG. 24 is a second side view of the plate reduction sleeve assembly of FIG. 23;

FIG. 27 is a first side view of an inner shaft of the plate reduction sleeve assembly of FIG. 23;

FIG. 28 is a second side view of an inner shaft of the plate reduction sleeve assembly of FIG. 23;

FIG. 29 is a knob component of the plate reduction sleeve assembly of FIG. 23;

FIG. 30 is a perspective view of a screw housing manipulator assembly in accordance with one exemplary embodiment of the invention;

FIG. 31 is a cross-sectional view of the screw housing manipulator assembly of FIG. 30;

FIG. 32 is a first side view of an inner shaft of the screw housing manipulator assembly of FIG. 30;

FIG. 33 is a second side view of an inner shaft of the screw housing manipulator assembly of FIG. 30;

FIG. 34 is an enlarged cross-sectional view of an end of the inner shaft of the screw housing manipulator assembly of FIG. 30;

FIG. 38 is a perspective view of a sleeve component of a counter-torque kit in accordance with one exemplary embodiment of the invention;

FIG. 39A is a side view of the sleeve of FIG. 38;

FIG. 39B is a side cross-sectional view of the sleeve of FIG. 38, taken through line 39B-39B of FIG. 39A;

FIG. 40 is a side view of a counter-torque handle used in a counter-torque kit in accordance with one exemplary embodiment of the invention;

FIG. 41 is a cross-sectional view of the counter-torque handle of FIG. 40, taken through line 41-41 of FIG. 40;

FIG. 53 is a side elevation view of an inserter shaft of the inserter shown in FIG. 42;

FIG. 54 is a cross-sectional view of a portion of the inserter shaft taken along line 54-54 of FIG. 53;

FIG. 55 is an end view of a retaining ring used in the inserter shaft shown in FIG. 53;

FIG. 58 is a side elevation view of a flexible outer shaft of the inserter shown in FIG. 42;

FIG. 59 is an enlarged view of the distal tip of the outer shaft shown in FIG. 58;

FIG. 60 is a cross-sectional view of the distal tip taken along line 60-60 of FIG. 59;

FIG. 61 is a side elevation view of a flexible inner shaft of the inserter shown in FIG. 42;

FIG. 62 is a side elevation view of the inner shaft of FIG. 61, with proximal and distal ends of the shaft removed;

FIG. 63 is an enlarged view of the distal tip of the inner shaft shown in FIG. 61;

FIG. 64 is a cross-sectional view of the distal tip of the inner shaft shown in FIG. 61 taken along line 64-64 of FIG. 63.

DETAILED DESCRIPTION OF THE INVENTION

Although the invention is illustrated and described herein with reference to specific embodiments, the invention is not intended to be limited to the details shown. Rather, various modifications may be made in the details within the scope and range of equivalents of the claims and without departing from the invention.

The apparatuses and methodology that are used in accordance with the invention provide a muscle sparing technique for stabilizing the spine that minimizes the disruption and damage of tissue. Rather than stripping a large section of tissue from bone to expose the spine, the apparatuses and methods described in accordance with the invention pass percutaneously through a small incision and displace only a small area of tissue. Once the stabilization assembly is properly positioned, the assembly is adjusted through the small incision, requiring minimal disruption of surrounding tissue. The instrumentation provides audible and tactical signals during operation so that the need for direct visualization of the implant is reduced or eliminated. When the need for visualization of the implant below tissue is required, the implant and instrumentation are detectable through lateral imaging techniques, avoiding the need once again to open a large area of tissue. In preferred embodiments, selected portions of the instruments are radiolucent to allow the surgeon to properly visualize and monitor each surgical step. The apparatuses and methodology of the present invention provide minimally invasive techniques in all stages of operation, including spinal access, implant insertion, implant manipulation, spinal compression and final tightening of the implant.

Figure 1:
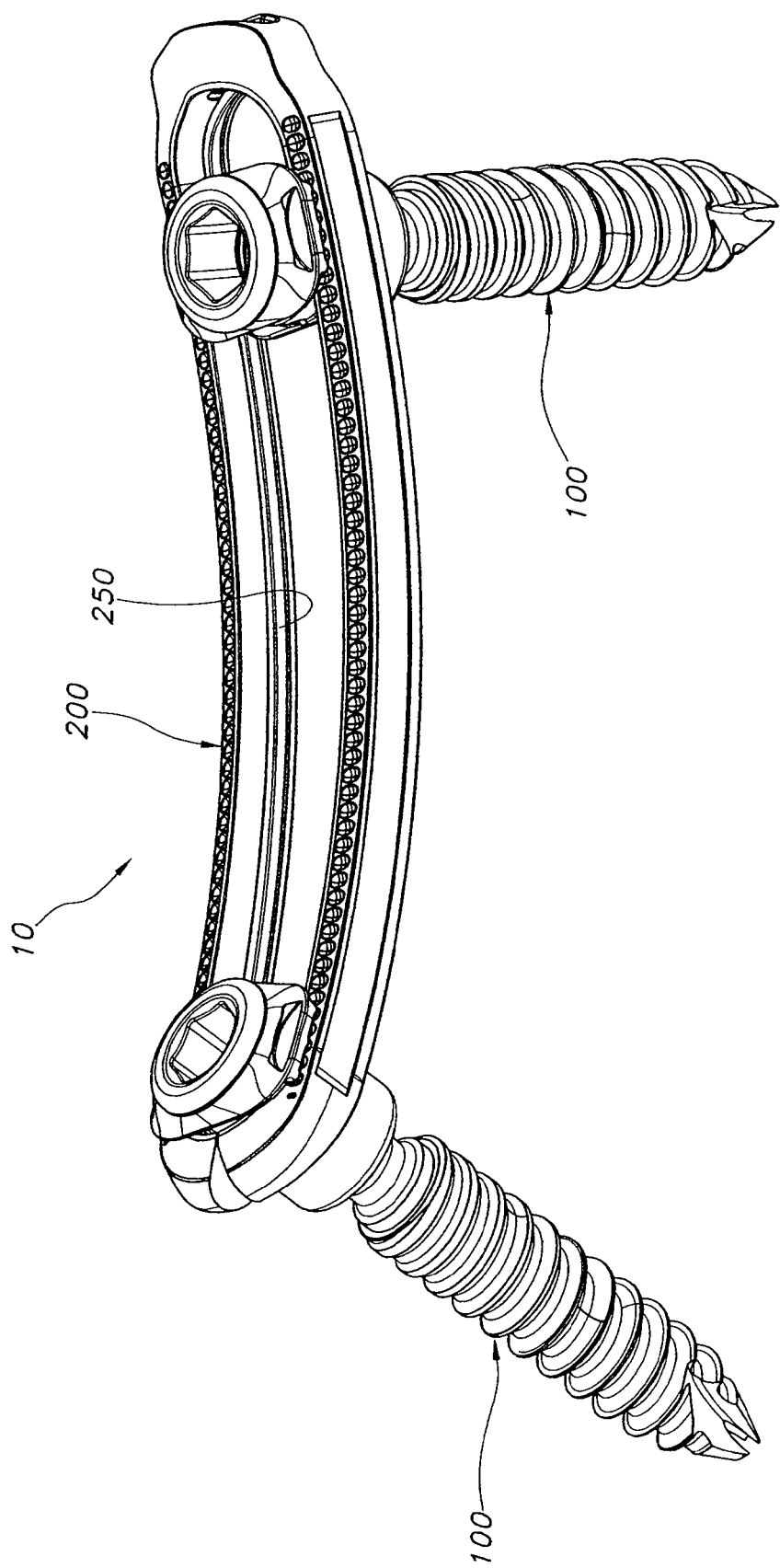
FIG. 1 is a perspective view of a spinal stabilization system in accordance with one exemplary embodiment of the invention.

Referring now to the drawing figures generally, various assemblies and components in accordance with the invention will be described. FIG. 1 illustrates a minimally invasive spinal stabilization system 10 in accordance with one possible embodiment of the invention. Stabilization system 10 can be implanted over two or more vertebral bodies to stabilize them against relative motion. Various implant sizes and configurations are possible, as dictated by the patient's condition, and other factors. System 10, for example, includes two polyaxial pedicle screw assemblies 100 that cooperate with a bone plate 200. Each screw assembly 100 can be inserted through a channel 250 in plate 200 and anchored into a vertebral body. The position of each screw assembly 100 can further be adjusted with respect to the plate, and then tightened to secure the plate to the spine. Each screw assembly 100 contains on-board locking mechanisms to fix the polyaxial screw head in the assembly once the assembly is locked to the plate 200. As will be described, the steps of accessing the spine and positioning and tightening stabilization system 10 require minimal disturbance of tissue and blood vessels around the spine.

Figure 2:
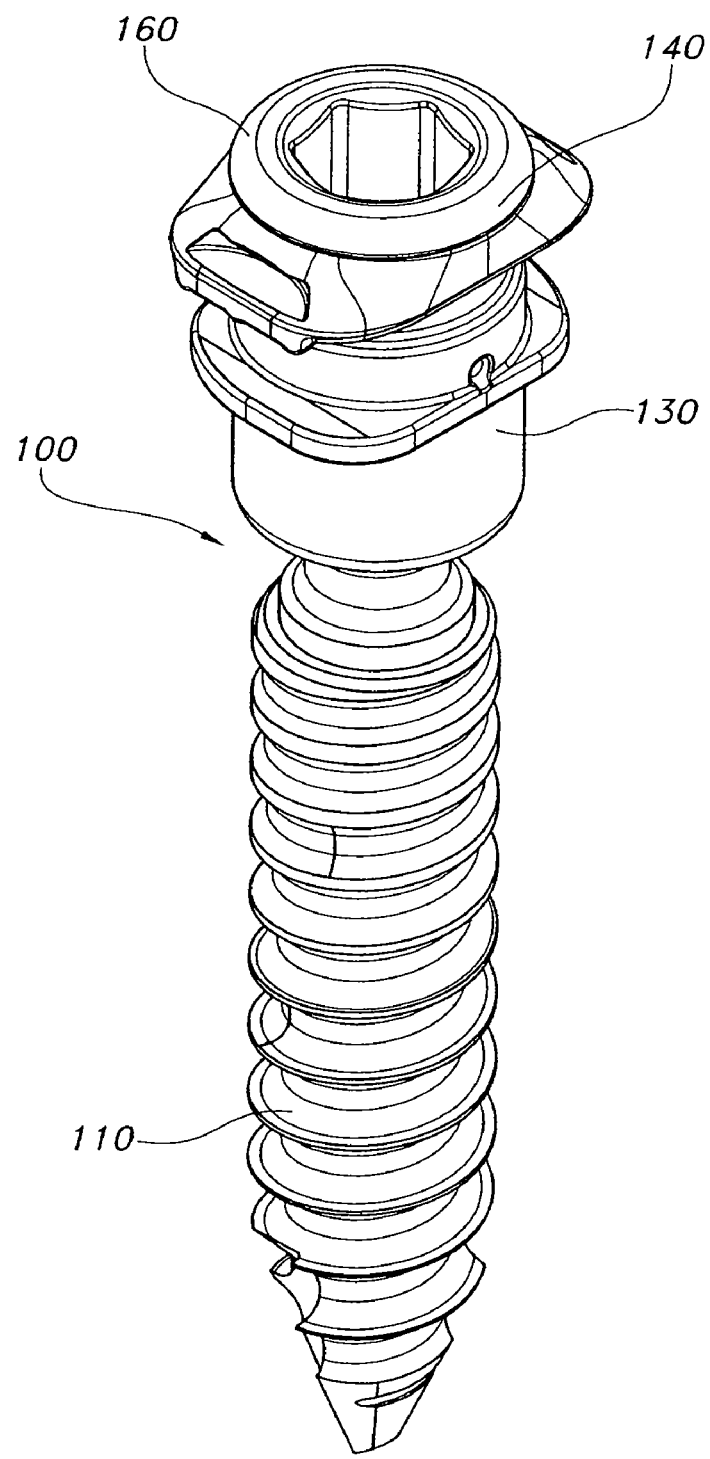
FIG. 2 is a perspective view of a polyaxial screw assembly in accordance with one exemplary embodiment of the invention.
Figure 3:
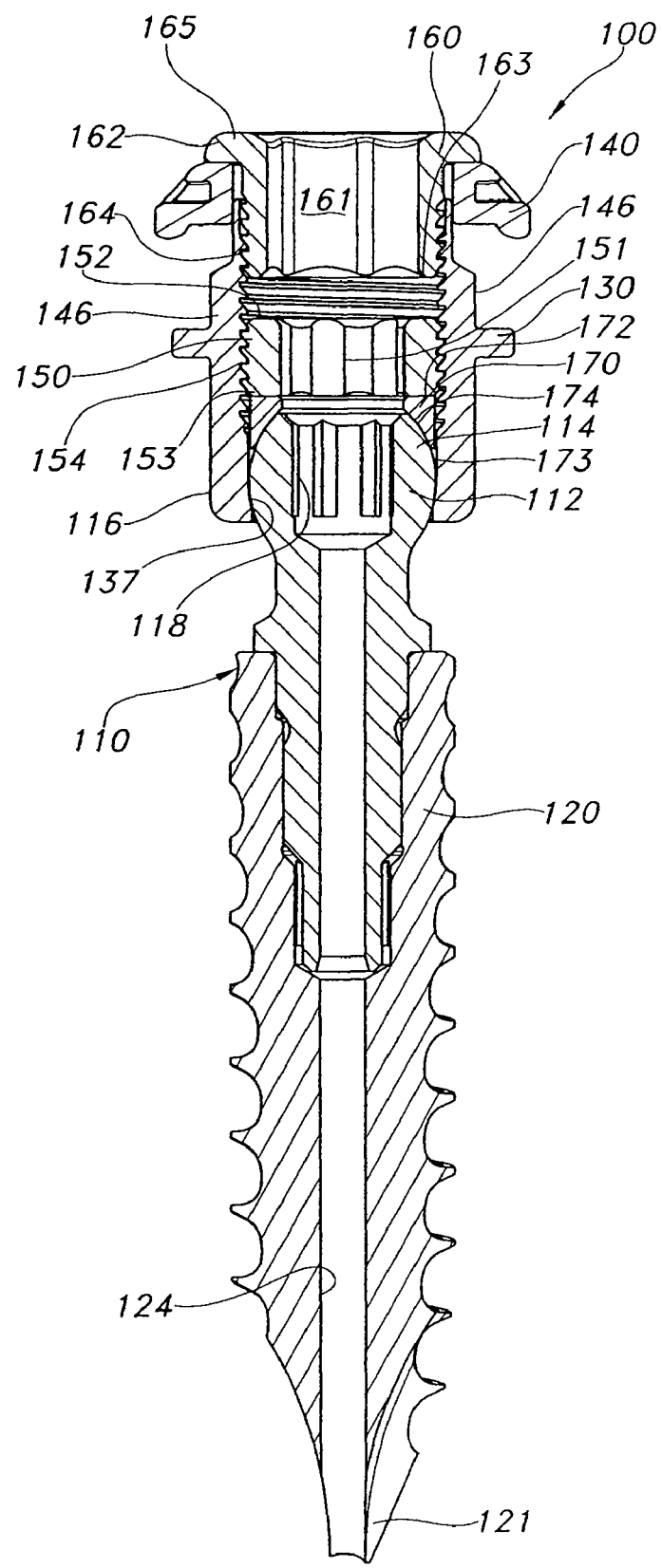
FIG. 3 is a cross-sectional view of the polyaxial screw assembly of FIG. 2.

Referring now to FIGS. 2 and 3, screw assembly 100 includes a polyaxial screw 110 having a head 112 and a shank 120. Screw 110 is cannulated to allow it to be introduced over a surgically placed guidewire. Head 112 and shank 120 are both cannulated, forming a bore 124 that extends the entire length of screw 110. A number of screw configurations may be used in accordance with the invention, including one-piece screws or modular screw assemblies. In screw 110, head 112 is threaded into shank 120, with the head and shank essentially operating as a single integral body. Head 112 includes a rounded portion 114 to allow for polyaxial mobility and engagement with the rest of screw assembly 100. Rounded portion 114 may include contours that are spherical, parabolic, or of a compound curvature. The assemblies of the present invention preferably utilize screws with surfaces that form a strong locking engagement with the rest of the screw assembly in the tightened condition. Rounded portion 114, for example, includes a jagged surface 116 that bites into adjacent surfaces in screw assembly 100 when polyaxial screw 110 is tightened in the assembly.

A number of components within screw assembly 100 have sockets for engagement with insertion tools and driving tools. A variety of standard or customized socket configurations may be used in accordance with the invention. For purposes of this description, hexagonal configurations will be shown and described, with the understanding that other configurations may be used. Screw 110 includes a hexagonal socket 118 in screw head 112. Hexagonal socket 118 cooperates with a hex driver, to tighten screw 110 into a vertebral body. Preferably, socket 118 is centered over and coaxial with bore 124. Shank 120 includes a self-tapping tip 121.

Screw assembly 100 is pre-assembled with multiple housings that facilitate separate locking steps. A lower housing 130 facilitates locking of screw assembly 100 into channel 250 of plate 200, while still allowing translation of the screw assembly along the length of the channel. In one orientation, screw assembly 100 has a range of motion that allows it to both pivot and translate within channel 250. In another orientation within channel 250, screw assembly 100 has a restricted range of motion that only permits it to translate along the length of the channel. As will be described, screw assembly 110 can be translated in channel 250 to apply compression to the vertebral bodies. Once the lower housing 130 is locked, an upper housing 140 is operable to lock the position of screw assembly 100 within channel 250 of plate 200.

Figure 4A:
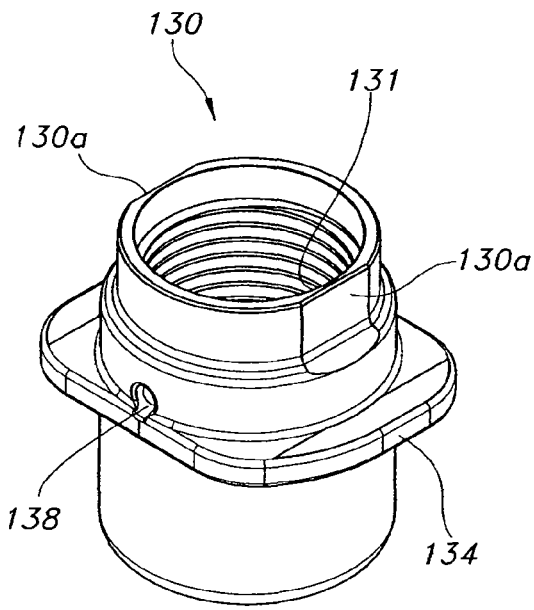
FIG. 4A is a perspective view of a housing component in the polyaxial screw assembly of FIG. 2.
Figure 4B:
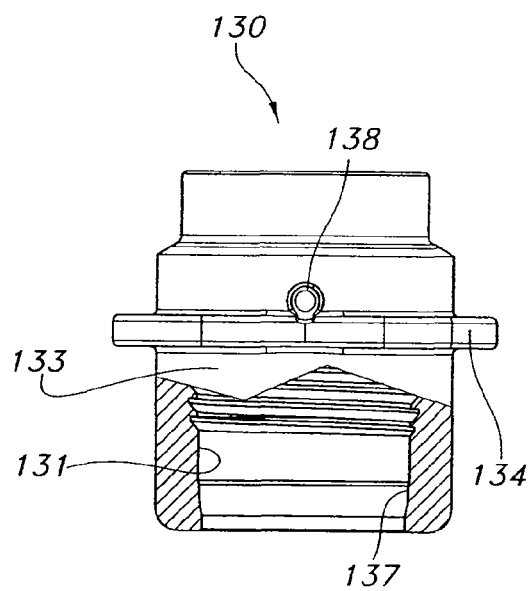
FIG. 4B is an elevation view of the housing component of FIG. 4A, shown in partial cross section.
Figure 5:
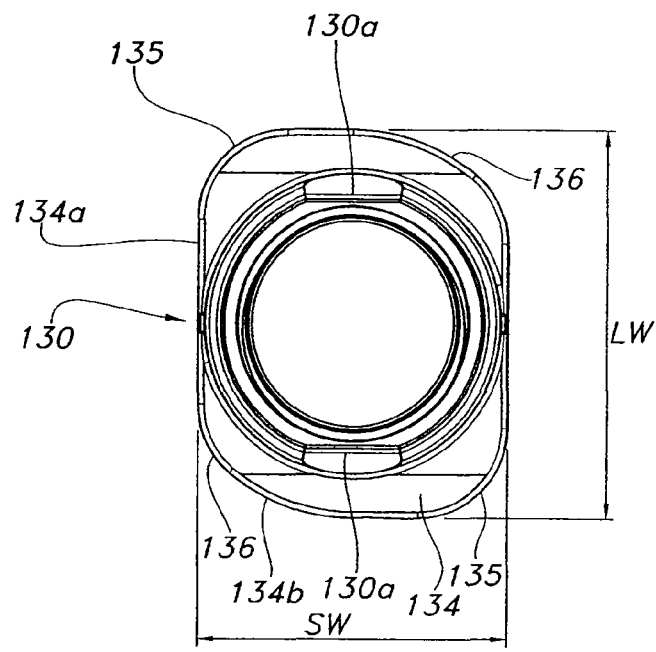
FIG. 5 is a top view of the housing component of FIG. 4A.

Referring now to FIGS. 3-5, lower housing 130 includes a generally cylindrical body having a central bore 131 that extends through the entire length of the lower housing. A proximal end of lower housing 130 has a rounded exterior with opposing flat sides 130a. A distal end of lower housing 130 includes a rounded seat 137 that cooperatively engages the rounded head 112 of polyaxial screw 110. Bore 131 includes an inner thread 133 extending along a section of the bore beginning at the proximal end of lower housing 130 and ending in the area of seat 137.

The exterior of lower housing 130 includes a lower locking flange 134 having a profile that generally forms a parallelogram. The parallelogram has a pair of opposing long sides 134a, having a dimension "LW", and a pair of opposing short sides 134b, having a dimension "SW". One end of each long side 134a intersects a short side 134b at a rounded corner 135 having a relatively small or "sharp" radius of curvature, as seen best in FIG. 5. The remaining end of each long side 134a merges into a rounded corner 136 having a compound curvature with a gradually increasing radius that is larger than the radius of curvature at corners 135.

Referring to FIGS. 4A and 4B, lower housing 130 includes a small conical notch 138 on one side of the housing, just above flange 134. Notch 138 is adapted to connect with an insertion instrument and permit the insertion instrument to manipulate the screw assembly 100. More specifically, notch 138 is configured like a port that allows an insertion instrument to plug into the side of screw assembly 100 and translate the screw assembly along the channel in plate 200, as will be described in more detail below.

Figure 6A:
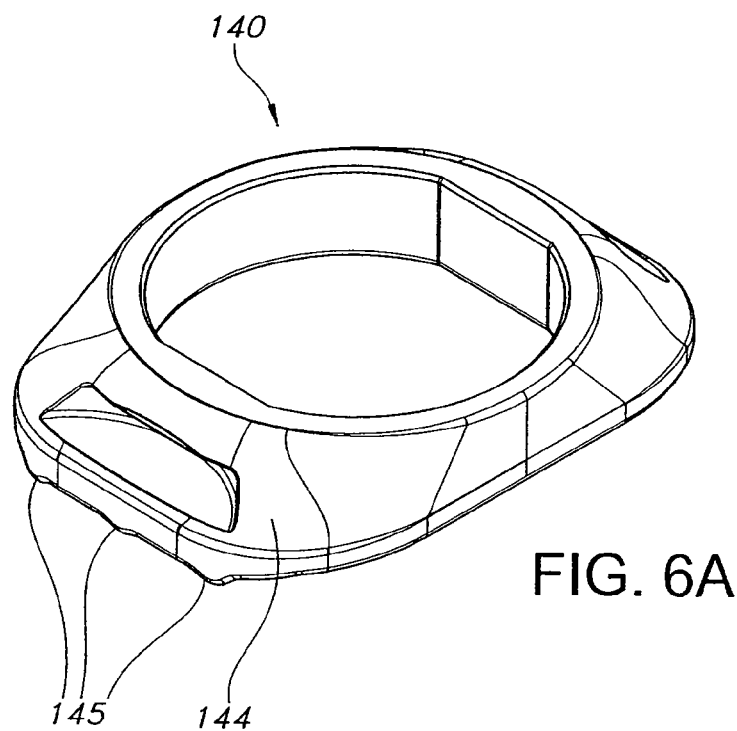
FIG. 6A is a perspective view of another housing component in the polyaxial screw assembly of FIG. 2.
Figure 6B:
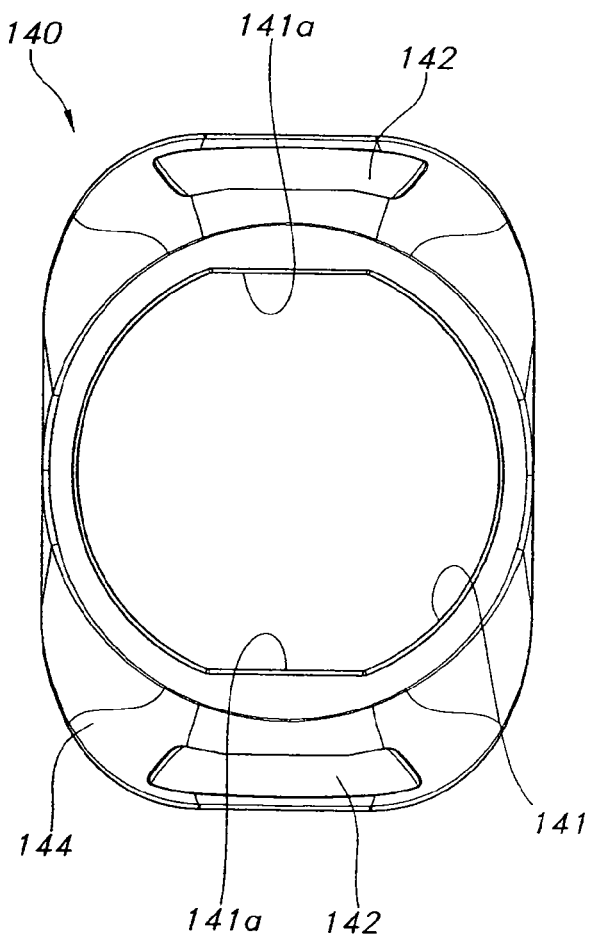
FIG. 6B is a top view of the housing component of FIG. 6A.

Referring now to FIGS. 6A and 6B, upper housing 140 includes a ring-shaped body having a central opening 141. Opening 141 has a generally circular shape with two opposing flat sides 141a, conforming to the external shape of lower housing 130 at its proximal end. In this arrangement, the proximal end of lower housing 130 is configured for insertion through central opening 141 with flat sides 130a aligned with flat sides 141a. Flat sides 130a of lower housing are arranged so as to abut flat sides 141a of central opening 141 to fix the orientation of upper housing relative to lower housing when the two housings are connected.

Upper housing 140 has a pair of wing-like projections forming a generally rectangular upper locking flange 144. Flat sides 130a, 141a of lower and upper housings 130, 140 are arranged such that the long dimension of lower locking flange 134 extends in parallel to the long dimension of upper locking flange 144 when the two housings are connected, as shown in FIG. 2. In the assembled condition, the aligned lower and upper locking flanges 134, 144 form a pair of rail slots 146. Each upper locking flange 144 includes a series of male protrusions, such as small dimples or bosses 145 on the underside of the flange so as to protrude into a rail slot 146 after assembly with lower housing 130. Bosses 145 are incrementally spaced at equal distances in a straight line. In some systems, it may be desirable to arrange the bosses in a curved arrangement to conform to the curvature of the corresponding plate. The spacings and geometry of the bosses are preferably selected to eliminate micro-movement between the upper housing 140 and plate 200.

Screw assembly 100 is pre-assembled with on-board locking mechanisms that avoid the need to introduce separate fasteners during surgery. This eliminates the need to handle, insert and thread separate fasteners into the housings, thereby reducing the number of steps during surgery. A number of on-board locking elements may be employed, such as torque driven set screws. Alternatively, a non-torque driven locking element may be used, such as any of the locking caps described in U.S. patent application Ser. No. 11/753,161, the contents of which are incorporated by reference herein. Referring again to FIG. 3, the on-board locking mechanisms used in screw assembly 110 include a lower locking element 150 and an upper locking element 160. Lower locking element 150 has a generally cylindrical body with a central hex socket 151. The body includes a generally flat proximal end 152 and a generally flat distal end 153. The outer edge of lower locking element 150 includes an external thread 154. Thread 154 meshes with internal thread 133 in lower housing 130, so that the lower locking element can be threaded into bore 131 and axially displaced in the bore in response to rotation. In this arrangement, lower locking element 150 can be driven into bore 131 and tighten polyaxial screw head 112 against seat 137. Screw assemblies used in accordance with the present invention may include optional inserts for enhancing the locking engagement between the screw head and seat. In screw assembly 100, for example, lower housing 130 includes a ring-shaped insert 170 to distribute locking forces more uniformly to the head 112 of polyaxial screw 110. Insert 170 includes a bore 171 that forms a passage between respective sockets of screw head 112 and lower locking element 150. A proximal end 172 of insert 170 engages lower locking element 150, and a distal end 173 of the insert engages polyaxial screw head 112. Distal end 173 has a concave recess 174 that conforms to the geometry of at least a portion of screw head 112, forming a contact interface with a substantial portion of the screw head.

Upper locking element 160 has a generally cylindrical body having a proximal end 162 and a distal end 163. A hex socket 161 extends through upper locking element 160 from the proximal end to the distal end. Proximal end 162 includes a rimmed cap portion 165 that extends radially outwardly with respect to the remainder of upper locking element 160. Upper locking element 160 is configured for insertion through upper housing 140 and into bore 131 of lower housing 130 when the upper and lower housings are assembled. The inner diameter of upper housing 140 is larger than the outer diameter of the distal portion of upper locking element 160, but smaller than the diameter of rimmed cap portion 165. As a result, the smaller diameter portion of upper locking element 160 can pass into upper housing 140, while the rimmed cap portion is stopped at the opening into the upper housing.

An external thread 164 extends along the exterior of upper locking element 160 beneath cap portion 165. External thread 164 meshes with internal thread 133 in lower housing 130, so that upper locking element 160 can be threaded into bore 131 and axially displaced in the bore in response to rotation. In this arrangement, upper locking element 160 can be driven into bore 131, and rimmed portion 165 can be tightened against upper housing 140.

System 10 may include a number of plates having different configurations and contours to conform to different sections of the spine. For example, plates with a linear or flat longitudinal profile may be used. Alternatively, the plate may feature a curved profile, such as a single curvature with one radius, or a compound curvature. System may further include a set of plates, each with a different radius of curvature or compound curvature customized to conform with the spinal curvature at a specific region of the spine. Referring now to FIGS. 7-11, plate 200 includes an elongated body 210. Body 210 has a curvature 211 that generally conforms to the lordotic curvature of the spine. Plate 210 has a proximal end 212 that cooperates with an insertion instrument, and a distal end 218, which is the first section that is inserted into the patient. Proximal end 212 includes an instrument portal 214 that has a relatively large aperture 215 that receives an end of an insertion instrument. Aperture 215 is recessed within a portion of proximal end 212. A small threaded bore 216 connects aperture 215 with the interior channel 250 of plate 210. Portal 214 permits an insertion instrument to engage and manipulate a screw assembly arranged in the plate, as will be described below.

Plate 200 includes a pair of side rails 230 that extend in parallel planes and interconnect the proximal and distal ends 212, 218. Each side rail 230 has an upper surface 232 and a lower surface 234. Upper surfaces 232 each feature an angled locking face 236, as seen best in FIG. 11. Locking faces 236 are pitched outwardly and away from the center of plate 200. Each locking face 236 has a plurality of small round recesses 238 arranged in series. Recesses 238 have dimensions slightly greater than the dimensions of bosses 145 on upper housing 140. In the assembled arrangement, bosses 145 are configured to index with recesses 238 and detachably couple upper locking flanges 144 to side rails 230, as shown in FIG. 2. Recesses 238 are tightly spaced to permit upper locking flanges 144 to attach to plate 200 at several possible locations, and to undergo minor positional adjustments along the length of the plate. Each side rail 230 also has a shallow indentation 260 extending along the exterior of plate 200. Each indentation 260 forms an upper engagement lip 262 and a lower engagement lip 264. As will be described, indentation 260 and engagement lips 262, 264 cooperate with instruments to stabilize the plate against rolling or rotation during surgical procedures.

Channel 250 is bordered by a pair of inner side walls 252 joined by rounded ends 254. Inner side walls 252 are spaced apart by a channel width "W" that is equal to or slightly greater than dimension SW of lower locking flange 134, and smaller than dimension LW of the lower locking flange. As such, channel 250 is adapted to receive lower locking flange 134 by insertion with the lower locking flange oriented with the long sides generally parallel to side rails 230. Each inner side wall 252 has a narrow locking groove 257 extending in the side wall and following the curvature of elongated body 210. Each groove 257 has a height that is slightly greater than the thickness of lower locking flange 134 on lower housing 130. In this configuration, lower locking flange 134 is configured for insertion into locking grooves 257. To insert lower locking flange 134 into grooves 257, the lower locking flange is rotated approximately 90 degrees to pivot short sides 134$b$ into the grooves. The depths of grooves 257 allow the short sides 134$b$ to be rotated so that the short sides are completely received in the grooves and extend parallel to the side rails.

Figure 11A:
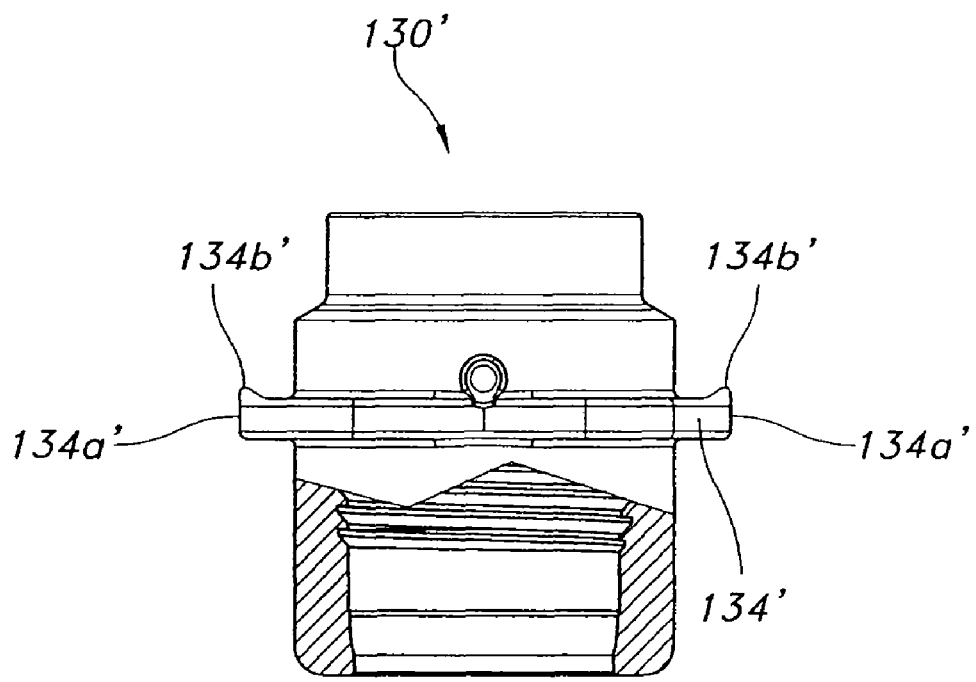
FIG. 11A is an elevation view of a housing component in accordance with an alternate embodiment of the invention, shown in partial cross-section.
Figure 11B:
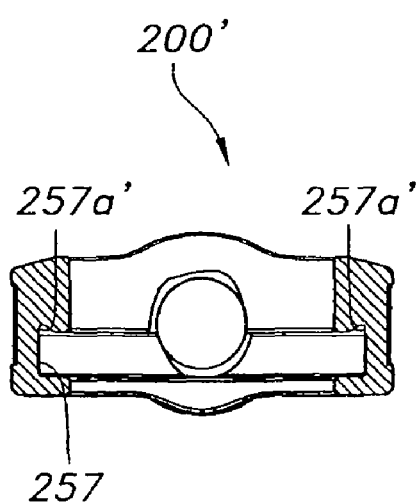
FIG. 11B is a cross-sectional view of a plate in accordance with an alternate embodiment of the invention, shown in cross-section.

Referring to FIGS. 11A and 11B, a lower housing 130' and plate 200' are shown in accordance with alternate embodiments of the invention. Lower housing 130' includes a locking flange 134' with short sides 134$a$' each having a raised projection 134$b$'. Plate 200' has a groove 257' with recesses 257$a$' that conform to the raised projections 134$b$'. In operation, raised projections 134$b$' engage with lateral recesses 257$a$' when lower housing 134' is rotated to the locked orientation to further stabilize the lower housing in groove 257'.

Prior to introducing each screw and plate assembly, the position and angular orientation of each pedicle screw is determined. The pre-determined trajectories of the screw shanks are initially set by guide wires that are driven into the vertebral bodies to mark the positions and angular orientations of each screw shank. Referring now to FIGS. 12 and 13, an exemplary kit 300 for providing minimally invasive guidewire insertion is shown in accordance with the invention. Guidewire insertion kit 300 generally includes an insertion handle 310, a tubular casing 320 and a guidewire 350 which is loaded into the casing. Guidewire insertion kits in accordance with the invention may include one or more tubular sections within the casing. In kit 310, casing 320 includes an upper tube 322 and a lower tube 328. Upper tube 322 and lower tube 328 are interconnected by a threaded engagement and have bores extending along their respective lengths that align coaxially to facilitate insertion of guidewire 350 as shown. Lower tube 328 has a distal end 331 forming a conical taper 332 for percutaneous insertion through tissue. Distal end 331 may have a number of contact surfaces, such as a serrated edge, to engage bone and prevent slippage when casing 320 is in contact with the bone. The bore in lower tube 328 includes a constriction having an inner diameter generally equal to the diameter of guidewire 350 so as to frictionally engage the guidewire. As with other instruments, components of guidewire insertion kit 300 may be formed of radiolucent material so that guidewire placement can be more clearly monitored under imaging.

Insertion handle 310 includes a gripping end 312 for holding the assembled tubes 322, 328 in position, and a holder end 314. Holder end 314 has a tubular ring 315 that is clamped around the upper tube 322. A ball plunger 316 that extends partially within ring 315 provides a frictional coupling between handle 310 and casing 320. A generally cylindrical slide hammer 326 is slidably displaceable around upper tube 322. A blind bore extends through a bottom end of slide hammer 326 and terminates inside a mid-region of the slide hammer. In operation, slide hammer 326 is lifted upwardly or proximally along the upper tube and released. The slide hammer 326 falls by gravity until the end of the blind bore in the slide hammer contacts the proximal end of the upper tube 322. The lifting and dropping is done repeatedly to gradually drive guidewire 350 into the vertebral body. The position and orientation of guidewire 350 may be monitored as it is driven into the bone using a number of imaging techniques. The upper and lower tubes 322, 328 are configured for removal from guidewire 350 once the guidewire position is set. Preferably, guidewire 350 is slightly longer than casing 320.

The tissue immediately surrounding the inserted guidewires 350 may be dilated using a number of different dilation tools. FIGS. 14 and 15 illustrate an exemplary dilator sleeve 400 and dilator tip 410. Dilator sleeve 400 and tip 410 may be advanced over a guidewire 350 and driven into the tissue surrounding the guidewire to dilate the tissue. In a preferred embodiment, dilator sleeve 400 and tip 410 are configured to be advanced over casing 320 of the guidewire insertion kit, so that the casing does not have to be removed prior to dilation. A variety of tissue dilation components may be used in accordance with the invention, including components that are interchangeable or otherwise compatible with the guidewire insertion kit 300.

Referring back to FIGS. 7 and 8, plate 200 is configured to be inserted through tissue and positioned around guidewires 350 after the guidewires are set. Percutaneous insertion of plate 200 is done in a minimally invasive manner that minimizes the trauma to the tissue and blood vessels. This is facilitated in part by body 210, which has a relatively small thickness and width, forming a smooth narrow profile. Distal end 218 of plate 200 has a rounded nose portion 220 that smoothly navigates through tissue during insertion. Nose portion 220 has a split 222 that extends from the outer perimeter of body into channel 250. An outer portion of split 222 opens out into V-shaped notch 224. Split 222 and V-notch 224 allow plate 200 to be passed over each guidewire. V-shaped notch 224 is adapted to capture each guidewire and draw the guidewire inwardly toward the center of split 222. The width of split 222 is preferably slightly smaller than the diameter of guidewire 350 so that the guidewire abuts the nose portion at the location of the split. The relatively long dimension of plate body 210, and the relatively narrow profile of side rails 230 allow the nose portion to flex apart at the split in response to contact with guidewire 350. In this arrangement, guidewire 350 can be wedged through split 222 and enter channel 250 when plate 200 is driven against the guidewire. Nose portion 220 is resiliently flexible, allowing the nose portion to snap over the guidewire and close the split once the guidewire passes into channel 250. The abutment between guidewire 350 and nose portion 220, followed by the opening of the nose portion at split 222 and passage of the guidewire through the split, are associated with different levels of resistance that offer a tactical aid to the surgeon during positioning of the plate. Specifically, the resistance presented by plate 200 against passage of each guidewire 350, and the subsequent release of each guidewire from split 222 into channel 250, are sensed by the surgeon through inserter instrument to alert the surgeon that each guidewire has successfully entered the plate channel.

Figure 16:
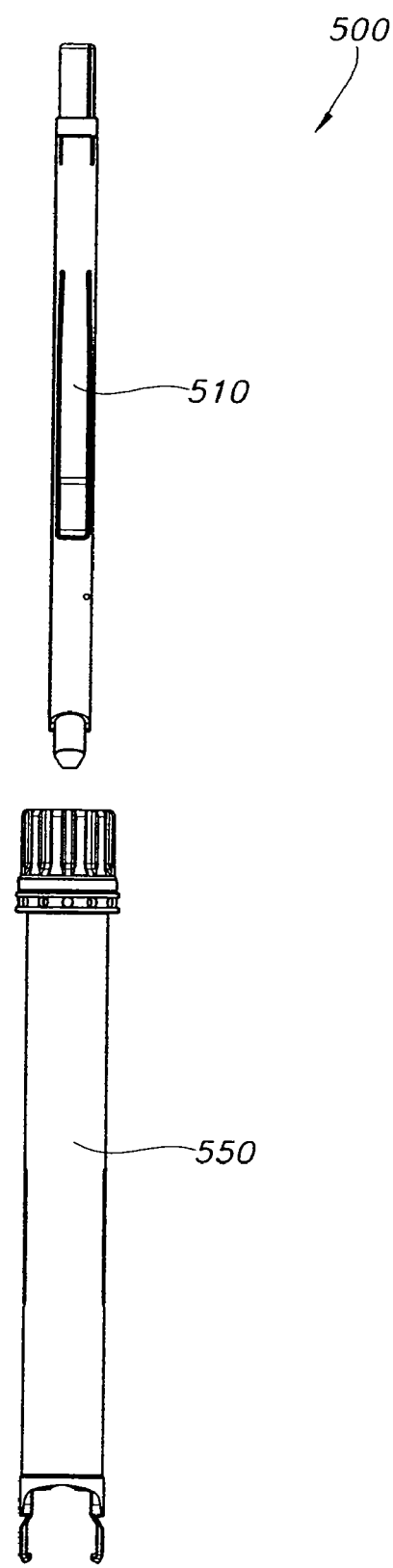
FIG. 16 is an exploded elevation view of a plate orientation assembly in accordance with one exemplary embodiment of the invention.

Referring now to FIG. 16, an exemplary plate orientation assembly 500 is shown in accordance with one embodiment of the invention. Plate orientation assembly 500 includes components that cooperate with one another to properly orient plate 200 with respect to guidewires 350 and the intended screw orientations. The term "plate orientation" broadly encompasses a number of positional adjustments of the plate. These adjustments include centering plate 200 with respect to each guidewire 350 so that the guidewire intersects a centerline passing through the long axis of the plate (hereinafter, "plate centering"). In addition, proper orientation of plate 200 includes canting or tilting the plate so that the plane of the guidewire 350 is generally parallel to the sidewalls of the channel 250 (hereinafter, "plate angling"). For purposes of this description, the process of drawing the plate into a perpendicular relationship with the each screw assembly will be treated as a separate step referred to as "plate reduction."

Plate orientation assembly 500 includes two primary instruments: an obturator 510 and a plate reduction sleeve 550. Obturator 510 is configured for insertion into a bore extending through plate reduction sleeve 550, and operates as a unit with the plate reduction sleeve during plate orientation. Obturator 510 is used for plate centering and plate angling. Plate reduction sleeve 550, as the name implies, is used for plate reduction. By achieving plate centering and plate angling, obturator 510 prepares plate 200 for engagement with plate reduction sleeve 550. Although obturator 510 and plate reduction sleeve 550 cooperate and function together during plate orientation, each component can also operate on its own, and can be used for purposes other than plate orientation. For example, plate reduction sleeve also functions without obturator as a surgical portal and counter-torque applicator during insertion of the screw assembly, as will be described in subsequent sections.

Figure 20:
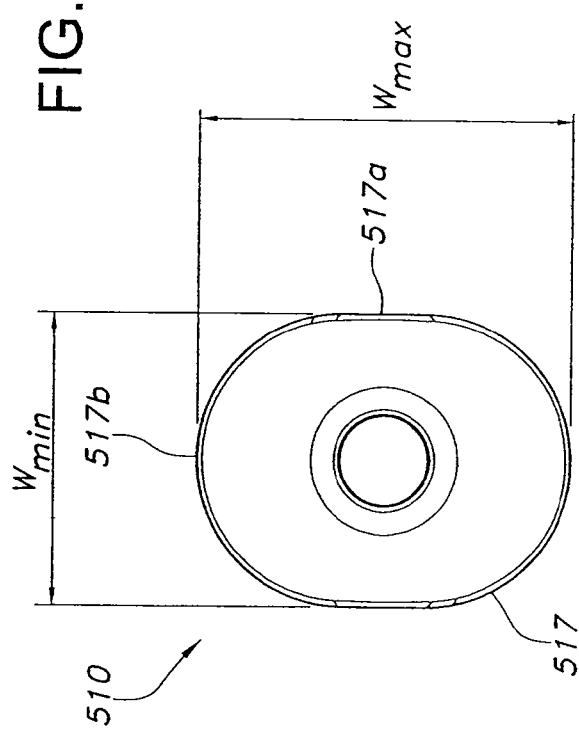
FIG. 20 is an end view of one component of the obturator assembly shown in FIG. 17.

Referring now to FIGS. 17-22, obturator 510 will be described in additional detail. Obturator 510 includes a hollow cylindrical body 512 and a rounded probe end or tip 516 that projects from the distal end of body 512. Obturator tip 516 has a straight section 517 and a tapered end 518. Tapered end 518 is narrow enough to be inserted into channel 250 of plate 200 at any orientation. Straight section 517, however, has a cross-sectional profile that can only be inserted into channel 250 in certain specific orientations. Straight section 517 has a rounded cross section with opposing flat sides 517a and rounded ends 517b, as shown in FIG. 20. The minimum width of straight section 517 is "$W_{min}$", extending between flat sides 517a. The maximum width of straight section 517 is "$W_{max}$", extending between rounded ends 517b and perpendicular to $W_{min}$. $W_{min}$ is more or less equal to the width of channel 250, and increases around the perimeter of straight section 517. In this arrangement, straight section 517 can only enter and pass through channel 250 with flat sides 517a aligned parallel to side walls 256 of the channel. Sidewalls 256 are adapted to engage flat sides 517a and substantially prevent rotation of tip 516 in channel 250. Obturator tip 516 is permitted to translate and tilt within channel 250, in a plane parallel to the sidewalls of the channel.

Obturator 510 includes a locking mechanism to detachably connect orientation assembly 500 with plate 200. A number of locking mechanisms can be used in accordance with the invention. Referring to FIG. 19, the locking mechanism includes a pair of resilient locking springs 536. Locking springs 536 are radially displaceable between a retracted condition, in which the locking springs are positioned within obturator tip 516, and an expanded condition, in which the locking springs project radially outside of the obturator tip. Each locking spring 536 includes a spring tab 538 that extends radially outwardly from the locking spring. Obturator tip 516 includes a pair of diametrically opposed tab slots 520 that are radially and axially aligned with locking springs 536 to allow the locking springs, or at least spring tabs 538, to project outwardly through the slots. In the expanded condition, the axial distance between each spring tab 538 and the distal end of body 512, as shown for example in FIG. 19, is generally equal to or slightly larger than the height of plate 200 (i.e. the dimension between the upper and lower surface of plate 200).

Figure 21:
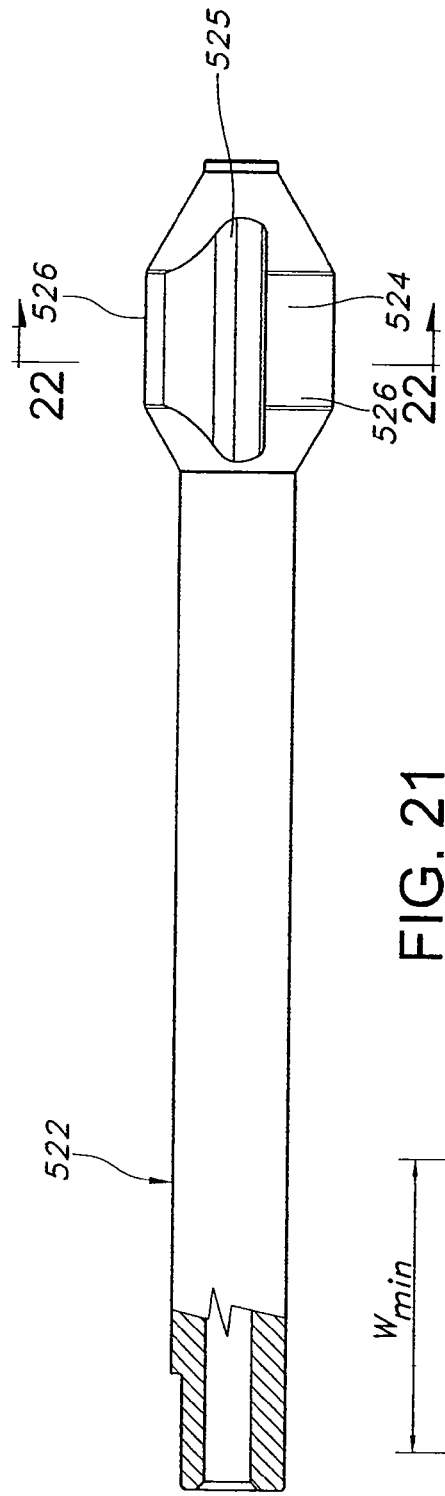
FIG. 21 is an enlarged side view of an inner shaft of the obturator assembly of FIG. 17, shown in partial cross section.
Figure 22:
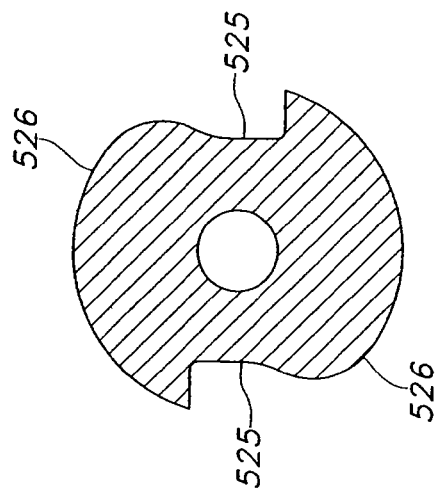
FIG. 22 is a cross-sectional end view of the inner shaft of FIG. 21 taken through line 22-22 of FIG. 21.

In the relaxed condition, locking springs 536 are in the retracted position, with spring tabs 538 recessed in the interior of obturator tip 516. Locking springs 536 are displaceable from the retracted position to the expanded condition in response to rotation of an inner shaft 522 extending within obturator tip 516. Inner shaft 522 has a cam end 524 which is operable to move locking springs 536 between the retracted and expanded conditions. Referring to FIGS. 21 and 22, cam end 524 has a pair of opposing indents 525 and a pair of opposing lobes 526 offset from the indents by 90 degrees. Indents 525 are adapted to receive locking springs 536 in the retracted condition. In contrast, lobes 526 are configured to push locking springs 536 radially outwardly to the expanded position upon rotation of cam end 524. In this arrangement, locking springs 536 can be toggled between the expanded condition and retracted condition in response to rotation of inner shaft 522 and cam end 524. Inner shaft 522 is connected to a plunger 527 that extends to the proximal end of obturator 510. At the proximal end of obturator 510, plunger 527 is press fitted into a control knob 532. Control knob 532 is rotatable relative to obturator body 512. In this configuration, cam end 524 can rotate in response to rotation of control knob 532 to move the locking springs 536 between the retracted condition and the expanded condition.

The axial position of obturator tip 516 relative to body 512 is separately controlled by a body cap 528. Body cap 528 is coupled to control knob 532 by a C-ring 531 or similar coupling. The outer circumference of body cap 528 has an external thread 530 that engages an inner thread 513 inside obturator body 512. In this arrangement, body cap 528 is rotatable along the threaded engagement to axially displace control knob 532, plunger 527, inner shaft 522 and obturator tip 516 relative to body 512. C-ring 531 allows body cap 528 to rotate independently from control knob 532, and limits the transfer of torque from the body cap to the control knob and plunger 527.

In the preferred embodiment, the obturator includes markings or indicia to provide a visual indication of whether the spring tabs are in the retracted or "unlocked" condition, or in the expanded or "locked" condition. In FIGS. 17 and 18, for example, body 512 includes a first indicia 512*a* in the form of a line and a second indicia 512*b* in the form of a line, the second indicia being generally parallel to and angularly offset from the first indicia. Control knob 532 has a third indicia 532*a* that can be rotated into alignment with one of the first and second indicia 512*a*, 512*b*. When third indicia 532*a* is aligned with first indicia 512*a*, cam end 524 is oriented so that spring tabs 538 are retracted into obturator tip 516. When third indicia 532*a* is aligned with second indicia 512*b*, cam end 524 is oriented so that spring tabs 538 are expanded outwardly through slots 520. In this arrangement, alignment with first indicia 512*a* is indicative of an unlocked mode, and alignment with second indicia 512*b* is indicative of a locked mode.

Control knob 532, plunger 527, inner shaft 522 and obturator tip 516 are cannulated and have bores that align coaxially or substantially coaxially with the longitudinal axis of obturator body 512. The bores collectively form a passage for a guidewire, such as guidewire 350. Obturator 510 is configured to be advanced over an implanted guidewire 350 and into channel 250 of plate. As will be explained below, obturator 510 is operable to properly orient plate 200 relative to each guidewire 350 prior to introducing screw assemblies 100 into the plate. Although plate 200 is properly centered and parallel with respect to each guidewire 350, the guidewire may not extend normal to the plate. As a result, a screw assembly 110 that is advanced down guidewire 350 into channel 250 may not enter the channel with upper and lower locking flanges oriented in the proper planes to engage the plate. In such a case, lower locking flange 134 will enter channel 250 in a plane that is non-parallel to the adjacent grooves 257 in sidewalls 256. To correct for the misalignment, orientation assembly 500 is operable to reduce or draw plate 200 into proper alignment with the guidewire orientation prior to introducing a screw assembly. This alignment of plate 200 is accomplished with plate reduction sleeve 550.

Referring now to FIGS. 23-27, plate reduction sleeve 550 will be described in more detail. Among other functions, plate reduction sleeve 550 is operable to reduce or draw plate 200 into a position that is normal to the centered guidewire 350, and retain the plate in that position. With the guidewire 350 centered in channel 250 and retained normal to plate 200, a screw assembly 100 can be properly locked into plate 200. Plate reduction sleeve 550 includes a generally cylindrical outer shaft 552 and a generally cylindrical inner shaft 570 extending within the outer shaft. Inner shaft 570 is interconnected to outer shaft 552 by an adjustment knob 590 attached at the proximal ends of the inner and outer shafts. As will be discussed, inner shaft 570 is axially displaceable within outer shaft 552, but can not rotate relative to the outer shaft.

Figure 25:
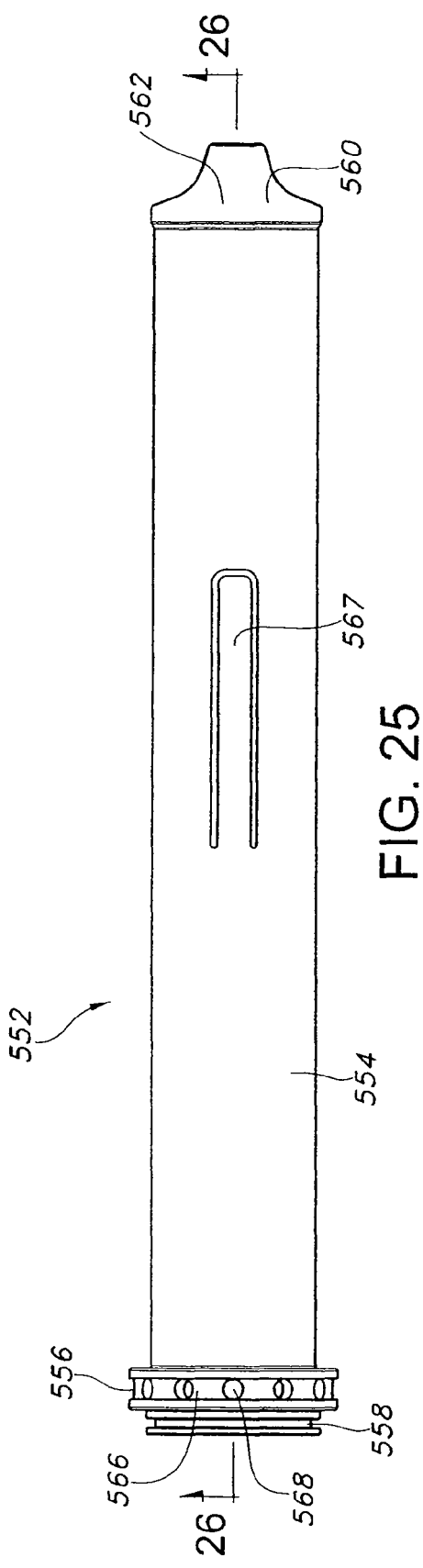
FIG. 25 is a side view of an outer shaft of the plate reduction sleeve assembly of FIG. 23.
Figure 26:
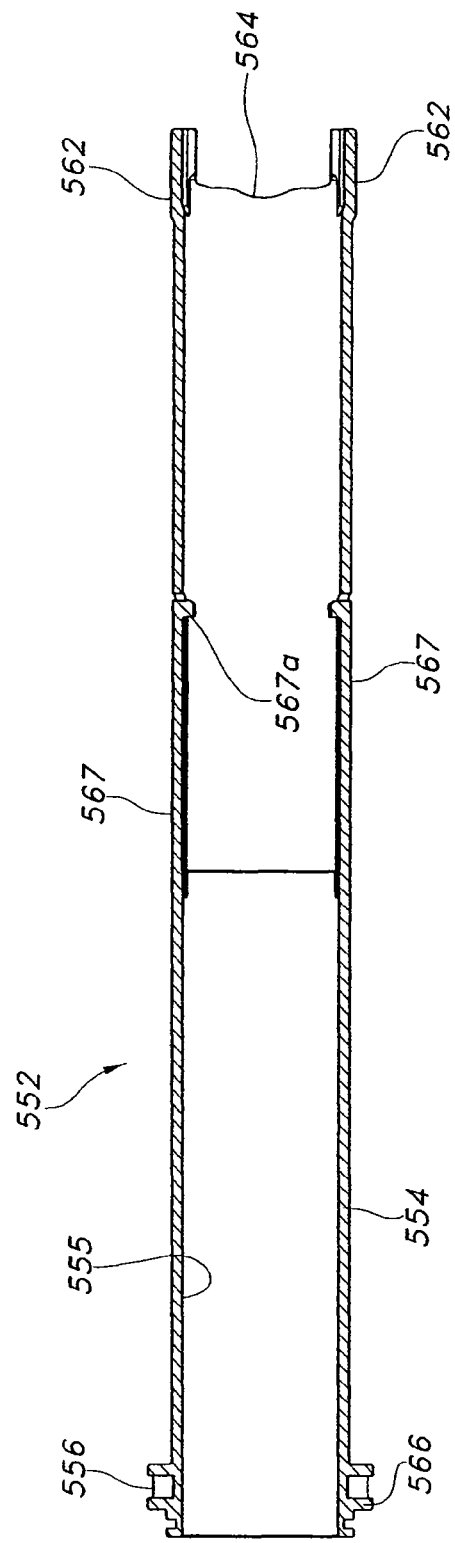
FIG. 26 is a side cross-sectional view of the outer shaft of FIG. 25, taken through line 26-26 in FIG. 25.

Outer shaft 552 includes a hollow body 554 forming a bore 555, as shown in FIGS. 25 and 26. Body 554 includes a pair of diametrically opposed guide arms 567 that are cut out from the sidewall of bore 555. Each guide arm 567 includes a tab 567*a* that extends radially inwardly into bore 555 of outer shaft 552. Guide arms 567 are resiliently flexible. In a relaxed condition, guide arms 567 extend along body 554 with tabs 567*a* projecting radially inwardly inside bore 555. A proximal end 556 of outer shaft 552 includes a locking ring 558 for retaining adjustment knob 590 in a rotatable coupling. Proximal end 556 also includes an engagement surface 566 for instrumentation, such as for example, a counter torque instrument. A distal end 560 of outer shaft 552 includes a pair of distal extensions 562. Distal extensions 562 form a pair of arcuate notches in body 554 that collectively form a plate socket 564. Preferably, the notches forming plate socket 564 have a geometry that conforms with the shape of the upper surface of plate 200.

Referring now to FIGS. 27 and 28, inner shaft 570 includes a hollow body 571 configured for insertion into bore 555 of outer shaft 552. Body 571 includes a pair of diametrically opposed guide slots 580. Guide slots 580 are axially positioned to align with guide arms 567 in outer shaft 552 when inner shaft 570 is inserted into outer shaft. Tabs 567*a* extend a sufficient distance within bore 555 so as to engage the exterior of inner shaft 570 as the inner shaft is inserted into outer shaft 552. Guide arms 567 have sufficient flexibility to bend outwardly from the wall of outer shaft 552. In this arrangement, engagement of tabs 567*a* with the outer wall of inner shaft 552 displaces guide arms 567 radially outwardly until guide slots 580 align with the tabs. Upon alignment with guide slots 580, the deflected guide arms 567 snap inwardly such that guide tabs 567*a* enter the slots 580 to connect the inner and outer shafts together. Tabs 567*a* are confined within slots 580 and are permitted to move axially relative to inner shaft 570. The sidewalls of slots 580 engage with the tabs to prevent rotation of inner shaft 570 relative to outer shaft 552.

Inner shaft 570 is axially displaced within outer shaft 552 by adjustment knob 590. Referring to FIG. 29, adjustment knob 590 includes an inner thread 592 that engages an external thread 574 on proximal end 573 of inner shaft 570 when plate reduction sleeve 550 is assembled. Adjustment knob 590 also includes a rim 594 that cooperatively engages locking ring 558 on a proximal end 556 of outer shaft 552. Rim 594 slidably engages locking ring 558 to allow rotation of knob 590 relative to outer and inner shafts 552, 570. The walls in locking ring 558 substantially limit axial movement of knob 590 relative to outer shaft 552, however. In this arrangement, adjustment knob 590 and outer shaft 552 are axially displaceable in unison relative to inner shaft 570 when the knob is rotated along the threaded engagement between the knob and inner shaft.

A distal portion of inner shaft 570 includes pair of diametrically opposed flex arms 577. Each flex arm 577 includes a clamping member 578 that extends radially outwardly from the rest of the flex arm, as shown in FIG. 28. Clamping members 578 are arranged on the circumference of inner shaft 570 so as to radially align with distal extensions 562 on outer shaft 552 when the inner shaft is inserted into the outer shaft. The cross sectional width of inner shaft 570 at clamping members 578 is larger than the inner diameter of bore 555 between distal extensions 562 of outer shaft 552. Flex arms 577 and clamping members 578 are axially displaceable relative to outer shaft 552 in response to rotation of adjustment knob 590. In particular, clamping members 578 are displaceable between a clamping mode, in which the clamping members are drawn into outer shaft 552, and a release mode, in which the clamping members extend more outwardly from the outer shaft. Clamping members 578 are configured to deflect radially inwardly toward one another with minimal resistance upon being moved to the clamping mode in outer shaft 552. Each clamping member 578 includes a small ramp portion 578a forming a camming surface that contacts the distal end of outer shaft 552 during retraction of the clamping members into the outer shaft. Ramp portions 578a are pitched so as to direct radially inward components of force on clamping members 578 during retraction into outer shaft 552. Each clamping member further includes an inwardly extending detent 580 and an inner gripping surface 582. As will be discussed, detents 580 and inner gripping surfaces 582 are configured to engage side rails 230 of plate 200 to facilitate reduction of the plate.

Proximal end 573 of inner shaft 570 includes a pair of diametrically opposed indexing slots 584 that cooperate with alignment mechanisms on other instruments inserted into plate reduction sleeve 550. Indexing slots 584 permit insertion of certain instruments in certain orientations so as to maintain proper alignment between the inserted instruments, the plate 200 and the screw assembly 100. Indexing slots 584 may be used to align a number of instruments, including components of a counter-torque kit which will be described in more detail below.

Obturator 510 and plate reduction sleeve 550 are interconnected and indexed with one another in a releasable engagement. Obturator body 512 includes a pair of resilient indexing detents 514 with detent ends 514a that project radially outwardly from the detents. Inner shaft 570 of plate reduction sleeve 550 has a corresponding pair of slots 579 that are aligned with detents 514 on obturator body 512 when obturator 510 is inserted into plate reduction sleeve 550. Upon insertion of obturator 510 into plate reduction sleeve and alignment of detents 514 with slots 579, detent ends 514a snap into the slots, producing an audible click that indicates that the components of plate orientation assembly 500 are assembled. The assembled plate orientation assembly 500 can then be advanced over a guidewire 350 to begin plate orientation. The different steps of plate orientation will be described in more detail in the sections focusing on the operation of the assembly 10.

Referring now to FIGS. 30 and 31, a screw housing manipulator 600 is shown in accordance with one exemplary embodiment of the present invention. Screw housing manipulator 600 works as a carrier for screw assemblies 100. In particular, screw housing manipulator 600 can be loaded with a screw assembly 100 during preparation for surgery, and subsequently advanced over a guidewire 350 through a plate reduction sleeve 550 to introduce the screw assembly into a plate 200. Screw housing manipulator 600 includes an inner shaft 610 that is telescopically inserted in an outer shaft 640. A handle 616 is connected to a proximal end 612 of inner shaft 610. Inner shaft 610, which is shown in more detail in FIGS. 32-34, includes a distal end 614 with a pair of diametrically opposed flexible arms 620. Each flexible arm 620 has a clamping extension 622 that extends distally from the flexible arm and serves as a gripping element for engaging a screw assembly 100. Handle 616 is operable to rotate and lock a screw assembly 100 into a plate 200, as will be discussed in more detail.

Figure 35:
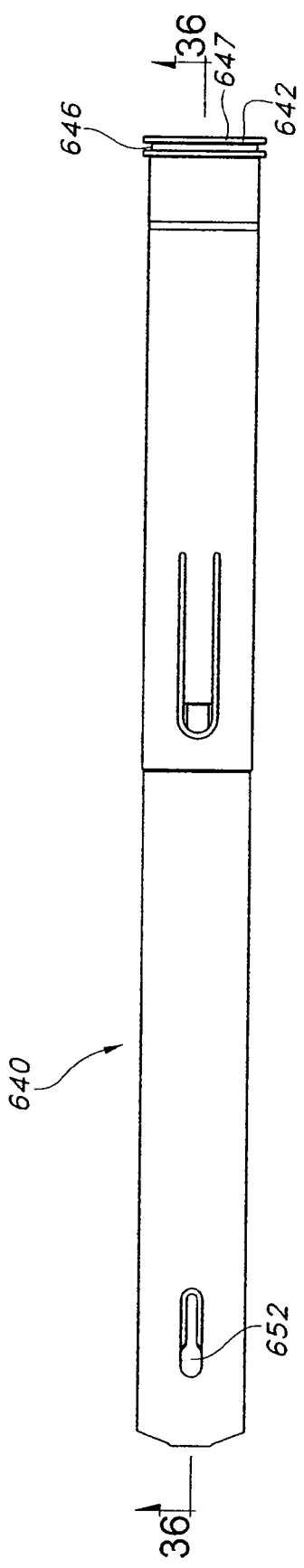
FIG. 35 is a side view of an outer shaft of the screw housing manipulator assembly of FIG. 30.
Figure 36:
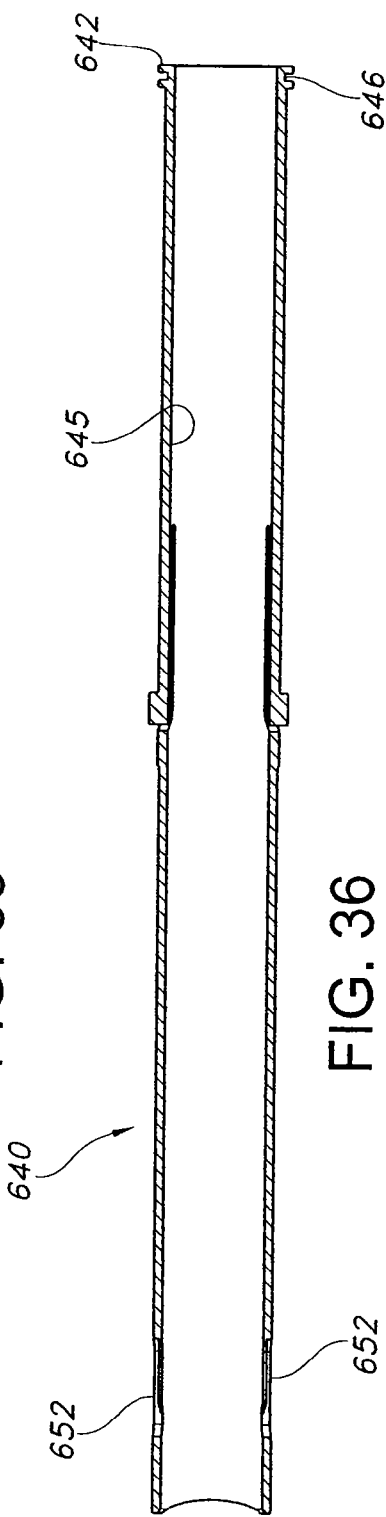
FIG. 36 is a side cross-sectional view of the outer shaft of the screw housing manipulator assembly of FIG. 30, taken though line 36-36 of FIG. 35.

Referring now to FIGS. 35 and 36, outer shaft 640 of screw housing manipulator 600 includes a proximal end 642 having a retaining ring 646, and a distal end 644. Outer shaft 640 is generally cylindrical, forming a bore 645 that extends through the length of the outer shaft. The diameter of bore 645 is adapted to receive inner shaft 610 and slidably engage the inner shaft in a fixed orientation relative to the outer shaft. Inner shaft 610 includes a small longitudinal slot 628, and outer shaft 640 includes a small longitudinal slot 652 that aligns with the slot of the inner shaft. Slots 628, 652 are adapted to receive a pin 660 that extends through both slots to lock the relative orientation of inner shaft 610 with respect to the orientation of the outer shaft 640.

Figure 37:
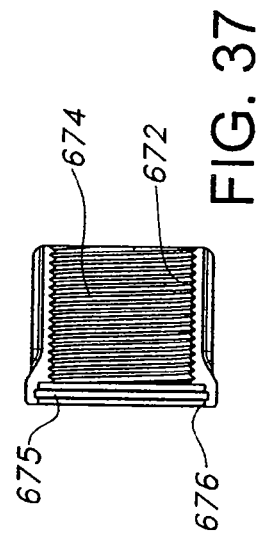
FIG. 37 is a side cross-sectional view of a collar component of the screw housing manipulator assembly of FIG. 30.

Inner and outer shafts 610, 640 are coupled to one another by control collar 670. Referring now to FIG. 37, control collar 670 is generally cylindrical and forms a central bore 672. Bore 672 includes an inner thread 674 that engages an external thread 618 on inner shaft 610. Bore 672 also includes a socket portion 675 forming an annular groove 676. Groove 676 receives a flange 647 on retaining ring 646 to interconnect collar 670 to the retaining ring. The threaded engagement between collar 670 and inner shaft 610 permits the collar to be axially displaceable along inner shaft 610. In contrast, the flange and groove connection between collar 670 and outer shaft 640 permits rotation of the collar relative to the outer shaft but substantially prevents axial displacement of the collar relative to the outer shaft. In this arrangement, control collar 670 is rotatable to axially advance inner shaft 610 relative to outer shaft 640 in a telescoping arrangement within bore 645.

Collar 670 is operable to displace flexible arms 620 between a clamping position, in which the arms are drawn proximally into outer shaft 640, and a release position, in which the arms are extended distally relative to the clamping position. In a relaxed condition, the distance between the outer surfaces of flexible arms 620 is slightly larger than the inner diameter of bore 645 in outer shaft 640. In this arrangement, the inner wall of bore 645 is configured to compress the flexible arms 620 inwardly and toward one another as the arms are drawn to the clamping position in outer shaft 640. Referring to FIGS. 33 and 34, each clamping extension 622 forms a bell-shaped socket 624 and a clamping tab 626 at the distal-most end of the clamping extension. Bell-shaped sockets 624 have an internal geometry that conforms with the geometry of upper housing 140 in screw assembly 100. Referring back to FIG. 6a, upper housing 140 has a curved shape that conforms with a curvature 625 in each bell-shaped socket 624. Upper housing 140 also includes a pair of opposing gripping slots 142, one on each side of upper locking flange 144. Gripping slots 142 are diametrically opposed with one another in a symmetrical arrangement and align radially with clamping tabs 626 in screw housing manipulator 600.

Referring again to FIG. 31, screw housing manipulator 600 is configured for insertion into plate reduction sleeve 550 to introduce a screw assembly 100 to plate 200. The orientation of screw assembly 100 relative to plate 200 is preferably controlled to ensure that the screw assembly, and particularly lower and upper housings 130, 140, enter the plate channel 250 in the correct orientation. To this end, the orientation of screw assembly 100 relative to plate 200 and plate reduction sleeve 550 is controlled by an indexing arrangement. Outer shaft 640 of screw housing manipulator 600 includes pair of flexible indexing tabs 648. Indexing tabs 648 each have a tab end 650 that extends radially outwardly from screw housing manipulator 600. Tab ends 650 register with a pair of diametrically opposed receiver slots 586 in inner shaft 570 of plate reduction sleeve 550, the slots being shown in FIGS. 27 and 28. The engagement between tab ends 650 and receiver slots 586 permit screw housing manipulator 600 to slide axially relative to plate reduction sleeve 550, but prevents the screw housing manipulator from rotating relative to the plate reduction sleeve.

Inner shaft 610 of screw housing manipulator 600 is hollow and forms a passage 611. Passage 611 extends along the longitudinal axis of screw housing manipulator 600, passing through handle 616. In this arrangement, passage 611 provides access to a screw assembly 100 after screw housing manipulator 600 is inserted into plate reduction sleeve 550. As will be discussed, the pedicle screw head 112, lower locking element 150, and upper locking element 160 in screw assembly 100 are all configured to cooperate with different sized drivers. Passage 611 provides one common axis portal for all the drivers.

Application of torque to the screw head and locking elements, particularly lower locking element 150, can require a substantial amount of torque. Preferably, the transfer of torque to plate 200 is eliminated or minimized. This can be accomplished in a number of ways. Referring now to FIGS. 38-41, exemplary components of a counter-torque kit are shown in accordance with the invention. The counter-torque kit is used to stabilize plate 200 and fix the plate against rotation as the locking elements within the screw assembly are tightened. Plate stabilization is accomplished with three components: a stabilization sleeve 710, the plate reduction sleeve 550 previously described, and a counter-torque handle 730 that applies counter force to the plate reduction sleeve.

Stabilization sleeve 710 is configured for insertion into plate reduction sleeve 550 to stabilize the position of plate 200 from inside channel 250. Sleeve 710 includes a proximal end 712 featuring a knob 713, and a distal end 714 with a pair of stabilizing plates 716. Each stabilizing plate 716 has a plate width "$W_p$" substantially equal to the width of channel 250 in plate 200. Stabilization sleeve 710 preferably includes an alignment mechanism that ensures that the sleeve is in the correct orientation to permit insertion of stabilizing plates 716 into channel 250. In the illustrated embodiment, proper alignment is facilitated by using the orientation of plate reduction sleeve 550 as a basis for setting the orientation of stabilization sleeve 710. Indexing slots 584 in plate reduction sleeve 550 are adapted to receive a pair of diametrically opposed projections 718 that extend radially outwardly from sleeve 710. Each projection 718 has a width that is equal to or slightly less than the width of indexing slots 584. The maximum width across projections 718 is greater than the inner diameter of plate reduction sleeve 550. In this arrangement, stabilization sleeve 710 can only be inserted into plate reduction sleeve 550 with projections 718 aligned with indexing slots 584. Projections 718 are also aligned radially with stabilizing plates 716. In this arrangement, stabilization sleeve 710 can only be inserted into plate reduction sleeve 550 with stabilizing plates 716 oriented perpendicularly to the longitudinal direction of plate 200. As such, the stabilizing plates are in proper alignment to be inserted into channel 250 without the need for rotational adjustment.

Referring next to FIGS. 40 and 41, counter-torque handle 730 includes a head 732 connected with a handle assembly 740. Head 732 includes a base portion 734 for attachment with handle assembly 740 and a curved extension 736. Curved extension 736 has a first plug 738 that extends inwardly relative to the curvature of the extension. Handle assembly 740 includes a handle body 742 for gripping the counter-torque handle 730 and a central bore 744. An elongated rod 746 is axially displaceable in bore 744 between an extended position to lock the counter-torque handle 730 to an article and a retracted position to release the counter-torque handle from an article. In the extended position, rod 746 projects outwardly from base portion 734 in an exposed manner to adjacent curved extension 736. The exposed portion of rod 746 forms a second plug 748, as shown in FIG. 40. Together, first plug 738 and second plug 748 form a secure coupling with a counter-torque engagement surface.

A biasing spring 752 circumscribes the rod near the proximal end of handle body 742. A first end of spring 752 bears against an inner cap 754 in the proximal end of handle body 742, and a second end of spring 752 bears against an enlarged midsection 750 of rod 746. Spring 752 is compressed between inner cap 754, which is fixed relative to handle body 742, and midsection 754 of rod 746, which is axially displaceable relative to the handle body. In this arrangement, stored energy in spring 752 biases rod 746 toward the extended or locking position. A pull knob 756 attached to rod 746 is operable to draw the rod proximally against the bias of spring 752 toward the retracted position.

Counter-torque handle 730 is configured to engage a counter-torque surface on plate reduction sleeve 550. Referring again to FIGS. 23-26, outer shaft 552 of plate reduction sleeve 550 is circumscribed by engagement surface 566. Engagement surface 566 includes an arrangement of holes 568 incrementally spaced at equal distances from one another around the circumference of outer shaft 552. The arc length between first plug 738 and second plug 748 generally corresponds to the arc length between two of holes 568. In this arrangement, any two holes 568 are adapted to receive first plug 738 and second plug 748 when curved extension engages engagement surface 566.

Figure 42:
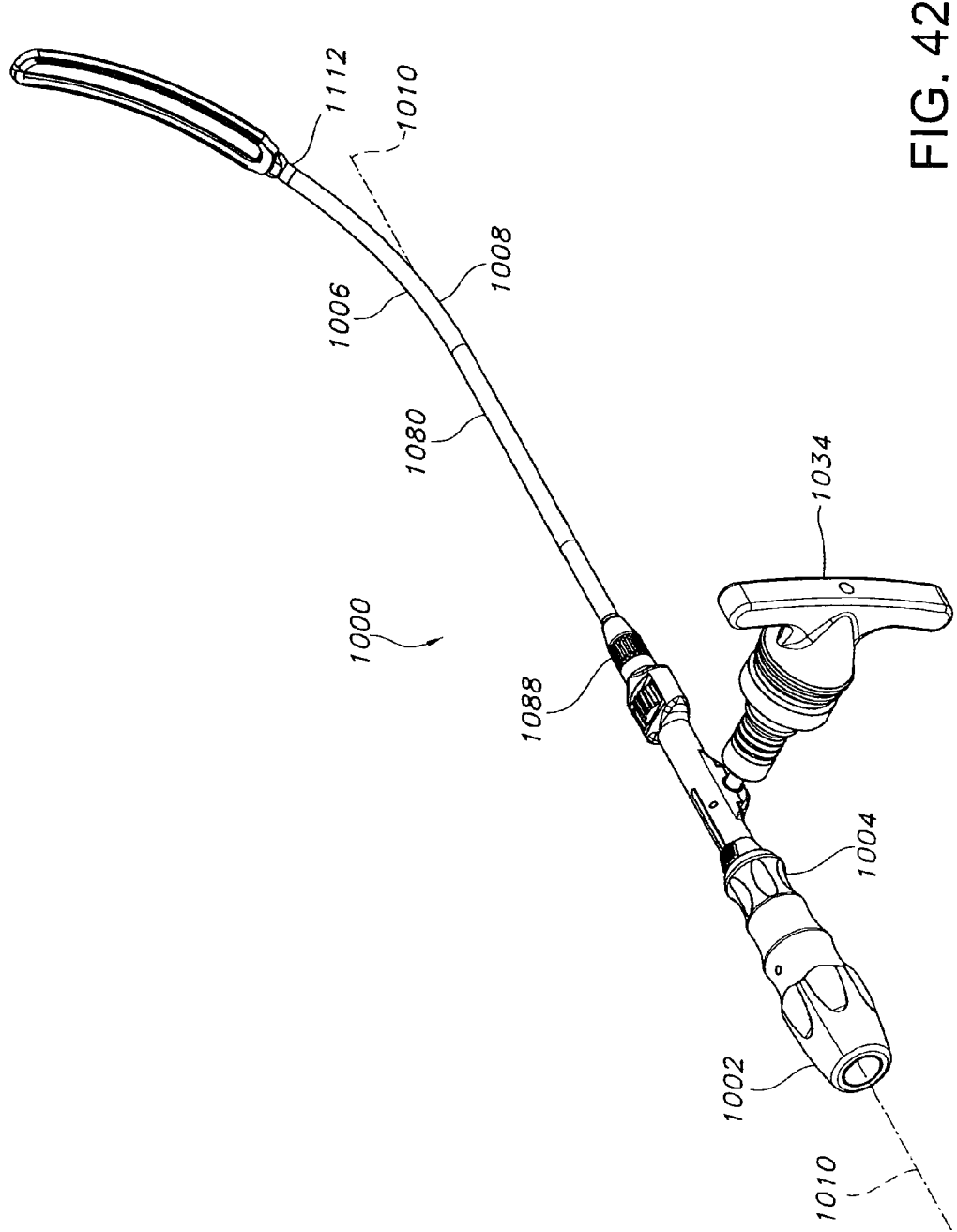
FIG. 42 is a perspective view of an inserter according to an exemplary embodiment of the present invention shown with a stabilization plate.
Figure 43:
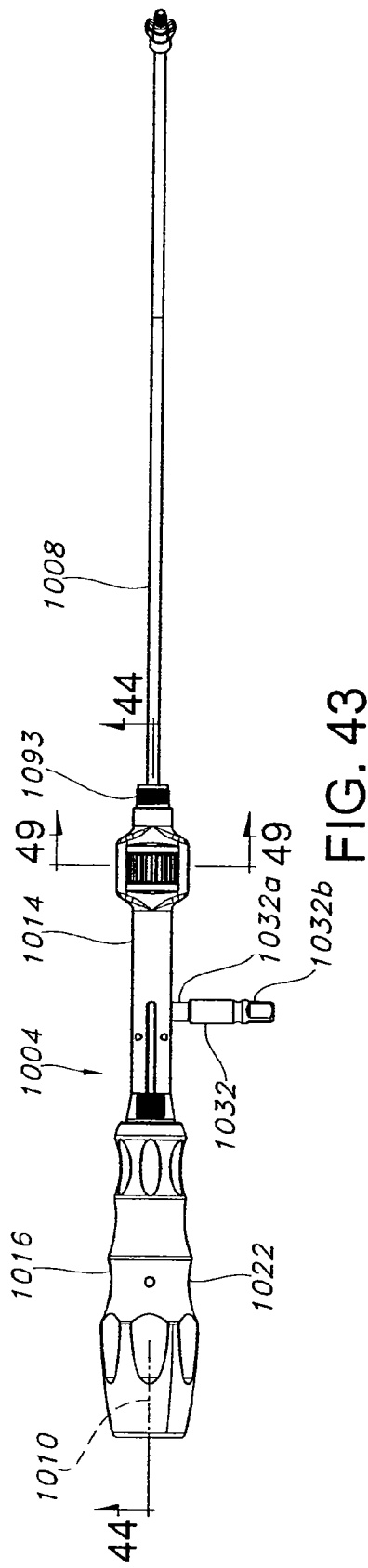
FIG. 43 is a top plan view of the inserter shown in FIG. 42.

Referring now to FIGS. 42 and 43, an inserter instrument 1000 for use with the spinal stabilization system 10 is shown in accordance with one exemplary embodiment of the invention. Inserter 1000 can be used to insert plate 200 through an incision and position the plate above two or more vertebral bodies to be stabilized. Inserter 1000 is also operable to adjust the relative position of screw assemblies 100 within plate channel 250. Adjustment of the screw assemblies 100 is done with a very small probe that penetrates through an end of plate 200 and into plate channel 250 where it engages the screw assembly to be adjusted. More specifically, the small probe passes through portal 214 in plate 200, and engages notch 138 on the side of screw assembly 100. With this arrangement, inserter 1000 allows the screw assemblies 100 to be adjusted remotely with minimally invasive procedures. Adjustment of the screw assemblies 100 can be performed to adjust the position of the vertebral bodies, and apply compression or decompression to the disc space (depending on direction of movement).

Inserter 1000 is generally elongated in shape and includes a proximal end 1002, having a handle assembly 1004, and a distal end 1006, having a flexible shaft assembly 1008. A longitudinal axis 1010, extends generally between proximal end 1002 and distal end 1006. Flexible shaft assembly 1008 is configured to extend in a distal/proximal direction relative to handle assembly 1004 generally along longitudinal axis 1010, and to also rotate about longitudinal axis 1010. Flexible shaft assembly 1008 is generally cylindrically shaped, with a distal tip 1112 that curves away from longitudinal axis 1010. Flexible shaft assembly 1008 includes an inner shaft 1009 slidably disposed within an outer shaft 1011, as shown in FIG. 44.

Figure 44:
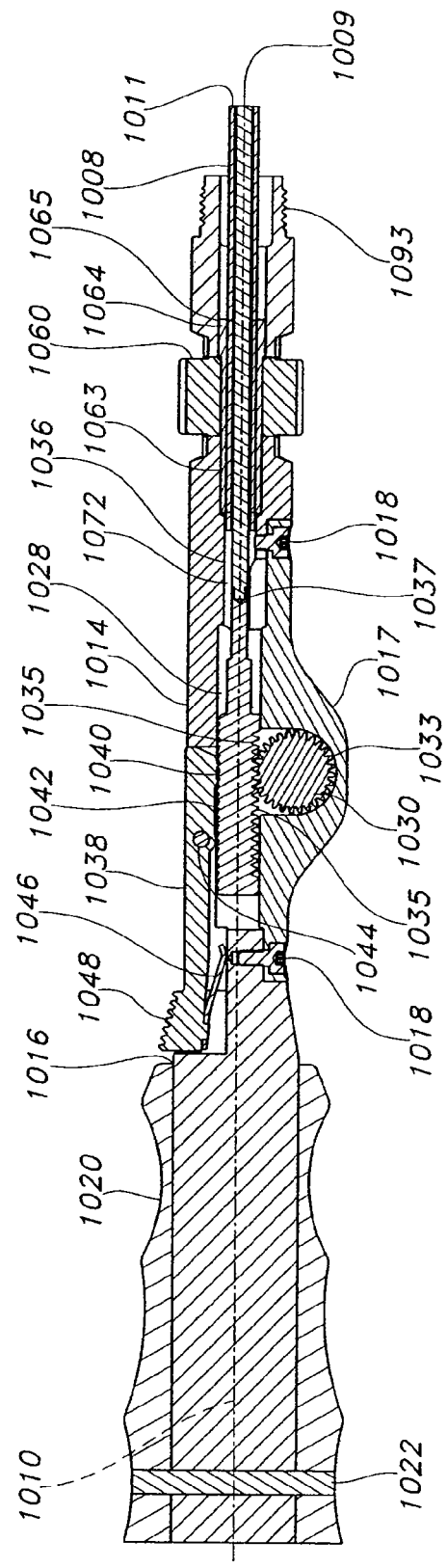
FIG. 44 is a cross-sectional view of a portion of the inserter taken through lines 44-44 of FIG. 43.
Figure 45:
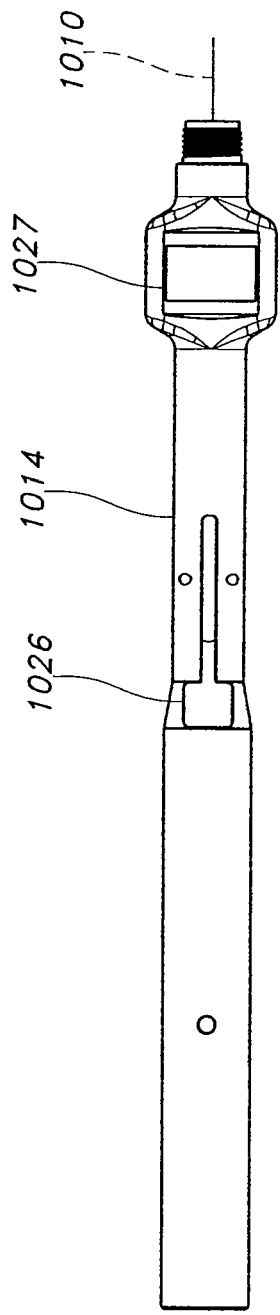
FIG. 45 is a top plan view of a handle body of the inserter shown in FIG. 42.

Referring to FIGS. 43 and 44, handle assembly 1004 includes a handle body 1014 fixedly coupled to a handle grip assembly 1016. Handle assembly 1004 includes a handle body 1014 and a handle cover 1017 releasably coupled to handle body 1014, such as by threaded fasteners 1018. Handle grip assembly 1016 includes a contoured grip 1020 having a plurality of ridges to facilitate tactile feel. Grip 1020 may be constructed from polyetherether ketone (PEEK) or some other suitable material. In an exemplary embodiment, a pin 1022 may be inserted through grip 1020 and into handle grip assembly 1016, such as with an interference fit, to secure contoured grip 1020 to handle grip assembly 1016. Handle body 1014 houses and maintains the mechanism used both to extend and retract flexible shaft assembly 1008 and to rotate flexible shaft assembly 1008 about longitudinal axis 1010. Referring to FIG. 45, handle body 1014 includes a generally key-shaped slot 1026 that houses the mechanism to extend and retract flexible shaft assembly 1008 and a generally rectangular slot 1027. Rectangular slot 1027 provides access to a mechanism that rotates flexible shaft assembly 1008 about longitudinal axis 1010.

Figure 46:
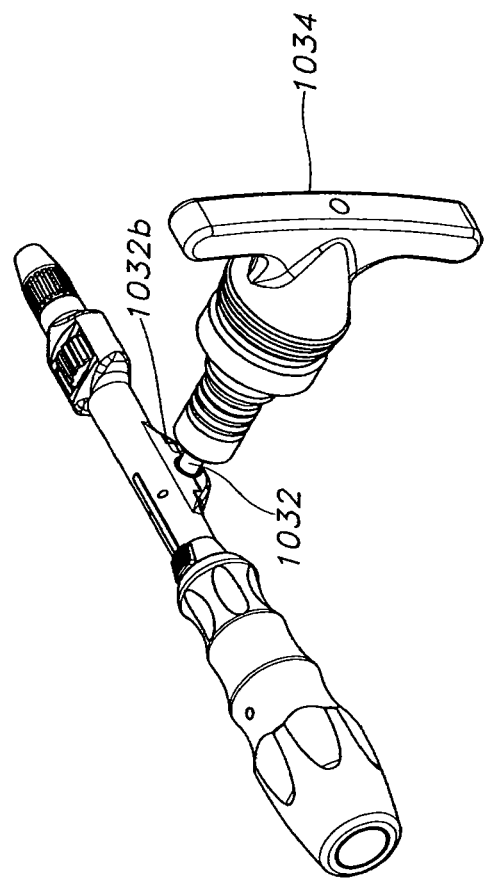
FIG. 46 is a perspective view of a handle portion of the inserter shown in FIG. 42.

Referring back to FIGS. 43 and 44, a rack 1028 and a pinion 1030 are housed within handle body 1014 and cooperate to advance and retract flexible shaft assembly 1008 along longitudinal axis 1010. Pinion 1030 is coupled to a first end 1032a of a pinion shaft 1032. A second end 1032b of pinion shaft 1032 is generally square in cross section. A gear handle assembly 1034, shown in FIG. 46, which is used to rotate pinion 1030, is coupled to the second end 1032b of pinion shaft 1032. Teeth 1033 on pinion 1030 engage teeth 1035 on underside of rack 1028 to advance and retract rack 1028 along longitudinal axis 1010.

Figure 47:
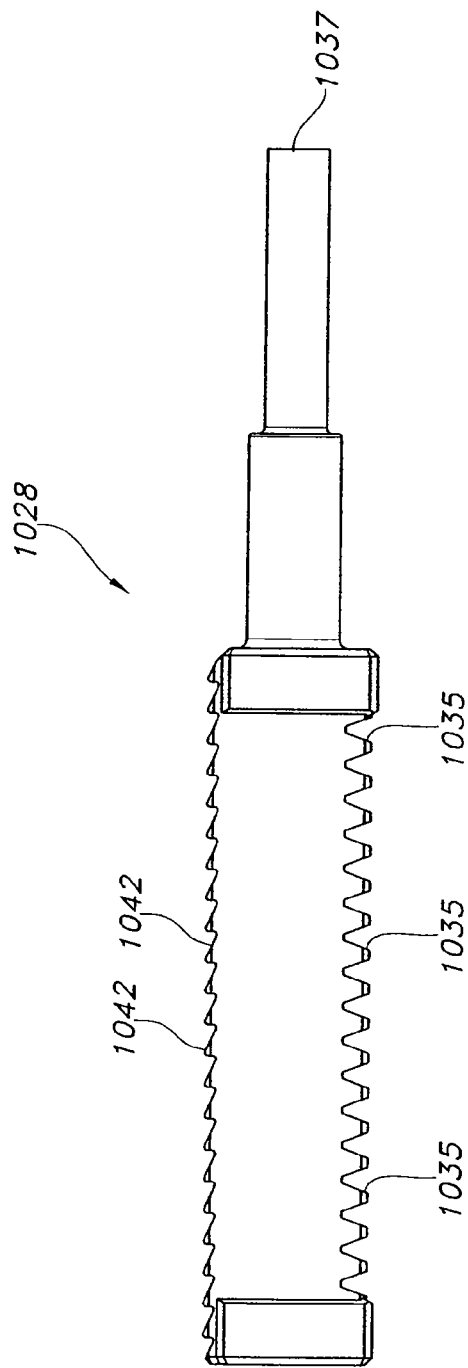
FIG. 47 is a side elevation view of a rack of the inserter shown in FIG. 42.
Figure 48:
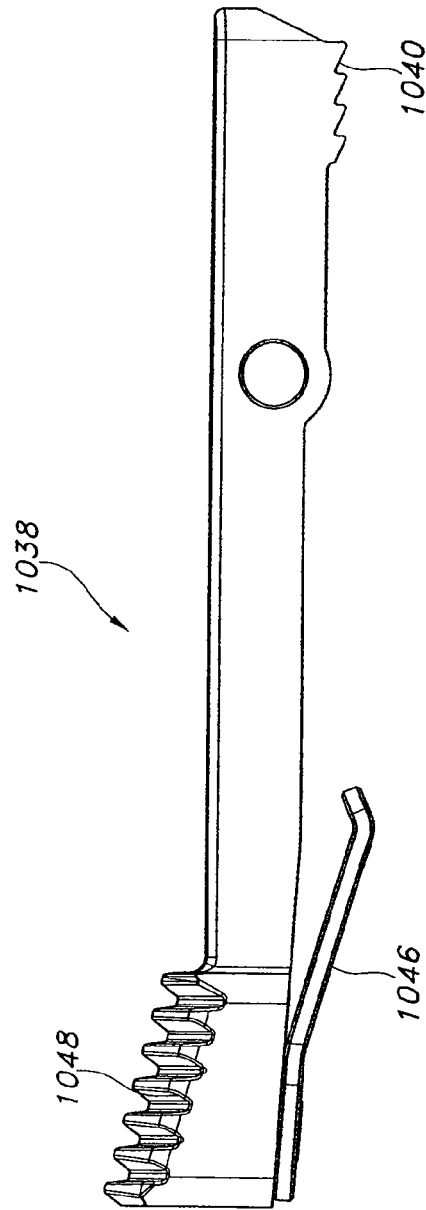
FIG. 48 is a side elevation view of a ratchet lever of the inserter shown in FIG. 42.
Figure 51:
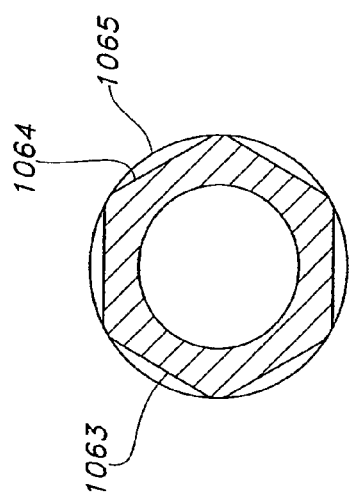
FIG. 51 is an end view of the sleeve of FIG. 50.
Figure 52:
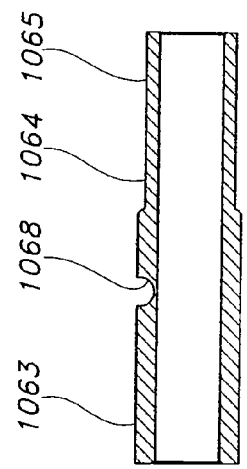
FIG. 52 is a side cross-sectional view of the sleeve of FIG. 50.
Figure 49:
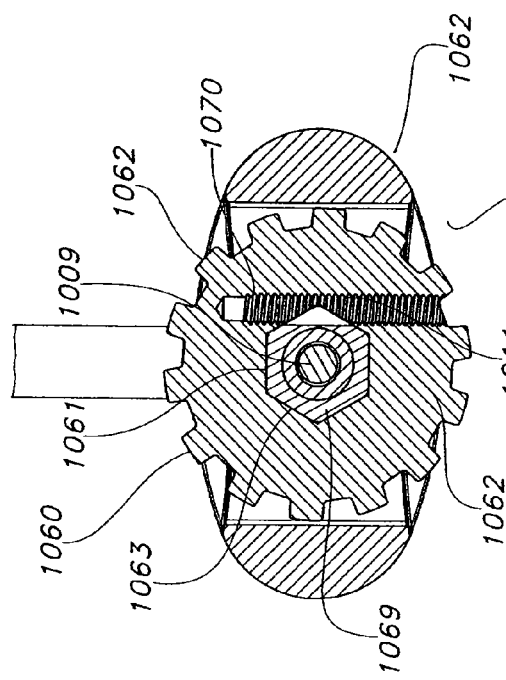
FIG. 49 is a cross-sectional view of an inserter knob of the inserter taken along lines 49-49 of FIG. 44.

Referring now to FIGS. 44, 47, and 48, rack 1028 is biased towards a proximal position by a biasing element in the form of a helical spring 1036. Pinion 1030 is used to advance rack 1028 in a distal direction, against the force of helical spring 1036. A ratchet lever 1038 is used to maintain rack 1028 in a distal position as pinion 1030 advances rack 1028 distally. Rack 1028 includes a cavity 1037 that receives and engages a proximal end of inner shaft 1009. Ratchet lever 1038 includes ratchet teeth 1040 that engage corresponding ratchet teeth 1042 on rack 1028. Ratchet lever 1038 is coupled to handle body 1014 via a pivot pin 1044. A leaf spring 1046 biases distal end of ratchet lever 1038 away from handle body 1014, pivoting ratchet teeth 1040 about pivot pin 1044 into engagement with ratchet teeth 1042 of rack 1028. In this arrangement, ratchet lever 1038 provides a lock that substantially prevents the rack and flexible shaft from reversing or moving in a proximal direction under the spring bias. Proximal end of ratchet lever 1038 includes a finger grip 1048 that, when depressed toward handle body 1014, disengages ratchet teeth 1040 on the ratchet lever from ratchet teeth 1042 on the rack 1028, allowing the rack and flexible shaft 1008 to retract in a proximal direction under the bias of the spring.

Figure 50:
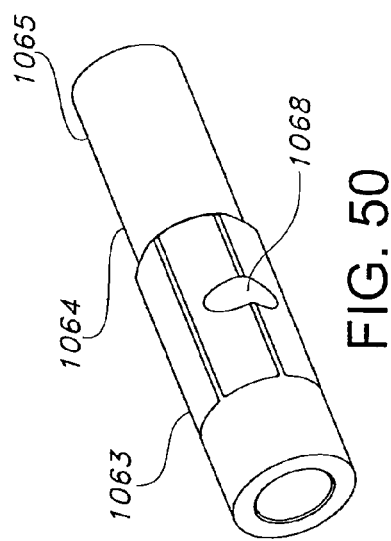
FIG. 50 is a perspective view of a sleeve that engages with the inserter knob of FIG. 49 and is mated with a flexible outer shaft.

Referring to FIGS. 44 and 49-52, flexible shaft assembly 1008 also includes an inserter knob 1060 that rotates flexible shaft assembly 1008 about longitudinal axis 1010. Inserter knob 1060 includes an annular body having a plurality of ridges 1062. Ridges 1062 provide a tactile grip for a user to rotate inserter knob 1060 about longitudinal axis 1010. Inserter knob 1060 includes a generally hexagonal inner perimeter 1061 that slides over a sleeve 1064. Inserter knob 1060 also includes a threaded slot 1066 that extends through the knob, passing partially through hexagonal inner perimeter 1061 and ending prior to exiting outer surface of inserter knob 1060. Sleeve 1064 includes a complementary, albeit unthreaded, slot 1068 through an outer periphery thereof. A screw 1070 extends through threaded slot 1066 and unthreaded slot 1068 to secure inserter knob 1060 to sleeve 1064. Sleeve 1064 includes a hexagonal proximal portion 1063 that mates with hexagonal inner perimeter 1061, as shown in FIG. 50, and a circular distal portion 1065. Screw 1070 engages outer shaft 1011 such that rotation of inserter knob 1060 about longitudinal axis 1010 also rotates outer shaft 1011 about longitudinal axis 1010.

Referring to FIG. 44, proximal end of flexible shaft assembly 1008 is disposed within a passage 1072 of handle body 1014 such that proximal end of inner shaft 1009 engages cavity 1037 in rack 1028. Proximal end of outer shaft 1011 engages helical spring 1036 to impart biasing force against rack 1028.

Figure 57:
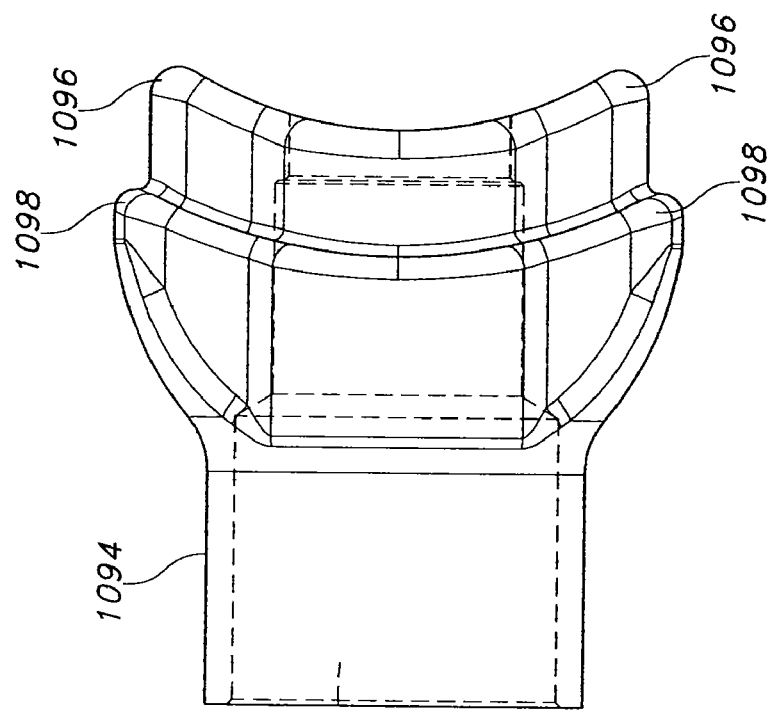
FIG. 57 is a side elevation view of the inserter tip shown in FIG. 56.
Figure 56:
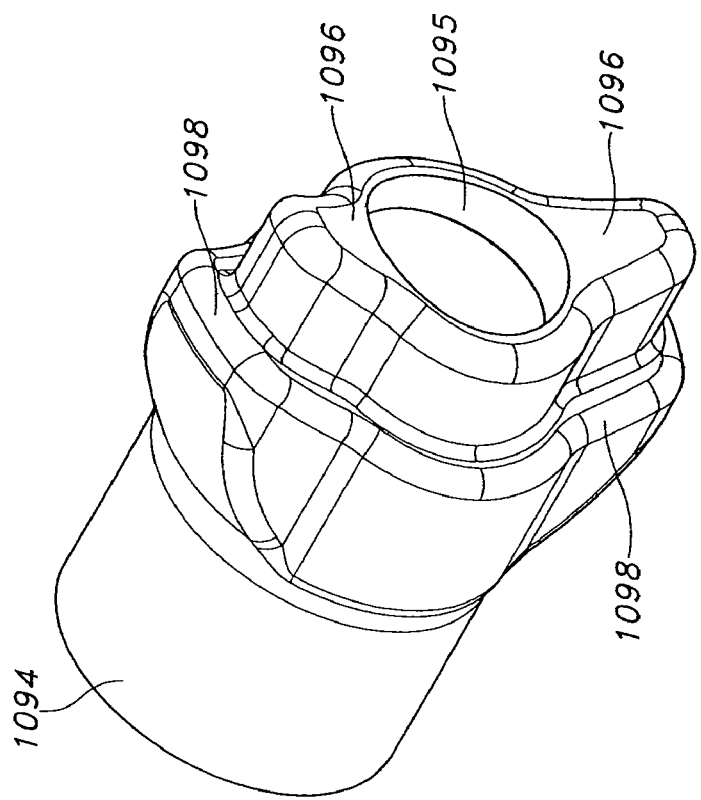
FIG. 56 is a perspective view of an inserter tip used in the inserter shaft shown in FIG. 53.

Referring now to FIGS. 42 and 53-57, flexible shaft assembly 1008 includes an inserter shaft 1080 that is positioned around outer shaft 1011 and inner shaft 1009. In FIG. 54, proximal end of inserter shaft 1080 includes a pair of spaced-apart, circular ridges 1082, 1084. A retaining ring 1086 is disposed between ridges 1082, 1084 and extends partially beyond ridges 1082, 1084. A tapered knob 1088 is slid over inserter shaft 1080 from its distal end toward the proximal end. Tapered knob 1088 includes a circumferential channel 1090, which accepts the portion of retaining ring 1086 that extends beyond ridges 1080, 1084, securing tapered knob 1088 to inserter shaft 1080. Tapered knob 1088 includes internal threads 1092 that engage external threads 1093 on distal end of handle body 1014 (shown in FIG. 44). Referring now to FIGS. 53, 56 and 57, distal end of inserter shaft 1080 includes an inserter tip 1094. Inserter tip 1094 includes a through-passage 1095 that allows inner shaft 1009 and outer shaft 1011 to extend therethrough. Inserter tip 1094 has a pair of diametrically opposed distal protrusions 1096 and a pair of diametrically opposed proximal protrusions 1098. Protrusions 1096, 1098 securely engage the proximal end 212 of plate 200 to substantially prevent twisting or rotating of the plate with respect to inserter 1000 during insertion. Distal protrusions 1096, 1098 are asymmetrical, forming a generally inverted U-shaped plug that conforms to the shape of aperture 215 in plate 200. In this arrangement, the distal end of inserter 1000 can only engage plate 200 in one orientation, preventing the user from inadvertently engaging the plate with the instrument in the wrong position.

Referring to FIGS. 58-60, outer shaft 1011 is shown. A distal end 1100 curves away from longitudinal axis 1010 by an angle α. In an exemplary embodiment, angle α is about 40°. Proximal end 1104 of outer shaft 1011 is coupled to interior of sleeve 1064 as described above. Distal tip 1102 includes a tip fitting 1106, shown in detail in FIGS. 59 and 60, that is permanently attached to distal tip 1102 of outer shaft 1011. Tip fitting 1106 includes exterior threads 1108 that engage threaded bore 216 in proximal end 212 of plate 200. Tip fitting 1106 includes a through passageway 1107 to allow inner shaft 1009 to pass therethrough.

Referring now to FIGS. 61-65, inner shaft 1009 is preferably constructed from a solid cylinder having a distal end 1109 that curves away from longitudinal axis 1010 with the same angle α as described above with respect to outer shaft 1011. Proximal end 1110 includes a cylindrical prong 1112 that fits into cavity 1037 of rack 1028.

An inner tip fitting 1114 is coupled to distal end 1108 of inter shaft 1009. Inner tip fitting 1114 includes a frustoconical distal tip 1116 and a cylindrical proximal opening 1118 that is sized to accept a distal prong 1109 extending from distal end 1108 of inner shaft 1009.

Like other instruments and assemblies in accordance with the invention, the inserter instrument 1000 and its parts may be manufactured using a variety of materials. In an exemplary embodiment, pin 1022 may be constructed from 303 stainless steel and leaf spring 1046 may be constructed from stainless steel. Additionally, retaining ring 1086, outer shaft 1011, and inner shaft 1009 may all be constructed from stainless steel. Also, in an exemplary embodiment, handle body 1014, handle cover 1017, rack 1028, pinion 1030, pinion shaft 1032, inserter knob 1060, sleeve 1064, inserter shaft 1080, tapered knob 1088, inserter tip 1094, tip fitting 1106, and inner tip fitting 1114 may all be constructed from precipitation hardening stainless steel, such as 17-4 PH™ stainless steel.

The foregoing assemblies and instruments may be used in a number of surgical techniques in accordance with the invention. In the sections below, a general description of a surgical procedure will be provided, followed by a description of how individual instruments and assemblies are operated.

Figure 65:
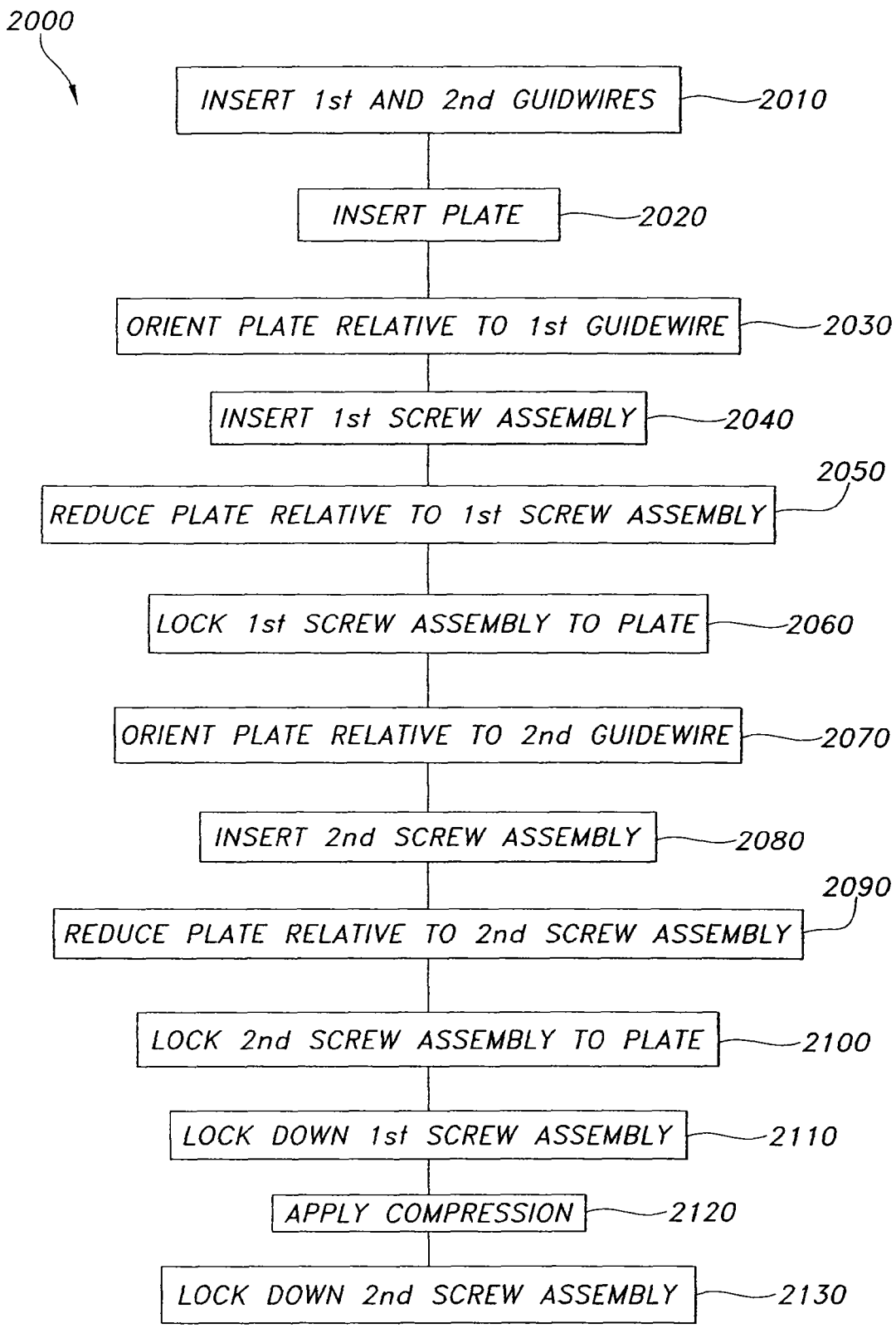
FIG. 65 is a block diagram outlining a procedure in accordance with one exemplary embodiment of the invention.

Referring now to FIG. 65, a general outline of one possible procedure 2000 in accordance with the invention is shown. For purposes of this description, the procedure will be described with reference to assemblies and instruments described in the sections above. It will be understood, however, that the techniques described in this section are not limited to the assemblies and instruments described in the above sections. In addition, it will be understood that procedure 2000 is a general description that may be supplemented with other steps without departing from the invention. Furthermore, the sequence of steps illustrated in FIG. 65 is exemplary only and does not represent the only contemplated sequence of steps that may be performed.

A plate may contain two or more screw assemblies, and consequently two or more guidewires. For purposes of FIG. 65 and the subsequent descriptions provided below, it will be assumed that the plate contains two screw assemblies: a first or distal screw assembly, and a second or proximal screw assembly. The term "first" refers to the screw or guidewire position that is farther away from the insertion instrument attached to the plate, and closer to the split end of the plate. The term "second" refers to the screw or guidewire position that is closer to the insertion instrument attached to the end of the plate. The procedure begins by driving a guidewire into each pedicle in step 2010. This is done, of course, after the bone screw locations and trajectories are carefully selected, and after a small incision or pair of incisions are made above the screw locations. Once the guidewires are in place, the plate is advanced to a position over the pedicles in step 2020. The plate is attached to the remote insertion instrument and advanced by remote manipulation though the incision. As the leading end of plate is advanced into engagement with each guidewire, each guidewire is snapped though the split end of the plate and into the plate's channel.

Once the plate is positioned over the guidewires, a first plate orientation assembly is advanced over the first guidewire to properly orient the plate with respect to the first guidewire in step 2030. That is, a first obturator and plate reduction sleeve are assembled together and slid down over the first guidewire. The first obturator tip is rotated into alignment with the plate channel and inserted down into the channel to orient the plate. The first plate reduction sleeve is subsequently secured to the plate to maintain the position of the plate. The first obturator is then removed from the plate reduction sleeve to clear the passage and allow for insertion of a first screw assembly. A first screw housing manipulator is loaded with the first screw assembly and passed over the first guidewire. Once the first screw housing manipulator is inserted into the first plate reduction sleeve, the first screw assembly is driven into the pedicle through the plate in step 2040. The first screw assembly is driven downwardly until an indicia line on the first screw housing manipulator aligns with a predetermined point on the plate reduction sleeve. At this point, the first screw assembly is driven to a sufficient depth so that the upper and lower locking flanges are in position to engage the plate once the plate is reduced.

The plate is reduced in step 2050 so that the plate extends perpendicular to the axis of the first screw assembly. In this position, the plate's side rails are axially aligned with and parallel to the upper locking flanges of the first screw assembly, and the plate's locking grooves are axially aligned with and parallel to the lower locking flanges of the first screw assembly. Once aligned, the first screw assembly is rotated to lock the assembly to the plate in step 2060. The upper locking flange is rotated so that it extends over the side rails, and the lower locking flange is rotated until it enters the locking grooves in each of the side rails.

In step 2070, a second plate orientation assembly is used to properly orient the plate with respect to the second guidewire. To accomplish this, a second obturator and plate reduction sleeve are assembled to one another and passed down over the second guidewire. The second obturator tip is rotated into alignment with the plate channel and inserted into the channel to orient the plate relative to the second guidewire. The second plate reduction sleeve is then locked to the plate to maintain the position of the plate. Once the second plate reduction sleeve is locked to the plate, the second obturator is removed from the second plate reduction sleeve to clear the portal in the second plate reduction sleeve. A second screw housing manipulator is loaded with a second screw assembly and passed over the second guidewire into the plate reduction sleeve. Once the second screw housing manipulator is inserted into the second plate reduction sleeve, the second screw assembly is driven into the pedicle through the plate in step 2080. As with the first screw assembly, the second screw assembly is driven down until an indicia mark on the second screw housing manipulator aligns with a predetermined point on the second plate reduction sleeve, signaling the point where the upper and lower locking flanges are at the appropriate depth to engage the plate. The plate is then reduced in step 2090 to align the plate's side rails 230 and locking grooves 257 parallel with the upper and lower locking flanges on the second screw assembly. The second screw assembly is then rotated to lock the assembly to the plate in step 2100.

In step 2110, the first screw assembly is locked down by tightening the lower locking element so that the lower housing is no longer free to articulate about the screw head. Compression is then applied to the bone graft material in the disc space in step 2120. To apply compression, the inserter is operated to advance the second screw assembly toward the first screw assembly within the plate channel. After sufficient compression is applied, the second screw assembly is locked down by tightening the lower locking element in step 2130. At this stage, plate insertion and adjustment is completed. The inserter, first plate reduction sleeve, second plate reduction sleeve, and any other instrumentation can be detached from the plate.

The manner in which the individual assemblies and instruments operate will now be described in greater detail in the following sections, which describe examples of surgical techniques.

Guidewire Insertion/Tissue Dilation

Many of the instruments and assemblies of the present invention are designed to be utilized in conjunction with fluoroscopic assistance, as described for example in U.S. Pat. No. 6,945,974, the contents of which are incorporated by reference. The orientation of each pedicle screw is pre-determined and set by placing a guidewire 350 into each vertebral body.

To begin insertion of the first guidewire, casing 320 is inserted into insertion handle 310, and the first guidewire 350 is advanced through the casing. The first guidewire 350 is positioned and oriented over a selected entry point and driven into place using slide hammer 326. Tissue that surrounds casing 320 can be spread open using dilator 400. Dilator 400 is advanced over casing 320 to the bone surface to dilate surrounding tissue. Once the first guidewire is positioned and sufficient tissue dilation is achieved, the same steps may be repeated for subsequent guidewires. All guidewires are placed, and tissue is dilated at each guidewire location, prior to insertion of plate 200.

Plate Insertion

Once the guidewires are properly set, plate 200 may be inserted into the incision and set in the desired position. Inserter 1000 is operable to insert plate 200 percutaneously through an incision in a minimally invasive manner that minimizes the amount of tissue and muscle that must be disturbed. Prior to insertion of plate 200, inserter 1000 is connected with the plate. Distal protrusions 1096 on inserter tip 1094 are aligned with and inserted into the shaped aperture 215 on the end of plate 200. Inner and outer shafts 1009, 1011 are then advanced distally through the shaped aperture 215 until tip fitting 1106 reaches threaded bore 216 in the end of the plate. Tip fitting 1106 is threaded into threaded bore 216 by rotating knob 1060. Once tip fitting 1106 is threaded into bore 216, plate 200 is secured onto the inserter 1000. Plate 200 is then inserted percutaneously through the incision and maneuvered through tissue into a desired position. The curvature of flexible shaft 1008 provides a comfortable approach angle that permits the plate to be guided into the incision and through the tissue. Positioning of plate 200 can be done with the aid of fluoroscopy or other imaging techniques. Once plate 200 is in the desired position, the plate's position can be fixed by either manually holding the inserter 1000 in a stationary position, or by connecting the inserter to a table clamp or similar apparatus.

Plate Centering and Angling

As noted above, plate 200 must be oriented with respect to the patient's spine, the guidewires and the screw assembly. The orientation procedure can be separated into two phases: (1) plate centering and (2) plate angling. In plate centering, plate 200 is positioned so that each guidewire passes through a centerline of plate channel 250. That is, each guidewire passes through channel 250 at a point that is equidistant from the side rails 230. In addition, the axis of the guidewire 350 must be parallel to the planes of sidewalls 257.

A first plate orientation assembly 500 is preferably pre-assembled and placed with the other instrumentation in accordance with standard procedures for surgical preparation. To assemble the first plate orientation assembly 500, a first obturator 510 is inserted into a first plate reduction sleeve 550 and turned until indexing detents 514 on the obturator snap into indexing slots 579 in the plate reduction sleeve. At this stage, obturator 510 and plate reduction sleeve 550 are locked together axially and radially, enabling the assembled components to function as one instrument. Control knob 532 on obturator 510 is turned to set indicia line 532a to the unlocked setting. The first guidewire 350 is then inserted into the bore in obturator tip 516. Once guidewire 350 is inserted into tip 516, plate orientation assembly 500 is advanced over guidewire 350 and lowered into engagement with plate 200. Conical tapered end 518 of obturator 510 enters channel 250, with the conical sides engaging side rails 230. Because tapered end 518 is concentric with guidewire 350, plate 200 is laterally shifted so that the inner sidewalls 256 of channel 250 are equidistant from the guidewire 350, thereby centering the plate.

Obturator tip 516 is pressed further downwardly until straight section 517 of obturator 510 engages the side rails of plate 200. At this stage, straight section 517 will not enter channel 250 unless flat sides 517a of the straight section are parallel with side rails 230. The surgeon will detect a resistance to insertion if the surfaces are not parallel, signaling that the obturator tip 516 is not aligned with the channel 250. In such an instance, plate orientation assembly 500 is rotated as necessary until flat sides 517a of obturator 510 extend parallel with side rails 230 and align with channel 250. In this orientation, obturator tip 516 passes into channel 250 and captures plate 200 with guidewire 350 centered between side rails 230 and parallel to sidewalls 257. As obturator tip 516 enters channel 250, the capturing of plate 200 may be sensed by tactile feel. Control knob 532 on obturator 510 is turned to set indicia line 534 to the locked setting. By turning control knob 532 to the locked setting, inner shaft 522 is rotated until lobes 526 push locking springs 536 outwardly. Spring tabs 538 extend through spring tab slots 520 in obturator tip 516 and pass beneath lower surfaces 234 of side rails 230. Side rails 230 are thereby captured between spring tabs 538 and the distal end of obturator body 512. Because obturator tip 516 is concentrically positioned around guide wire 350, the plate is locked with the guidewire centered in the plate.

Proper engagement between obturator 510 and plate 200 may be confirmed by maneuvering the plate with the obturator. The surgeon checks that proper engagement with plate 200 is made by carefully moving the plate orientation assembly 500 relative to the plate. Movement should be limited to articulation within the longitudinal plane of plate 200. Proper locking of plate 200 can also be confirmed under lateral fluoroscopy or other imaging techniques.

As obturator tip 516 enters channel 250 to center plate 200 around guidewire 350, the plate is also adjusted so that the guidewire is parallel to inner sidewalls 256 of channel 250. Flat sides 517a of obturator tip 516 engage inner sidewalls 256 in plate 200 so that the sidewalls are brought parallel to the direction of the guidewire.

The obturator 510 serves to orient the guidewire with respect to the plate 200, as noted above. Obturator 510 also rotationally and axially orients the plate reduction sleeve with respect to the plate 200. Once the proper orientation of obturator 510 and plate reduction sleeve 550 are confirmed, the plate reduction sleeve is ready for axial displacement and engagement with the plate.

Plate reduction sleeve 550 is operable in three positions or settings during manipulation of plate 200. Once obturator 510 is locked in the proper position, control knob 590 on plate reduction sleeve 550 is moved to a first position to axially unlock the plate reduction sleeve from the obturator. In this condition, plate reduction sleeve 550 can be axially advanced downwardly toward plate 200. The amount of axial advancement required is preferably indicated by indicia, such as a line on the exterior of obturator 510. From this position, control knob 590 is then moved to a second position to lock the advanced plate reduction sleeve 550 onto plate 200. The locking of plate reduction sleeve 550 to plate 200 can be confirmed by tactile feel, such as by pulling upwardly on the plate reduction sleeve 550 in a direction away from the plate. Locking can also be confirmed under fluoroscopy. Once plate reduction sleeve 550 is locked to plate 200, obturator 510 can be unlocked from the plate and withdrawn out of the plate reduction sleeve, clearing the passage inside the plate reduction sleeve.

Insertion of First Screw Assembly

Once the plate 200 is properly centered and angled with respect to the first guidewire, the first screw assembly is inserted and attached to the plate. Prior to surgery, appropriate sized bone screws are selected and preloaded into a first screw housing manipulator 600. The first plate reduction sleeve 550 provides a portal 551 to introduce the first screw housing manipulator 600 to plate 200. To clear portal 551 and provide access to plate 200, the first obturator 510 is removed from the first plate reduction sleeve 550. At this stage, the first obturator is the only component that is holding the plate 200 in a properly centered and angled position. Therefore, before obturator 510 can be removed, plate reduction sleeve 550 is secured to plate 200 to preserve and maintain the centered and angled position of the plate. Plate reduction sleeve 550 is gauged and indexed in a coaxial relationship with obturator 510, so that clamping members 578 are properly oriented to engage side rails 230 of plate 200. Control knob 590 is rotated to retract outer shaft 552 relative to inner shaft 570, thereby opening flex arms 577. This has the effect of releasing plate reduction sleeve 550 from indexing detents 514 to disengage the plate reduction sleeve from obturator 510. Plate reduction sleeve 550 is then slid down over obturator 510 until clamping members 578 pass over plate 200 and detents 580 pass beneath lower surfaces 234 of side rails 230. Control knob 590 is then rotated to move outer shaft 552 distally over inner shaft and converge flex arms 577. Clamping members 578 are converged to the partially engaged condition around side rails 230. Side rails 230 of plate 200 are captured between inner gripping surfaces 582, but are able to translate through a small pivot angle. In this condition, plate reduction sleeve 550 is clamped over plate 200, but is free to articulate or "wand" within a plane parallel to the plate. Engagement between detents 580 and side rails 230 of plate 200 may be confirmed under lateral fluoroscopy, or other imaging techniques. With the first plate reduction sleeve 550 now clamped to plate 200, the first obturator 510 can be removed to clear portal 551. Control knob 532 of obturator 510 is rotated to the unlocked position to unlock tip 516 from plate 200. Once unlocked, obturator 510 is pulled out of plate reduction sleeve 550, clearing portal 551 for introduction of the first screw housing assembly 100.

The first screw housing assembly 100 is preferably pre-assembled and connected with a hex driver that engages the head 112 of pedicle screw 110. Screw housing assembly 100 and the hex driver are then loaded into the first screw housing manipulator 600. The loaded screw housing manipulator 600 is aligned over the proximal end of plate reduction sleeve 550 and portal 551. The distal tip 121 of screw 100 is positioned over the free end of guidewire 350, and the guidewire is slipped into guidewire bore 124. The screw assembly 100 and screw housing manipulator 600 are then passed down over the first guidewire and into portal 551 of plate reduction sleeve 550. At this stage, it is important to note that the orientation of screw assembly 100 is indexed with respect to screw housing manipulator 600. Screw housing manipulator 600, in turn, is indexed and gauged with plate reduction sleeve 550 so that the axial position and orientation of screw assembly 100 relative to plate 200 is controlled. In the preferred embodiment, portal 551 has diametrically opposed indexing slots or other alignment features that ensure that screw housing manipulator 600 and screw assembly 100 are inserted in proper alignment with plate 200. The alignment features may be configured, for example, to only permit screw housing manipulator 600 to enter portal 551 in the proper orientation relative to plate 200.

Once the first screw housing manipulator 600 is inserted into portal 551, the first screw assembly 100 is advanced into the plate channel 250. Guidewire 350 controls the trajectory of screw assembly 100 as it is passed down through portal 551 and driven into the pedicle. Preferably, the first screw assembly and instrumentation utilize components that minimize the potential for breaking the pedicle surface and dislodging or disturbing guidewire 350. In this regard, screw 100 preferably includes a self-tapping screw shank configuration that avoids the need for assistance with awls or other implements to tap the screw. By avoiding the use of awls, the potential for breaking the pedicle surface and losing the preset guidewire position is minimized. After the shank contacts the pedicle, the driver that is pre-attached to the first screw assembly is rotated to begin driving screw shank 120 into the pedicle. The hex driver is turned through a few rotations to begin driving a portion screw shank 120 into the pedicle. After the thread on shank 120 is started and driven a small distance over guidewire 350 into the pedicle, the angular position of the screw shank is now set. At this point, guidewire 350 is preferably removed from the patient as a safety precaution to prevent the risk of driving the guidewire through the pedicle. The surgeon then resumes rotating the hex driver to continue driving the screw 110 into the pedicle. During manipulation of screw assembly 100, it may be desirable to lift plate 200 to an elevated position within the tissue to minimize the risk of impingement with spinal processes.

As the hex driver is rotated to drive polyaxial screw 100 into the pedicle, screw housing manipulator 600 advances into plate reduction sleeve 550. The axial position of screw assembly 100 with respect to plate 200 is not visible from outside plate reduction sleeve 550. In a preferred embodiment, the instrumentation includes a set of indicia to indicate when screw assembly 100 is driven to the appropriate depth with respect to plate 200. Referring to FIG. 30, the first screw housing manipulator 600 includes an indicia line 649 etched on the exterior of outer shaft 640. Indicia line 649 is axially positioned to signal when the screw assembly 100, and specifically the lower locking flange 134, reaches a depth corresponding to the depth of locking grooves in plate 200. An axial distance "X" extends between the locking grooves 257 in plate 200 and the top of control knob 590 when plate reduction sleeve 550 engages the plate. The same distance "X" extends between indicia line 649 and lower locking flange 134 of screw assembly 100 when the screw assembly is clamped by screw housing manipulator 600. In this arrangement, the top of control knob 590 serves as a guide for determining when lower locking flange 134 aligns with locking grooves 257 in plate 200. When indicia line 649 aligns with the top of control knob 590, lower locking flange 134 is located in elevational proximity to locking grooves 257.

It is noted that at this stage, the lower and upper locking elements 150, 160 are not locked down in the first screw assembly 100. Lower locking element 150 is set in lower housing 130 in an unlocked condition to allow screw head 112 to pivot against seat 137, so that the screw maintains a polyaxial range of motion. Upper locking element 160 is also set in an unlocked condition to permit sufficient clearance for the side rails 230 of plate 200 between lower locking flange 134 and upper locking flange 144, as will be discussed.

Plate Reduction

Although screw assembly 100 is advanced into plate 200 with lower locking flange 134 in elevational proximity to locking grooves 257, the screw assembly will most likely be in an incorrect orientation to lock to the plate, as discussed previously. The orientation of screw 110, which aligns with the orientation of the first guidewire 350, is not perpendicular to plate 200 where it intersects the plate. As a result, lower locking flange 134 is not aligned parallel with locking grooves 257 and can not rotate into a locked position in the locking grooves. To bring lower locking flange 134 into alignment with locking grooves 257 and plate 200, the screw assembly 100 must be reduced to the orientation of the plate. In particular, lower screw housing 130 must be pivoted and rotated about screw head 112 until lower locking flanges 134 is aligned parallel to locking grooves 257. This rotational movement aligns the upper screw housing in a direction perpendicular to the longitudinal axis of plate 200. Control knob 590 on plate reduction sleeve 550 is rotated to retract clamping members 578 into outer shaft 552. As clamping members 578 are retracted, plate 200 is displaced relative to plate socket 564, to capture and move the plate reduction sleeve 550 in an orientation perpendicular to the longitudinal axis of plate 200.

Locking the First Screw Assembly to the Plate

Once plate 200 is reduced to an orientation that is perpendicular to the first screw assembly 100, lower and upper locking flanges 134, 144 are properly oriented for locking. To lock the first screw assembly 100 to plate 200, handle 616 of screw housing manipulator 600 is rotated approximately 90 degrees to rotate the lower and upper screw housings 130, 140. Upper flange 144 rotates until the rows of bosses 145 align over angled faces 236 of side rails 230. In addition, lower flange 134 rotates until the short sides enter into locking grooves 257 in channel 250. The arrangement of sharp corners 135 and tapered corners 136 on lower locking flange controls which direction of rotation effects locking of lower and upper housings 130, 140. The locking grooves 257 provide only a small degree of radial clearance for lower locking flange 134. The minimal clearance is not large enough to permit sharp corners 135 to rotate into the grooves. Tapered corners 136, in contrast, are able to rotate into the locking grooves. Therefore, placement of tapered corners 136 in the positions shown in FIG. 5, for example, would allow locking of the housings in response to clockwise rotation of screw assembly 100.

Once lower and upper flanges 134, 144 are rotated into the locked orientations, side rails 230 of plate 200 are captured in rail slots 146 between the lower and upper flanges. Upper locking element 160 is now tightened over plate 200 to more securely lock the first screw assembly 100 to the plate. A driver tool is inserted into passage 611 of screw housing assembly 600 and inserted into a hex opening in proximal end 162 of upper locking element 160. The driver tool is then rotated to tighten upper locking element 160 on screw assembly 100. As upper locking element 160 is rotated, the engagement between external thread 164 on the upper locking element and inner thread 133 in lower housing 130 draws the upper locking element into the lower housing. Cap portion 165 bears against upper housing 140 and presses the upper housing firmly onto plate 200. The rows of bosses 145 interdigitate with recesses 238 in side rails 230 to enhance the clamping engagement of plate 200 and provide resistance to longitudinal slippage. Once bosses 145 engage recesses 238, lower and upper screw housings 130, 140 securely engage plate 200, with side rails 230 captured in rail slots 146. The first screw assembly 110 is thereby provisionally locked to plate 200. In particular, housing portions 130, 140 of first screw assembly 110 are fixed relative to plate 200. Screw 110 is still free to move polyaxially relative to plate 200, however.

Insertion and Locking of the Second Screw Assembly to the Plate

Once the first screw assembly 100 is locked to plate 200, many of the steps described above may be repeated for a second screw assembly. The second screw assembly may be manipulated and secured with its own dedicated set of instruments, including a second obturator, a second plate reduction sleeve and a second screw housing manipulator. Each of the dedicated instruments used with the second screw assembly are identical to the corresponding instruments used with the first screw assembly.

Prior to insertion of the second screw assembly, the plate must be reoriented with respect to the second guidewire location. Reorientation of the plate is done because the first polyaxial screw 110 of the first screw assembly 100 has not been locked down, allowing the plate to articulate relative to the first screw head 112. After plate 200 is oriented with respect to the second guidewire location, the second screw housing manipulator loaded with the second screw assembly is inserted into the second plate reduction sleeve and attached to the plate. The second screw assembly is provisionally locked to the plate using the same procedures used lock the first screw assembly to the plate.

Locking Down the First Screw Assembly

The first screw assembly can be locked down once the second screw assembly is connected with plate 200, and once the desired final positioning of the plate is achieved. A driver is inserted into the first screw housing manipulator 600, which is preferably left connected with the first screw assembly 100. The driver is advanced into the first screw assembly 100 until it engages socket 151 of lower locking element 150. The lower locking element 150 is then tightened down by torquing the driver until screw head 112 is tightly locked against seat 137 of lower housing 130.

Because lower housing 130 is free to pivot about screw head 112 during plate reduction, socket 118 in screw head 112 may not be coaxially aligned with the passages through lower and upper locking elements 150, 160. The degree of misalignment may be substantial enough to make it difficult to engage socket 118 using a standard hex driver through the screw assembly. Therefore, the instrumentation of the present invention preferably includes alternative driver implements that permit tightening of screw heads from angles of approach that are not aligned with the axis of the screw head sockets. For example, the instrumentation may include a ball-head driver or similar implement that is configured to engage a hex socket and exert torque from an odd angle.

Plate 200 should remain stationary while torque is being applied to lock down the screw assemblies. To keep plate 200 stationary, a counter-torque is simultaneously applied to plate reduction sleeve 550. To provide a counter-torque while locking down the first screw assembly, a counter-torque assembly is attached to the first plate reduction sleeve 550. The first screw housing manipulator 600 is removed from the first plate reduction sleeve 550 and replaced by a first stabilization sleeve 710. Stabilization sleeve 710 is inserted into portal 551 of plate reduction sleeve 550 and indexed with inner shaft 570. That is, stabilization sleeve 710 is turned until projections 718 align with indexing slots 584 in inner shaft 570. Sleeve 710 is then advanced into plate reduction sleeve 550. In the aligned orientation, stabilizing plates 716 are positioned to enter channel 250 and bear against inner sidewalls 256. Counter-torque handle 730 is then connected to the first plate reduction sleeve 550. To attach counter-torque handle 730, pull knob 756 is pulled out of handle body 742 against the bias of spring 752 to retract second plug 748 into head 732. Head 732 is then placed around counter-torque coupling 566 on plate reduction sleeve 550. First plug 738 is inserted into one of the holes 568 that surround the coupling surface. At this position, the retracted second plug 748 is aligned with another of the holes 568. Pull knob 756 is then released, and spring 752 projects second plug 748 outwardly into engagement with the corresponding hole 568 to releasably lock the counter-torque handle 730 to plate reduction sleeve 550.

Once counter-torque handle 730 is locked to the first plate reduction sleeve 550, the driver attached to lower locking element 150 can be rotated to lock down the lower locking element. As the driver is rotated, an equal and opposite counter-torque is applied with counter-torque handle 730. The counter-torque is applied to engagement surface 566 on outer shaft 552, which is distributed to inner shaft 570 and stabilization sleeve 710 through their respective alignment members. Stabilization sleeve 710, in turn, distributes the counter-torque from stabilizing plates 716 to the channel sidewalls 256 in plate 200. With this counter-torque, plate 200 is held in a stable position and resists twisting while torque is applied to lock down the first screw assembly 100.

Compression

Plate 200 provides external stabilization to a fusion site. For proper fusion to occur, pressure must be maintained on the bone fusion material. Inserter instrument is operable to apply compression to the fusion material. To perform compression, the first screw assembly is locked down using the procedure described above. Once first screw assembly is locked down, the inserter is operated to move the second screw assembly in the plate channel 250 toward the first screw assembly. Moving the second screw assembly toward the first screw assembly presses the two vertebrae together and applies compression to the bone material at the fusion site.

To begin compression, inner shaft 1009 of inserter 1000 is advanced distally into engagement with the second screw assembly 100. Inner shaft 1009 is advanced by rotating gear handle assembly 1034. As gear handle assembly 1034 is rotated, pinion 1030 advances rack 1028 distally and pushes inner shaft 1009 distally toward the second screw assembly. As inner shaft 1009 is advanced, distal tip 1116 advances through the plate end wall and into plate channel 250 until it abuts the second screw assembly 100. The distal end of tip 1116 is axially aligned with notch 138 in lower housing 130 of the second screw assembly 100 and advances into the notch. The forward progress of the inner shaft 1009 is maintained by ratchet teeth 1040 on ratchet lever 1038, which prevent the shaft from reversing direction. Ratchet teeth 1040 engage ratchet teeth 1042 on rack 1028 to prevent helical spring 1036 from retracting inner shaft 1009 under the spring bias. As inner shaft 1009 advances, distal tip 1116 pushes the second screw assembly 100 along the plate channel 250 toward the first screw assembly 100. Lower locking flange 134 slidably engages the interior of the locking grooves 257 as the screw assembly 100 is moved. Once second screw assembly 100 reaches a desired position, the upper locking flange can be locked down onto the side rails 230 of plate 200 to fix the position of the screw assembly relative to the plate.

After second screw assembly 100 has been displaced to a desired location along plate 200, inner shaft 1009 is retracted by depressing finger grip 1048 on ratchet lever 1038. Depression of finger grip 1048 pivots ratchet teeth 1040 on lever 1038 out of engagement with ratchet teeth 1042 on rack 1028 to release the rack. Helical spring 1036 propels inner shaft 1009 proximally back into the inserter 1000, and disengages the distal tip 1116 from the notch in second screw assembly 100.

Locking Down the Second Screw Assembly

As noted above, the rack and pinion of inserter 1000 includes a ratcheted engagement that prevents the inner wire/shaft from reversing or backing out of the plate. In this arrangement, compression force is maintained against the second screw assembly so long as the instrument is connected to plate 200. Second screw assembly is then locked down by inserting the appropriate driver into the lower locking element of the second screw assembly and tightening the lower locking element in the same manner described above. Once the second screw assembly is locked down, the inserter instrument, first plate reduction sleeve, second plate reduction sleeve, and any other instrumentation still attached to the plate can be disconnected from the plate.

While preferred embodiments of the invention have been shown and described herein, both in terms of structure and methods of operation, it will be understood that such embodiments are provided by way of example only. Numerous variations, changes and substitutions will occur to those skilled in the art without departing from the scope of the invention. Accordingly, it is intended that the appended claims cover all such variations as fall within the scope of the invention.

What is claimed:

1. A method for implanting a spinal stabilization plate, the method comprising the steps of:
   inserting an elongated plate into a space above a first vertebra and a second vertebra, the plate having proximal end, a distal end and a channel extending between the proximal end and the distal end;
   advancing a first screw assembly through the channel and into the first vertebra;
   advancing a second screw assembly through the channel and into the second vertebra;

inserting a pusher member through the proximal end of the plate and into the channel into contact with the second screw assembly; and advancing the pusher member in a direction generally parallel to the direction of the channel to push the second screw assembly toward the first screw assembly and apply compression between the first vertebra and the second vertebra.

2. The method of claim 1 wherein the step of inserting a pusher member through the proximal end of the plate comprises advancing a shaft into the channel through a bore that extends through the proximal end of the plate.

3. The method of claim 1 further comprising the step of retracting the pusher member from the proximal end of the plate after compression is applied between the first vertebra and the second vertebra.

4. The method of claim 1 wherein the step of advancing a first screw assembly through the channel and into the first vertebra comprises the steps of advancing a first screw carrier of the first screw assembly through the channel and driving a first polyaxial screw contained in the first screw carrier into the first vertebra.

5. The method of claim 4 further comprising the step of rotating a locking flange on the first screw carrier into a groove extending along a sidewall in the channel to connect the first screw carrier in the channel in a slidable arrangement.

6. The method of claim 1 wherein the step of advancing a first screw assembly through the channel and into the first vertebra comprises the steps of advancing the first screw assembly over a guidewire driven into the first vertebra.

7. The method of claim 6, wherein the step of inserting an elongated plate into a space above a first vertebra and a second vertebra comprises the step of passing the guidewire through an opening in the distal end of the plate and into the channel to position the plate around the guidewire.

8. The method of claim 6, further comprising the step of advancing an instrument over the guidewire to center the guidewire between the side rails.

9. The method of claim 6, further comprising the step of advancing an instrument over the guidewire to draw the plate perpendicular to the guidewire.

10. The method of claim 1, wherein the step of inserting a pusher member through the proximal end of the plate and into the channel into contact with the second screw assembly comprises advancing an inner shaft through a bore that extends completely through the proximal end of the plate so that the inner shaft directly contacts the second screw assembly.

11. A method for implanting a spinal stabilization plate, the method comprising the steps of:
   inserting a plate into a space above a first vertebra and a second vertebra, the plate having proximal end, a distal end and a channel extending between the proximal end and the distal end;
   advancing a first screw carrier through a top side of the inserted plate and into the channel, the first screw carrier containing a first polyaxial screw;
   advancing a second screw carrier through the top side of the inserted plate and into the channel, the second screw carrier containing a second polyaxial screw;
   inserting a pusher member through the proximal end of the plate and into the channel into contact with the second screw carrier; and
   advancing the pusher member in a direction generally parallel to the direction of the channel to push the second screw carrier toward the first screw carrier and apply compression between the first vertebra and the second vertebra.

12. The method of claim 11 wherein the step of inserting a pusher member through the proximal end of the plate comprises advancing a shaft into the channel through a bore that extends through the proximal end of the plate.

13. The method of claim 11 further comprising the step of retracting the pusher member from the proximal end of the plate after compression is applied between the first vertebra and the second vertebra.

14. The method of claim 11 wherein the step of advancing a first screw carrier through a top side of the inserted plate comprises the step of driving the first polyaxial screw into the first vertebra.

15. The method of claim 11 further comprising the step of rotating a locking flange on the first screw carrier into a groove extending along a sidewall in the channel to restrict movement of the first screw carrier to a sliding arrangement along the length of the channel.

16. The method of claim 11, wherein the step of inserting a pusher member through the proximal end of the plate and into the channel into contact with the second screw carrier comprises advancing an inner shaft through a bore that extends completely through the proximal end of the plate so that the inner shaft directly contacts the second screw carrier.

17. A method for implanting a spinal stabilization plate, the method comprising the steps of: inserting a plate into a space above a vertebra, the plate having a pair of side rails and a channel between the side rails; attaching a socket element to the plate after the plate is inserted into the space above the vertebra, the socket element containing a polyaxial screw; driving the polyaxial screw into the vertebra to attach the plate with the vertebra; actuating a lower locking mechanism on the socket element to secure the socket element between the side rails in a sliding arrangement along the length of the channel; and actuating an upper locking mechanism on the socket element to fix the socket element to the side rails and restrict movement of the plate relative to the polyaxial screw; inserting a pusher member through a proximal end of the plate and into the channel into contact with the socket element, prior to the step of actuating the upper locking mechanism; and advancing the pusher member in a direction generally parallel to the direction of the channel to adjust the position of the socket element in the channel.

18. The method of claim 17, wherein the step of actuating a lower locking mechanism on the socket element comprises rotating a lower locking flange on the socket element into engagement with a track extending along the channel.

19. The method of claim 18, further comprising the step of advancing a pusher member through a proximal end of the plate and into the channel into contact with the socket element to push the socket element along the track in the channel.

20. The method of claim 17, wherein the step of actuating an upper locking mechanism on the socket element comprises pressing an upper locking flange on the socket element onto the side rails.

21. The method of claim 17, wherein the step of the step of inserting a pusher member through a proximal end of the plate and into the channel into contact with the socket element comprises advancing an inner shaft through a bore that extends completely through the proximal end of the plate so that the inner shaft directly contacts the socket element.

* * * * *